United States Patent
Godwin et al.

(10) Patent No.: US 12,428,679 B2
(45) Date of Patent: *Sep. 30, 2025

(54) PRIMER EXTENSION TARGET ENRICHMENT

(71) Applicants: Roche Sequencing Solutions, Inc., Pleasanton, CA (US); Kapa Biosystems, Inc., Wilmington, MA (US)

(72) Inventors: Brian C. Godwin, Livermore, CA (US); Joseph Platzer, Berkeley, CA (US); Janine Mok, Palo Alto, CA (US); Jo-Anne Penkler, Cape Town (ZA); Bronwen Miller, Cape Town (ZA)

(73) Assignees: Roche Sequencing Solutions, Inc., Pleasanton, CA (US); Kapa Biosystems, Inc., Wilmington, MA (US)

( * ) Notice: Subject to any disclaimer, the term of this patent is extended or adjusted under 35 U.S.C. 154(b) by 721 days.

This patent is subject to a terminal disclaimer.

(21) Appl. No.: 17/129,147

(22) Filed: Dec. 21, 2020

(65) Prior Publication Data

US 2021/0207211 A1  Jul. 8, 2021

Related U.S. Application Data

(62) Division of application No. 15/648,146, filed on Jul. 12, 2017, now Pat. No. 10,907,204.

(60) Provisional application No. 62/469,480, filed on Mar. 9, 2017, provisional application No. 62/361,426, filed on Jul. 12, 2016.

(51) Int. Cl.
  *C12Q 1/68*     (2018.01)
  *C12Q 1/6806*   (2018.01)
  *C12Q 1/6853*   (2018.01)
  *C12Q 1/6869*   (2018.01)

(52) U.S. Cl.
  CPC ......... *C12Q 1/6869* (2013.01); *C12Q 1/6806* (2013.01); *C12Q 1/6853* (2013.01)

(58) Field of Classification Search
  None
  See application file for complete search history.

(56) References Cited

U.S. PATENT DOCUMENTS

| 10,907,204 B2 * | 2/2021 | Godwin | C12Q 1/6853 |
| 2005/0123956 A1 * | 6/2005 | Blume | C12Q 1/683 435/6.12 |
| 2015/0210050 A1 * | 7/2015 | Liao | B32B 37/1284 428/12 |
| 2018/0016630 A1 * | 1/2018 | Godwin | C12Q 1/6806 |
| 2021/0207211 A1 * | 7/2021 | Godwin | C12Q 1/6806 |

FOREIGN PATENT DOCUMENTS

| WO | WO-2014144495 A1 * | 9/2014 | C07K 16/00 |
| WO | WO-2018013710 A1 * | 1/2018 | C12Q 1/6806 |

OTHER PUBLICATIONS

Gansauge et al., 2013. Single-stranded DNA library preparation for the sequencing of ancient or damaged DNA. Nature protocols, 8(4), pp. 737-748. (Year: 2013).*
Gansauge et al., 2017. Single-stranded DNA library preparation from highly degraded DNA using T4 Dna ligase. Nucleic acids research, 45(10), e79 ), pp. 1-10. (Year: 2017).*
Picelli et al., 2014. Full-length RNA-seq from single cells using Smart-seq2. Nature protocols, 9(1), pp. 171-181. (Year: 2014).*
Saliba et al., 2014. Single-cell RNA-seq: advances and future challenges. Nucleic acids research, 42(14), pp. 8845-8860. (Year: 2014).*

* cited by examiner

*Primary Examiner* — Gary Benzion
*Assistant Examiner* — Olayinka A Oyeyemi
(74) *Attorney, Agent, or Firm* — Charney IP Law LLC; Thomas M. Finetti

(57) ABSTRACT

Improved methods and compositions are provided herein for primer extension target enrichment of target polynucleotides.

8 Claims, 14 Drawing Sheets

Specification includes a Sequence Listing.

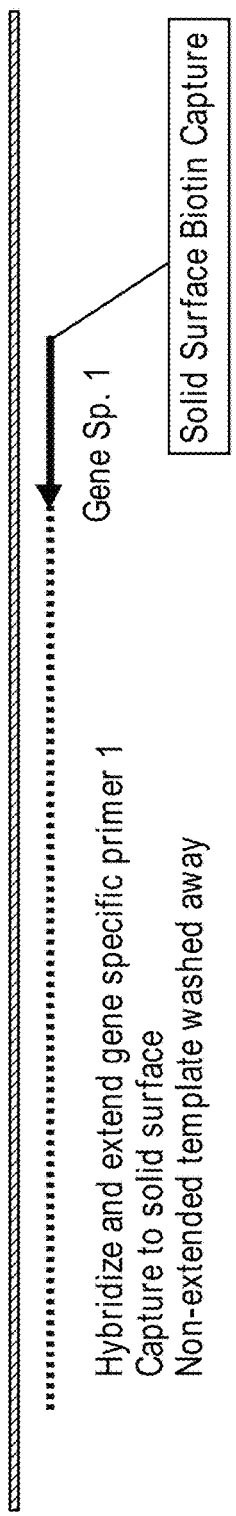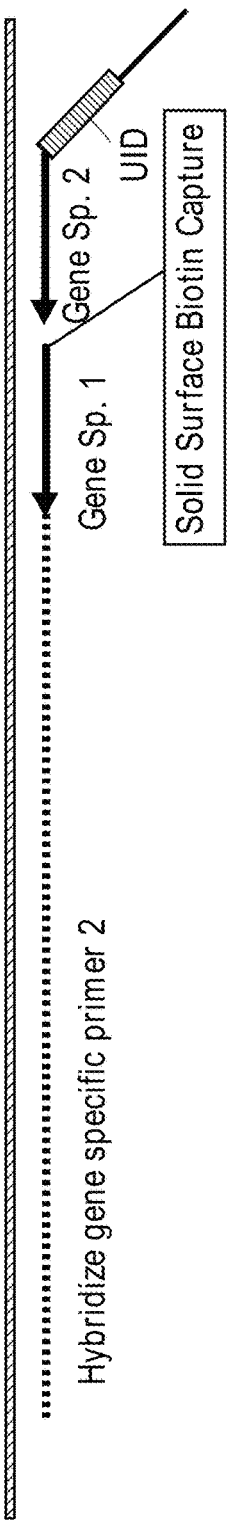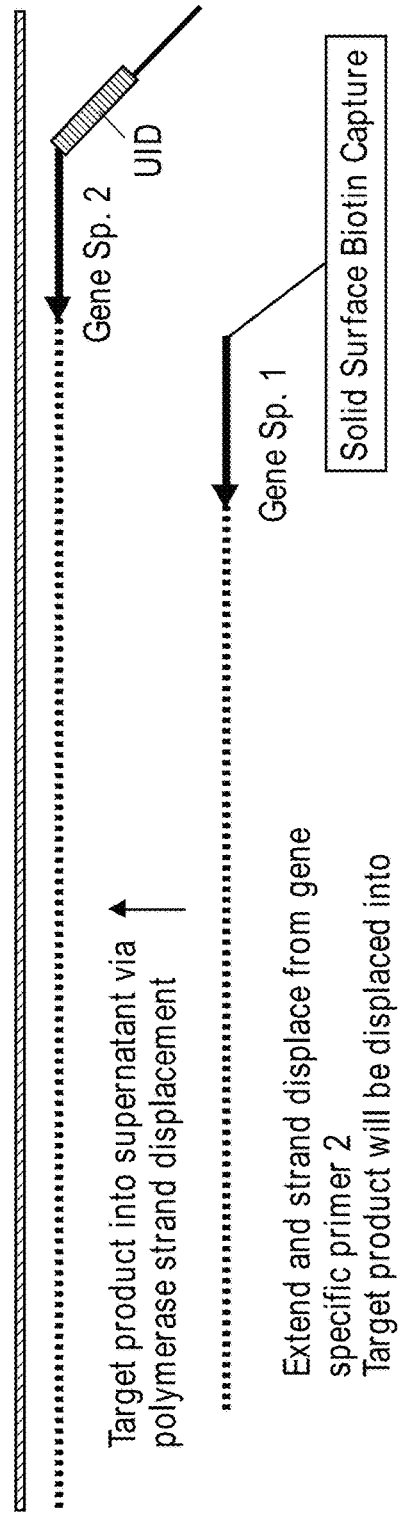

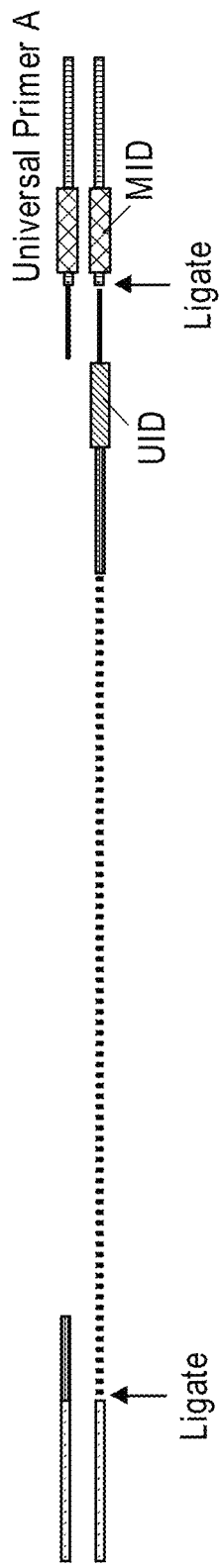
FIG. 1D Ligate universal adapters to ends of target
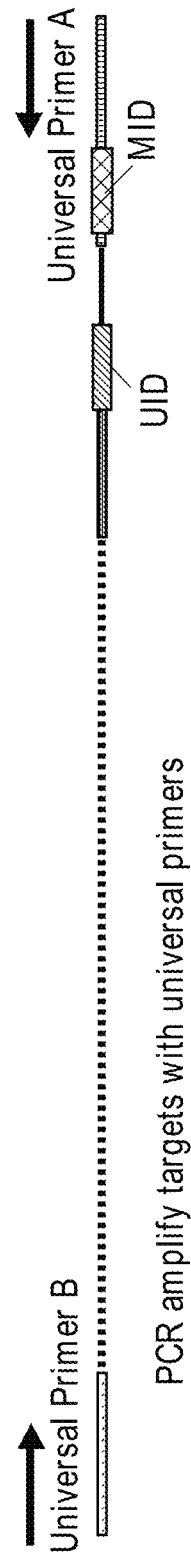
FIG. 1E PCR amplify targets with universal primers

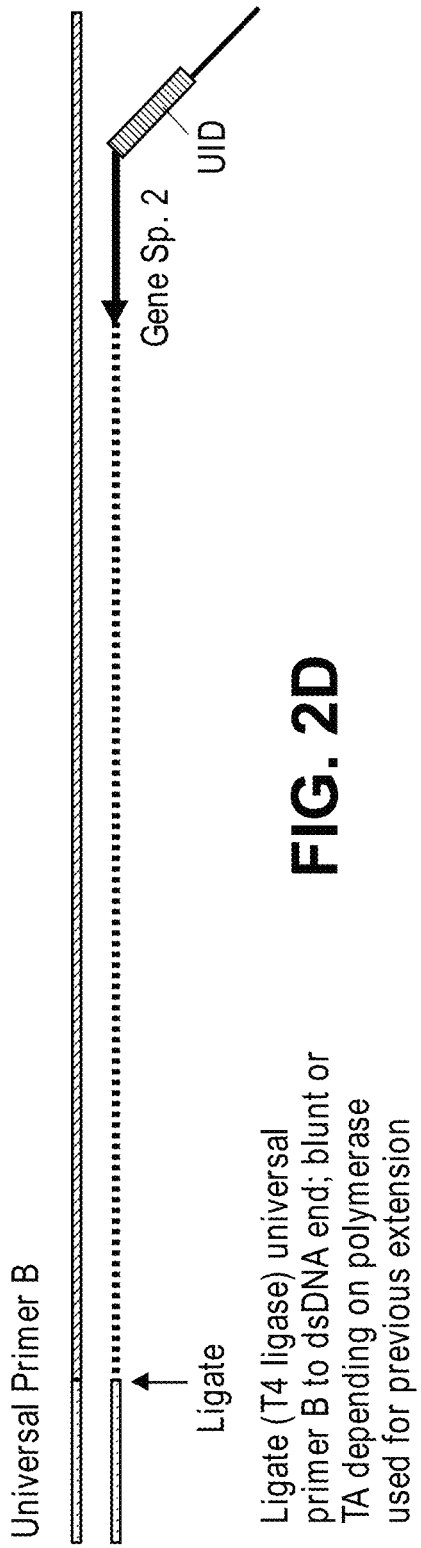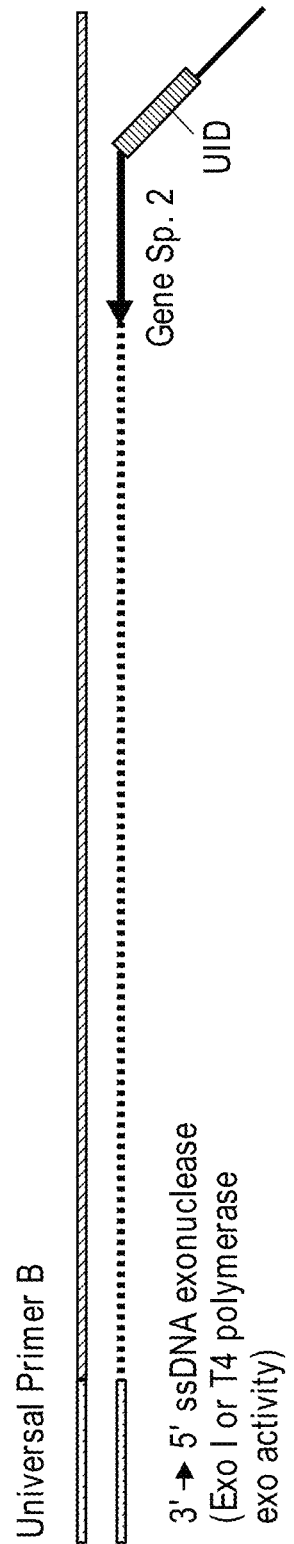

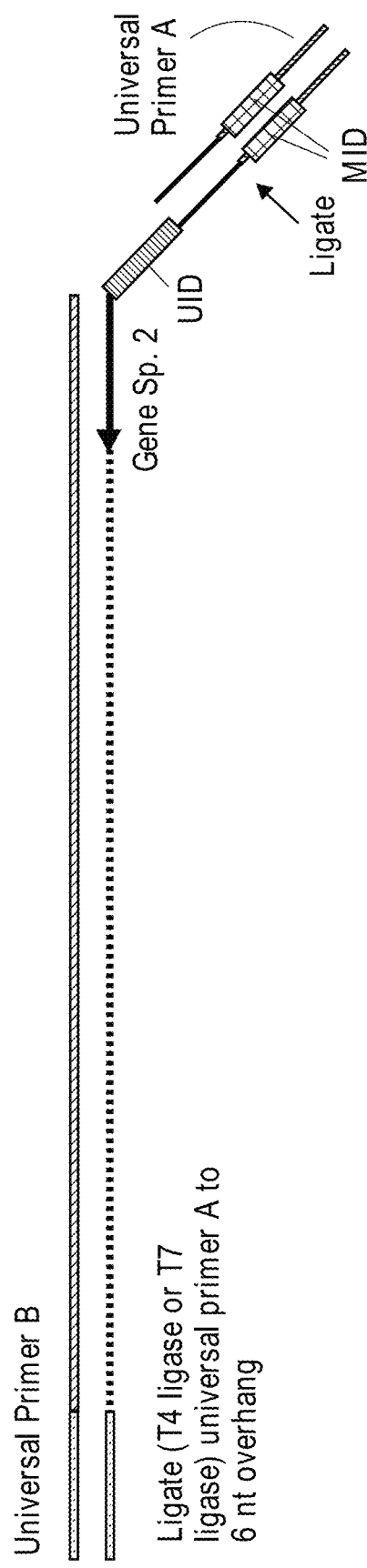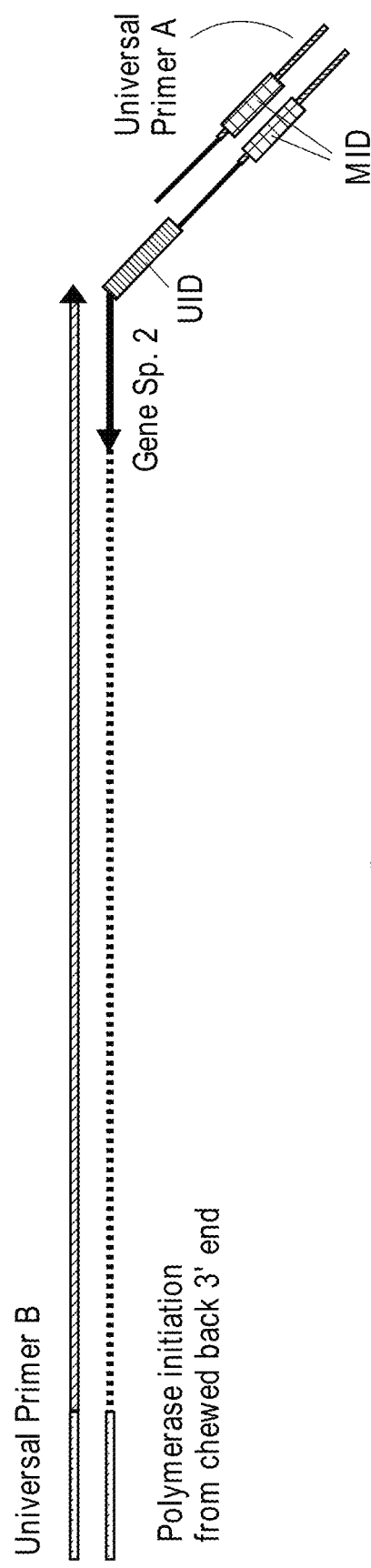
FIG. 3A
FIG. 3B

SEQUENCE LISTING

<160> NUMBER OF SEQ ID NOS: 262

<210> SEQ ID NO 1
<211> LENGTH: 71
<212> TYPE: DNA
<213> ORGANISM: Artificial Sequence
<220> FEATURE:
<223> OTHER INFORMATION: synthetic nucleotide construct

<400> SEQUENCE: 1
aatgatacgg cgaccaccga gatctacact agatcgctcg tcggcagcgt cagatgtgta    60
taagagacag t                                                          71

<210> SEQ ID NO 2
<211> LENGTH: 33
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' phosporylation (5Phos)

<400> SEQUENCE: 2
ctgtctctta tacacatctg acgctgccga cga                                  33

<210> SEQ ID NO 3
<211> LENGTH: 20
<212> TYPE: DNA
<213> ORGANISM: Artificial Sequence
<220> FEATURE:
<223> OTHER INFORMATION: synthetic nucleotide construct

<400> SEQUENCE: 3
aatgatacgg cgaccaccga                                                 20

<210> SEQ ID NO 4

```
<211> LENGTH: 58
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (24)..(25)
<223> OTHER INFORMATION: 3' end of position 24 (T) conjugated with index
      sequence to 5' end of positin 25 (G)

<400> SEQUENCE: 4
caagcagaag acggcatacg agatgtctcg tgggctcgga gatgtgtata agagacag       58

<210> SEQ ID NO 5
<211> LENGTH: 58
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (24)..(25)
<223> OTHER INFORMATION: 3' end of position 24 (T) conjugated with index
      sequence to 5' end of positin 25 (G)

<400> SEQUENCE: 5
caagcagaag acggcatacg agatgtctcg tgggctcgga gatgtgtata agagacag       58

<210> SEQ ID NO 6
<211> LENGTH: 20
<212> TYPE: DNA
<213> ORGANISM: Artificial Sequence
<220> FEATURE:
<223> OTHER INFORMATION: synthetic nucleotide construct

<400> SEQUENCE: 6
aatgatacgg cgaccaccga                                                 20

<210> SEQ ID NO 7
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 7
tgaaagctgt accatacctg t                                               21

<210> SEQ ID NO 8
<211> LENGTH: 24
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 8
aggttaatat ccgcaaatga cttg                                            24

<210> SEQ ID NO 9
<211> LENGTH: 21
```

```
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 9
agatgatccg acaagtgaga g                                              21

<210> SEQ ID NO 10
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 10
tacgtctcct ccgaccac                                                  18

<210> SEQ ID NO 11
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 11
cgcagcctgt acccagtg                                                  18

<210> SEQ ID NO 12
<211> LENGTH: 22
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 12
gcggaagatg aagatttcgg at                                             22

<210> SEQ ID NO 13
<211> LENGTH: 25
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 13
gttagctcat ttttgttaat ggtgg                                          25

<210> SEQ ID NO 14
```

```
<211> LENGTH: 26
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 14
ttaaactttt cttttagttg tgctga                                              26

<210> SEQ ID NO 15
<211> LENGTH: 27
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 15
gtatgcaaca tttctaaagt tacctac                                             27

<210> SEQ ID NO 16
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 16
aagaccataa cccaccacag                                                     20

<210> SEQ ID NO 17
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 17
ctggaaaggg acgaactggt                                                     20

<210> SEQ ID NO 18
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 18
cgacccagtt accatagcaa                                                     20
```

```
<210> SEQ ID NO 19
<211> LENGTH: 26
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 19
agaaaatgga agtctatgtg atcaag                                          26

<210> SEQ ID NO 20
<211> LENGTH: 29
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 20
cattttaaat tttctttctc taggtgaag                                       29

<210> SEQ ID NO 21
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 21
ggtcttggcc gaggtctc                                                   18

<210> SEQ ID NO 22
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 22
cagcaccatg ggcacgtc                                                   18

<210> SEQ ID NO 23
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 23
gagaggtgga aagcgagag                                                  19
```

<210> SEQ ID NO 24
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 24
cactcttgcc cacaccgc                                                 18

<210> SEQ ID NO 25
<211> LENGTH: 28
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 25
ctgtatttat ttcagtgtta cttacctg                                      28

<210> SEQ ID NO 26
<211> LENGTH: 30
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 26
ttatattcaa tttaaaccca cctataatgg                                    30

<210> SEQ ID NO 27
<211> LENGTH: 22
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 27
gtatcaaaga atggtcctgc ac                                            22

<210> SEQ ID NO 28
<211> LENGTH: 23
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 28
acacaacaca aaatagccgt ata                                           23

```
<210> SEQ ID NO 29
<211> LENGTH: 25
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 29 tctattctttt cctttgtagt gtcca                                    25

<210> SEQ ID NO 30
<211> LENGTH: 27
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 30
tgatttctgt ttttacctcc taaagaa                                   27

<210> SEQ ID NO 31
<211> LENGTH: 30
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 31
atctttaaag agaaatttgc taaagctgtg                                30

<210> SEQ ID NO 32
<211> LENGTH: 23
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 32
acgtgttttg atcaaagaag agg                                       23

<210> SEQ ID NO 33
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 33
```
agcctcacgt tggtccac                                                 18

<210> SEQ ID NO 34
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 34
ggatggctag gcgaggag                                                 18

<210> SEQ ID NO 35
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 35
agggactagg cgtgggat                                                 18

<210> SEQ ID NO 36
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 36
ccaagcccta gggtggtg                                                 18

<210> SEQ ID NO 37
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 37
acgctcttct cactcatatc c                                             21

<210> SEQ ID NO 38
<211> LENGTH: 25
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 38
aagaaatctt agacgtaagc ccctc                                        25

<210> SEQ ID NO 39
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 39
tcccataccc tctcagcg                                                18

<210> SEQ ID NO 40
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 40
ggatgagcta cctggaggat                                              20

<210> SEQ ID NO 41
<211> LENGTH: 24
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 41
attttgagtg ttagactgga aact                                         24

<210> SEQ ID NO 42
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 42
gggcagtgct aggaaagag                                               19

<210> SEQ ID NO 43
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

```
<400> SEQUENCE: 43
tgcttacctc gcttagtgc                                                19

<210> SEQ ID NO 44
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 44
gccggggatg tgatgaga                                                 18

<210> SEQ ID NO 45
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 45
caggggtcag aggcaagc                                                 18

<210> SEQ ID NO 46
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 46
agggccactg acaaccac                                                 18

<210> SEQ ID NO 47
<211> LENGTH: 23
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 47
tgtttctgtc atccaaatac tcc                                           23

<210> SEQ ID NO 48
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)
```

<400> SEQUENCE: 48
agtgaggaat cagaggcct                                          19

<210> SEQ ID NO 49
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 49
gtgctgtgac tgcttgtaga                                         20

<210> SEQ ID NO 50
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 50
acggccaggc attgaagt                                           18

<210> SEQ ID NO 51
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 51
aaaccgtagc tgccctgg                                           18

<210> SEQ ID NO 52
<211> LENGTH: 24
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 52
tcaaaattgc ttcagaaatt ggag                                    24

<210> SEQ ID NO 53
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)

```
<223> OTHER INFORMATION: 5' biotin modification (5Biosg)

<400> SEQUENCE: 53
acaaggtgga gagagtgaaa c                                          21

<210> SEQ ID NO 54
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 54
gccatcgttg tccactgaa                                             19

<210> SEQ ID NO 55
<211> LENGTH: 22
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 55
tggtgttcca ttgcttactt tg                                         22

<210> SEQ ID NO 56
<211> LENGTH: 24
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 56
gcagagaagt tatatgctga ggag                                       24

<210> SEQ ID NO 57
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 57
ctgctgctgg aattggtgt                                             19

<210> SEQ ID NO 58
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
```

```
<222> LOCATION: (1)..(1)
<223> OTHER INFORMATION: 5' biotin modification (5Biosg)

<400> SEQUENCE: 58
tcaaagaaac accttgctgg a                                        21

<210> SEQ ID NO 59
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 59
caccgcatcg actccacc                                            18

<210> SEQ ID NO 60
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 60
cagctggttc cggaagaaa                                           19

<210> SEQ ID NO 61
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 61
tgcagattgg gccttggg                                            18

<210> SEQ ID NO 62
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 62
tggaaatttc tgggccatga                                          20

<210> SEQ ID NO 63
<211> LENGTH: 25
<212> TYPE: DNA
<213> ORGANISM: Artificial Sequence
<220> FEATURE:
<223> OTHER INFORMATION: synthetic nucleotide construct
<220> FEATURE:
```

<221> NAME/KEY: modified_base
<222> LOCATION: (1)..(1)
<223> OTHER INFORMATION: 5' biotin modification (5Biosg)

<400> SEQUENCE: 63
acagagaaat gttgtacaga ttgag         25

<210> SEQ ID NO 64
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 64
tcaatagtgc agatgggagg         20

<210> SEQ ID NO 65
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 65
gcgggtctct cggaggaa         18

<210> SEQ ID NO 66
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 66
agaagcaaga aaatacccccc t         21

<210> SEQ ID NO 67
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 67
cgactttgtg accttcggc         19

<210> SEQ ID NO 68
<211> LENGTH: 23
<212> TYPE: DNA
<213> ORGANISM: Artificial Sequence
<220> FEATURE:
<223> OTHER INFORMATION: synthetic nucleotide construct

```
<220> FEATURE:
<221> NAME/KEY: modified_base
<222> LOCATION: (1)..(1)
<223> OTHER INFORMATION: 5' biotin modification (5Biosg)

<400> SEQUENCE: 68
ccaatggact gttttacaat gcc                                              23

<210> SEQ ID NO 69
<211> LENGTH: 30
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 69
ttattttatt ttacagagta acagactagc                                       30

<210> SEQ ID NO 70
<211> LENGTH: 27
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 70
ccaaactgac caaactgttc ttattac                                          27

<210> SEQ ID NO 71
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 71
tgatgcttgg ctctggaat                                                   19

<210> SEQ ID NO 72
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 72
cgaaagaccc tagccttaga t                                                21

<210> SEQ ID NO 73
<211> LENGTH: 27
<212> TYPE: DNA
<213> ORGANISM: Artificial Sequence
<220> FEATURE:
```

<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 73
gtttcgtatt tatagctgat ttgatgg                                   27

<210> SEQ ID NO 74
<211> LENGTH: 28
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 74
ccttatgatt catcaggaga gcatttaa                                  28

<210> SEQ ID NO 75
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 75
tctggatccc acacctttac                                           20

<210> SEQ ID NO 76
<211> LENGTH: 25
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 76
gctatggctt tcctagaata gaaac                                     25

<210> SEQ ID NO 77
<211> LENGTH: 24
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 77
tttttcatga agatgcatac aacg                                      24

<210> SEQ ID NO 78
<211> LENGTH: 30
<212> TYPE: DNA
<213> ORGANISM: Artificial Sequence

```
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 78
gaagaatgta attgataatc tttacctctt                                          30

<210> SEQ ID NO 79
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 79
gctgctcgca acgtcctc                                                       18

<210> SEQ ID NO 80
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 80
cgtttggaaa gctagtggtt c                                                   21

<210> SEQ ID NO 81
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 81
tctccagagt gctctaatga c                                                   21

<210> SEQ ID NO 82
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 82
ccatcaccac ttaccttgtt g                                                   21

<210> SEQ ID NO 83
<211> LENGTH: 18
<212> TYPE: DNA
```

```
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 83
cagagacttg gcagccag                                                     18

<210> SEQ ID NO 84
<211> LENGTH: 24
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 84
agaaatatcc tccttactca tggt                                              24

<210> SEQ ID NO 85
<211> LENGTH: 29
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 85
gcttttactg attaacgtaa atacaagat                                         29

<210> SEQ ID NO 86
<211> LENGTH: 26
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 86
cttttaagtg gtagccatag tatgat                                            26

<210> SEQ ID NO 87
<211> LENGTH: 22
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 87
ttcagcaaat cgaaaggac at                                                 22

<210> SEQ ID NO 88
<211> LENGTH: 28
```

```
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 88
aattgtttat catacagaca cttcattt                                          28

<210> SEQ ID NO 89
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 89
tcaactacac gaatggacca                                                   20

<210> SEQ ID NO 90
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 90
tgaggaattt gtcttggcga g                                                 21

<210> SEQ ID NO 91
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 91
ccaaggcatc tcatcgtagt a                                                 21

<210> SEQ ID NO 92
<211> LENGTH: 25
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 92
gtcagacaat tttaatactg gcaac                                             25

<210> SEQ ID NO 93
```

```
<211> LENGTH: 26
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 93
gttctgaaaa agatagaagt ttggag                                          26

<210> SEQ ID NO 94
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 94
ttgcagatct ccaccactg                                                  19

<210> SEQ ID NO 95
<211> LENGTH: 24
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 95
ggtctaccac tgaattacat tgtg                                            24

<210> SEQ ID NO 96
<211> LENGTH: 29
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 96
cggaaaattc aaataggaca tgttctatg                                       29

<210> SEQ ID NO 97
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 97
gaatgaaaga tgggcaagac c                                               21
```

```
<210> SEQ ID NO 98
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 98
cacattttgg acagcaggaa t                                              21

<210> SEQ ID NO 99
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 99
aggcagaatc agctccatcc                                                20

<210> SEQ ID NO 100
<211> LENGTH: 28
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 100
gacttattgt gtagaagata ctccaata                                       28

<210> SEQ ID NO 101
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 101
tcagacgaca caggaagc                                                  18

<210> SEQ ID NO 102
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 102
agcaccctag aaccaaatcc                                                20
```

```
<210> SEQ ID NO 103
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 103
cgaaatctcc ctccaaaagt g                                              21

<210> SEQ ID NO 104
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 104
tgagagtcgt tcgattgcca                                                20

<210> SEQ ID NO 105
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 105
gacaaaccat gccaccaag                                                 19

<210> SEQ ID NO 106
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 106
tgaaaagaga gagagtggac c                                              21

<210> SEQ ID NO 107
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 107
acggaaagta ctccagatgg                                                20
```

<210> SEQ ID NO 108
<211> LENGTH: 22
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 108
gttcaggaaa atgacaatgg ga                                    22

<210> SEQ ID NO 109
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 109
gtcctttctg taggctggat                                       20

<210> SEQ ID NO 110
<211> LENGTH: 22
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 110
cacaaaatgg atccagacaa ct                                    22

<210> SEQ ID NO 111
<211> LENGTH: 29
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 111
agttgttaaa catatcctat tatgacttg                             29

<210> SEQ ID NO 112
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 112
gtgagggctg aggtgacc					18

<210> SEQ ID NO 113
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 113
gccagttaac gtcttccttc t					21

<210> SEQ ID NO 114
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 114
ttctggccac catgcgaa					18

<210> SEQ ID NO 115
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 115
ctcacagcag ggtcttctc					19

<210> SEQ ID NO 116
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 116
tcaagatcac agattttggg c					21

<210> SEQ ID NO 117
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 117
cacgtgttga agtcctcgt                                    19

<210> SEQ ID NO 118
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 118
ctcccgggct gaactttc                                     18

<210> SEQ ID NO 119
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 119
tgcgggcatg gttactgc                                     18

<210> SEQ ID NO 120
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 120
cgatggccca gctcctca                                     18

<210> SEQ ID NO 121
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 121
cacgggtcgg gtgagagt                                     18

<210> SEQ ID NO 122
<211> LENGTH: 26
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 122 tttttttccttt agtctttctt tgaagc                                26

<210> SEQ ID NO 123
<211> LENGTH: 24
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification (5Biosg)

<400> SEQUENCE: 123
tcatattcac taagcgctac taga                                    24

<210> SEQ ID NO 124
<211> LENGTH: 67
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 124
gtctcgtggg ctcggagatg tgtataagag acagwnnnnn nwgttaatca actgatgcaa    60
actcttg                                                              67

<210> SEQ ID NO 125
<211> LENGTH: 67
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 125
gtctcgtggg ctcggagatg tgtataagag acagwnnnnn nwaaataatg ctcctagtac    60
ctgtaga                                                              67

<210> SEQ ID NO 126
<211> LENGTH: 70
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 126
gtctcgtggg ctcggagatg tgtataagag acagwnnnnn nwtcctttaa tacagaatat    60
gggtaaagat                                                           70

<210> SEQ ID NO 127
<211> LENGTH: 64
<212> TYPE: DNA
<213> ORGANISM: Artificial Sequence

```
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 127
gtctcgtggg ctcggagatg tgtataagag acagwnnnnn nwtgtaaacc ttgcagacaa    60
actc                                                                64

<210> SEQ ID NO 128
<211> LENGTH: 61
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 128
gtctcgtggg ctcggagatg tgtataagag acagwnnnnn nwccatgagg cagagcatac    60
g                                                                   61

<210> SEQ ID NO 129
<211> LENGTH: 61
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 129
gtctcgtggg ctcggagatg tgtataagag acagwnnnnn nwacatcctg gtagctgagg    60
g                                                                   61

<210> SEQ ID NO 130
<211> LENGTH: 72
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 130
gtctcgtggg ctcggagatg tgtataagag acagwnnnnn nwgtcttttg gttttcttg     60 atagtattaa tg                                                       72

<210> SEQ ID NO 131
<211> LENGTH: 67
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T
```

<400> SEQUENCE: 131
gtctcgtggg ctcggagatg tgtataagag acagwnnnnn nwttcttcct aagtgcaaaa    60
gataact                                                              67

<210> SEQ ID NO 132
<211> LENGTH: 72
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 132
gtctcgtggg ctcggagatg tgtataagag acagwnnnnn nwcagtgttt cttttaaata    60
cctgttaagt tt                                                        72

<210> SEQ ID NO 133
<211> LENGTH: 64
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 133
gtctcgtggg ctcggagatg tgtataagag acagwnnnnn nwccacagtt gcacaatatc    60
cttt                                                                 64

<210> SEQ ID NO 134
<211> LENGTH: 63
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 134
gtctcgtggg ctcggagatg tgtataagag acagwnnnnn nwtgcagcaa ttcactgtaa    60
agc                                                                  63

<210> SEQ ID NO 135
<211> LENGTH: 72
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 135
gtctcgtggg ctcggagatg tgtataagag acagwnnnnn nwctaatgta tatatgttct    60
taaatggcta cg                                                        72

-continued

```
<210> SEQ ID NO 136
<211> LENGTH: 61
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 136
gtctcgtggg ctcggagatg tgtataagag acagwnnnnn nwccaggacc agaggaaacc    60
t                                                                    61

<210> SEQ ID NO 137
<211> LENGTH: 71
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 137
gtctcgtggg ctcggagatg tgtataagag acagwnnnnn nwaaatagtt taagatgagt    60
catatttgtg g                                                         71

<210> SEQ ID NO 138
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 138
gtctcgtggg ctcggagatg tgtataagag acagwnnnnn nwctgtgggg tggagagctg    60

<210> SEQ ID NO 139
<211> LENGTH: 61
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 139
gtctcgtggg ctcggagatg tgtataagag acagwnnnnn nwggtcacac ttgttcccca    60
c                                                                    61

<210> SEQ ID NO 140
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
```

<223> OTHER INFORMATION: N is A, C, G, or T

<400> SEQUENCE: 140
gtctcgtggg ctcggagatg tgtataagag acagwnnnnn nwccgtttga tctgctccct    60

<210> SEQ ID NO 141
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 141
gtctcgtggg ctcggagatg tgtataagag acagwnnnnn nwctggatgg tcagcgcact    60

<210> SEQ ID NO 142
<211> LENGTH: 68
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 142
gtctcgtggg ctcggagatg tgtataagag acagwnnnnn nwgttatgat tttgcagaaa    60
acagatct                                                             68

<210> SEQ ID NO 143
<211> LENGTH: 71
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 143
gtctcgtggg ctcggagatg tgtataagag acagwnnnnn nwactataat tactccttaa    60
tgtcagctta t                                                         71

<210> SEQ ID NO 144
<211> LENGTH: 68
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 144
gtctcgtggg ctcggagatg tgtataagag acagwnnnnn nwtgaaaatg gtcagagaaa    60
cctttatc                                                             68

<210> SEQ ID NO 145
<211> LENGTH: 65

```
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 145
gtctcgtggg ctcggagatg tgtataagag acagwnnnnn nwtgcagttg tttaccatga    60
taacg                                                                65

<210> SEQ ID NO 146
<211> LENGTH: 72
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 146
gtctcgtggg ctcggagatg tgtataagag acagwnnnnn nwcgaaataa cacaaatttt    60
taaggttact ga                                                        72

<210> SEQ ID NO 147
<211> LENGTH: 65
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 147
gtctcgtggg ctcggagatg tgtataagag acagwnnnnn nwtgattaca cagtatcctc    60
gacat                                                                65

<210> SEQ ID NO 148
<211> LENGTH: 69
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 148
gtctcgtggg ctcggagatg tgtataagag acagwnnnnn nwctgaaaag agtgaaggat    60
ataggatac                                                            69

<210> SEQ ID NO 149
<211> LENGTH: 64
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
```

<223> OTHER INFORMATION: N is A, C, G, or T

<400> SEQUENCE: 149
gtctcgtggg ctcggagatg tgtataagag acagwnnnnn nwactgttct tcctcagaca    60
ttca    64

<210> SEQ ID NO 150
<211> LENGTH: 63
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 150
gtctcgtggg ctcggagatg tgtataagag acagwnnnnn nwccacagag aagttgttga    60
ggg    63

<210> SEQ ID NO 151
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 151
gtctcgtggg ctcggagatg tgtataagag acagwnnnnn nwgccttgta ctgcagagac    60
aa    62

<210> SEQ ID NO 152
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 152
gtctcgtggg ctcggagatg tgtataagag acagwnnnnn nwtggtgatg ggcttggtcc    60

<210> SEQ ID NO 153
<211> LENGTH: 61
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 153
gtctcgtggg ctcggagatg tgtataagag acagwnnnnn nwtacagcgg agaagggagc    60
g    61

```
<210> SEQ ID NO 154
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 154
gtctcgtggg ctcggagatg tgtataagag acagwnnnnn nwcaggtagg atccagccca    60

<210> SEQ ID NO 155
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 155
gtctcgtggg ctcggagatg tgtataagag acagwnnnnn nwatccccca aagccaacaa    60

<210> SEQ ID NO 156
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 156
gtctcgtggg ctcggagatg tgtataagag acagwnnnnn nwgtttgggg gtgtgtggtc    60

<210> SEQ ID NO 157
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 157
gtctcgtggg ctcggagatg tgtataagag acagwnnnnn nwggtgcttc ccattccagg    60

<210> SEQ ID NO 158
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 158
gtctcgtggg ctcggagatg tgtataagag acagwnnnnn nwacagtcaa gaagaaaacg    60
```

```
gc                                                              62

<210> SEQ ID NO 159
<211> LENGTH: 61
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 159
gtctcgtggg ctcggagatg tgtataagag acagwnnnnn nwagaggagc tggtgttgtt    60
g                                                               61

<210> SEQ ID NO 160
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 160
gtctcgtggg ctcggagatg tgtataagag acagwnnnnn nwaccgcttc ttgtcctgct    60

<210> SEQ ID NO 161
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 161
gtctcgtggg ctcggagatg tgtataagag acagwnnnnn nwgagcagta aggagattcc    60
cc                                                              62

<210> SEQ ID NO 162
<211> LENGTH: 61
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 162
gtctcgtggg ctcggagatg tgtataagag acagwnnnnn nwaaatcggt aagaggtggg    60
c                                                               61

<210> SEQ ID NO 163
<211> LENGTH: 60
<212> TYPE: DNA
<213> ORGANISM: Artificial Sequence
<220> FEATURE:
<223> OTHER INFORMATION: synthetic nucleotide construct
```

```
<220> FEATURE:
<221> NAME/KEY: misc_feature
<222> LOCATION: (36)..(41)
<223> OTHER INFORMATION: N is A, C, G, or T

<400> SEQUENCE: 163
gtctcgtggg ctcggagatg tgtataagag acagwnnnnn nwcccccctac tgctcacctg     60

<210> SEQ ID NO 164
<211> LENGTH: 63
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 164
gtctcgtggg ctcggagatg tgtataagag acagwnnnnn nwccaccaca ctatgtcgaa     60
aag                                                                   63

<210> SEQ ID NO 165
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 165
gtctcgtggg ctcggagatg tgtataagag acagwnnnnn nwggccagac ctaagagcaa     60
tc                                                                    62

<210> SEQ ID NO 166
<211> LENGTH: 61
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 166
gtctcgtggg ctcggagatg tgtataagag acagwnnnnn nwgcctcaca acctccgtca     60
t                                                                     61

<210> SEQ ID NO 167
<211> LENGTH: 63
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 167
gtctcgtggg ctcggagatg tgtataagag acagwnnnnn nwacaaaaga aatgcagggg     60
```

```
gat                                                                63
```

```
<210> SEQ ID NO 168
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 168
gtctcgtggg ctcggagatg tgtataagag acagwnnnnn nwgcaagaag cccagacgga    60
```

```
<210> SEQ ID NO 169
<211> LENGTH: 65
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 169
gtctcgtggg ctcggagatg tgtataagag acagwnnnnn nwtttcactg tttccaaagg    60
atcaa                                                                65
```

```
<210> SEQ ID NO 170
<211> LENGTH: 64
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 170
gtctcgtggg ctcggagatg tgtataagag acagwnnnnn nwtgcatagt ttgatgtgcc    60
atag                                                                 64
```

```
<210> SEQ ID NO 171
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 171
gtctcgtggg ctcggagatg tgtataagag acagwnnnnn nwtgcatgac tttgagggac    60
ag                                                                   62
```

```
<210> SEQ ID NO 172
<211> LENGTH: 69
<212> TYPE: DNA
<213> ORGANISM: Artificial Sequence
<220> FEATURE:
<223> OTHER INFORMATION: synthetic nucleotide construct
```

```
<220> FEATURE:
<221> NAME/KEY: misc_feature
<222> LOCATION: (36)..(41)
<223> OTHER INFORMATION: N is A, C, G, or T

<400> SEQUENCE: 172
gtctcgtggg ctcggagatg tgtataagag acagwnnnnn nwcatttatt tcctatagct    60
cctgagtat                                                           69

<210> SEQ ID NO 173
<211> LENGTH: 64
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 173
gtctcgtggg ctcggagatg tgtataagag acagwnnnnn nwtgttactt cttggcactt    60
tagc                                                                64

<210> SEQ ID NO 174
<211> LENGTH: 64
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 174
gtctcgtggg ctcggagatg tgtataagag acagwnnnnn nwcttttctg ttaggtctgt    60
cagc                                                                64

<210> SEQ ID NO 175
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 175
gtctcgtggg ctcggagatg tgtataagag acagwnnnnn nwggattacc caagacagag    60
ca                                                                  62

<210> SEQ ID NO 176
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 176
```

```
gtctcgtggg ctcggagatg tgtataagag acagwnnnnn nwgggtatgg acacgttcat    60
cc                                                                   62
```

```
<210> SEQ ID NO 177
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 177
gtctcgtggg ctcggagatg tgtataagag acagwnnnnn nwactgcttc tgggcgtttg    60
```

```
<210> SEQ ID NO 178
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 178
gtctcgtggg ctcggagatg tgtataagag acagwnnnnn nwgagccgtc ctgggattgc    60
```

```
<210> SEQ ID NO 179
<211> LENGTH: 70
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 179
gtctcgtggg ctcggagatg tgtataagag acagwnnnnn nwagataaga ataaaacaca    60
tacaagttgg                                                           70
```

```
<210> SEQ ID NO 180
<211> LENGTH: 69
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 180
gtctcgtggg ctcggagatg tgtataagag acagwnnnnn nwtgttttg aactgtcgta     60 tttttcaat                                                            69
```

```
<210> SEQ ID NO 181
<211> LENGTH: 63
<212> TYPE: DNA
<213> ORGANISM: Artificial Sequence
<220> FEATURE:
<223> OTHER INFORMATION: synthetic nucleotide construct
```

```
<220> FEATURE:
<221> NAME/KEY: misc_feature
<222> LOCATION: (36)..(41)
<223> OTHER INFORMATION: N is A, C, G, or T

<400> SEQUENCE: 181
gtctcgtggg ctcggagatg tgtataagag acagwnnnnn nwttgaccat gaccatgtaa       60
acg                                                                    63

<210> SEQ ID NO 182
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 182
gtctcgtggg ctcggagatg tgtataagag acagwnnnnn nwtctcactc accgggcgag       60

<210> SEQ ID NO 183
<211> LENGTH: 72
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 183
gtctcgtggg ctcggagatg tgtataagag acagwnnnnn nwctacatta ataaccataa       60
agcatgaact at                                                          72

<210> SEQ ID NO 184
<211> LENGTH: 69
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 184
gtctcgtggg ctcggagatg tgtataagag acagwnnnnn nwggaagaat tttttgatga       60
aacaagacg                                                              69

<210> SEQ ID NO 185
<211> LENGTH: 63
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 185
gtctcgtggg ctcggagatg tgtataagag acagwnnnnn nwaagcctttt attctcaact     60
```

```
gcc                                                                     63

<210> SEQ ID NO 186
<211> LENGTH: 72
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 186
gtctcgtggg ctcggagatg tgtataagag acagwnnnnn nwgggaaaaa tatgacaaag       60
aaagctatat aa                                                          72

<210> SEQ ID NO 187
<211> LENGTH: 68
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 187
gtctcgtggg ctcggagatg tgtataagag acagwnnnnn nwcctgaagg tattaacatc       60
atttgctc                                                               68

<210> SEQ ID NO 188
<211> LENGTH: 71
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 188
gtctcgtggg ctcggagatg tgtataagag acagwnnnnn nwccaatctc ttcataaatc       60
ttttctcaat g                                                           71

<210> SEQ ID NO 189
<211> LENGTH: 66
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 189
gtctcgtggg ctcggagatg tgtataagag acagwnnnnn nwttttgatg acattgcata       60
cattcg                                                                 66

<210> SEQ ID NO 190
<211> LENGTH: 72
<212> TYPE: DNA
<213> ORGANISM: Artificial Sequence
```

```
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 190
gtctcgtggg ctcggagatg tgtataagag acagwnnnnn nwgtaacatt tccaatctac      60
taatgctaat ac                                                         72

<210> SEQ ID NO 191
<211> LENGTH: 68
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 191
gtctcgtggg ctcggagatg tgtataagag acagwnnnnn nwgacagtga ttatctgagt      60
aaaacaac                                                              68

<210> SEQ ID NO 192
<211> LENGTH: 64
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 192
gtctcgtggg ctcggagatg tgtataagag acagwnnnnn nwcgtgtgta gacaggtttc      60
agtc                                                                  64

<210> SEQ ID NO 193
<211> LENGTH: 65
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 193
gtctcgtggg ctcggagatg tgtataagag acagwnnnnn nwcaccaatt ttaagacaaa      60
acgct                                                                 65

<210> SEQ ID NO 194
<211> LENGTH: 65
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T
```

<400> SEQUENCE: 194
gtctcgtggg ctcggagatg tgtataagag acagwnnnnn nwccatgaca agattttccc    60
ttacc    65

<210> SEQ ID NO 195
<211> LENGTH: 72
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 195
gtctcgtggg ctcggagatg tgtataagag acagwnnnnn nwgttatata ttcaaataac    60
acccaatgaa ga    72

<210> SEQ ID NO 196
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 196
gtctcgtggg ctcggagatg tgtataagag acagwnnnnn nwtgtgtcca ccgtgatctg    60

<210> SEQ ID NO 197
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 197
gtctcgtggg ctcggagatg tgtataagag acagwnnnnn nwactaaact catctgggcc    60
ac    62

<210> SEQ ID NO 198
<211> LENGTH: 71
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 198
gtctcgtggg ctcggagatg tgtataagag acagwnnnnn nwacctacaa atatttacag    60
gtaaccattt a    71

<210> SEQ ID NO 199
<211> LENGTH: 61

```
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 199
gtctcgtggg ctcggagatg tgtataagag acagwnnnnn nwttcaattc caccaccagc    60
a                                                                   61

<210> SEQ ID NO 200
<211> LENGTH: 67
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 200
gtctcgtggg ctcggagatg tgtataagag acagwnnnnn nwtctcctcc aacctaatag    60
tgtattc                                                             67

<210> SEQ ID NO 201
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 201
gtctcgtggg ctcggagatg tgtataagag acagwnnnnn nwcacagaga cttggcagcc    60

<210> SEQ ID NO 202
<211> LENGTH: 67
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 202
gtctcgtggg ctcggagatg tgtataagag acagwnnnnn nwttggttct tatatgcttt    60
tttgctt                                                             67

<210> SEQ ID NO 203
<211> LENGTH: 66
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T
```

<400> SEQUENCE: 203
gtctcgtggg ctcggagatg tgtataagag acagwnnnnn nwgagaatga tttgacataa    60
ccctga    66

<210> SEQ ID NO 204
<211> LENGTH: 66
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 204
gtctcgtggg ctcggagatg tgtataagag acagwnnnnn nwattttagc gaagaatagc    60
cagaat    66

<210> SEQ ID NO 205
<211> LENGTH: 72
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 205
gtctcgtggg ctcggagatg tgtataagag acagwnnnnn nwtgaacagt tataatggtc    60
atacttttat ga    72

<210> SEQ ID NO 206
<211> LENGTH: 70
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 206
gtctcgtggg ctcggagatg tgtataagag acagwnnnnn nwccatctat aatgtgctta    60
atttttaggg    70

<210> SEQ ID NO 207
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 207
gtctcgtggg ctcggagatg tgtataagag acagwnnnnn nwgcaggtta ttgcgagtgt    60
tt    62

```
<210> SEQ ID NO 208
<211> LENGTH: 69
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 208
gtctcgtggg ctcggagatg tgtataagag acagwnnnnn nwttgacaat atagacaatt    60
taagtccca                                                             69

<210> SEQ ID NO 209
<211> LENGTH: 67
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 209
gtctcgtggg ctcggagatg tgtataagag acagwnnnnn nwcaccaatc gacatgatga    60
taatagg                                                               67

<210> SEQ ID NO 210
<211> LENGTH: 65
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 210
gtctcgtggg ctcggagatg tgtataagag acagwnnnnn nwagaggaag cttagatagt    60
tctcg                                                                 65

<210> SEQ ID NO 211
<211> LENGTH: 63
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 211
gtctcgtggg ctcggagatg tgtataagag acagwnnnnn nwgaacttct tcaaagcgag    60
gtt                                                                   63

<210> SEQ ID NO 212
<211> LENGTH: 64
<212> TYPE: DNA
<213> ORGANISM: Artificial Sequence
<220> FEATURE:
<223> OTHER INFORMATION: synthetic nucleotide construct
<220> FEATURE:
```

```
<221> NAME/KEY: misc_feature
<222> LOCATION: (36)..(41)
<223> OTHER INFORMATION: N is A, C, G, or T

<400> SEQUENCE: 212
gtctcgtggg ctcggagatg tgtataagag acagwnnnnn nwgccattca tacctctcag    60
gaag                                                                 64

<210> SEQ ID NO 213
<211> LENGTH: 68
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 213
gtctcgtggg ctcggagatg tgtataagag acagwnnnnn nwcaaacact tacaatttca    60
ctaagtcg                                                             68

<210> SEQ ID NO 214
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 214
gtctcgtggg ctcggagatg tgtataagag acagwnnnnn nwaggcaaag tccttcacag    60
aa                                                                   62

<210> SEQ ID NO 215
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 215
gtctcgtggg ctcggagatg tgtataagag acagwnnnnn nwcacctcaa gttccaacca    60
ca                                                                   62

<210> SEQ ID NO 216
<211> LENGTH: 64
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 216
gtctcgtggg ctcggagatg tgtataagag acagwnnnnn nwcacacctt catctaatgc    60
``` caag 64

```
<210> SEQ ID NO 217
<211> LENGTH: 70
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 217
```
gtctcgtggg ctcggagatg tgtataagag acagwnnnnn nwcttctatt aaccaagaaa   60
caatacagac   70

```
<210> SEQ ID NO 218
<211> LENGTH: 69
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 218
```
gtctcgtggg ctcggagatg tgtataagag acagwnnnnn nwcagctgaa gatgaaatag   60
gatgtaatc   69

```
<210> SEQ ID NO 219
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 219
```
gtctcgtggg ctcggagatg tgtataagag acagwnnnnn nwcgaagttc cagcagtgtc   60
ac   62

```
<210> SEQ ID NO 220
<211> LENGTH: 64
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 220
```
gtctcgtggg ctcggagatg tgtataagag acagwnnnnn nwtgttgaat tttcttcagg   60
agcg   64

```
<210> SEQ ID NO 221
<211> LENGTH: 66
<212> TYPE: DNA
```

<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 221
gtctcgtggg ctcggagatg tgtataagag acagwnnnnn nwcttctgtc agttcacttg    60
atagtt                                                                66

<210> SEQ ID NO 222
<211> LENGTH: 63
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 222
gtctcgtggg ctcggagatg tgtataagag acagwnnnnn nwgtgatctt ccagatagcc    60
ctg                                                                   63

<210> SEQ ID NO 223
<211> LENGTH: 68
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 223
gtctcgtggg ctcggagatg tgtataagag acagwnnnnn nwagtaccta aaataaagc    60 acctactg                                                              68

<210> SEQ ID NO 224
<211> LENGTH: 67
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 224
gtctcgtggg ctcggagatg tgtataagag acagwnnnnn nwtgatactt tattacattt    60
tgccacg                                                               67

<210> SEQ ID NO 225
<211> LENGTH: 67
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 225
gtctcgtggg ctcggagatg tgtataagag acagwnnnnn nwaattaaga ataatgcctc    60
cagttca                                                              67

<210> SEQ ID NO 226
<211> LENGTH: 65
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 226
gtctcgtggg ctcggagatg tgtataagag acagwnnnnn nwatttcagc cacgggtaat    60
aattt                                                                65

<210> SEQ ID NO 227
<211> LENGTH: 68
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 227
gtctcgtggg ctcggagatg tgtataagag acagwnnnnn nwgaaaaata gcctcaattc    60
ttaccatc                                                             68

<210> SEQ ID NO 228
<211> LENGTH: 71
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 228
gtctcgtggg ctcggagatg tgtataagag acagwnnnnn nwgaacagtg aatatttcct    60
ttgatgatat t                                                         71

<210> SEQ ID NO 229
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 229
gtctcgtggg ctcggagatg tgtataagag acagwnnnnn nwgtctggca ctgctttcca    60

<210> SEQ ID NO 230

```
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 230
gtctcgtggg ctcggagatg tgtataagag acagwnnnnn nwgtggcacc atctcacaat    60
tg                                                                  62

<210> SEQ ID NO 231
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 231
gtctcgtggg ctcggagatg tgtataagag acagwnnnnn nwggtccatg tgcccctcct    60

<210> SEQ ID NO 232
<211> LENGTH: 63
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 232
gtctcgtggg ctcggagatg tgtataagag acagwnnnnn nwtcttccca tgatgatctg    60
tcc                                                                 63

<210> SEQ ID NO 233
<211> LENGTH: 62
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 233
gtctcgtggg ctcggagatg tgtataagag acagwnnnnn nwggtgaaaa caccgcagca    60
tg                                                                  62

<210> SEQ ID NO 234
<211> LENGTH: 61
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T
```

<400> SEQUENCE: 234
gtctcgtggg ctcggagatg tgtataagag acagwnnnnn nwgtttgttc agttgggagc    60
g                                                                   61

<210> SEQ ID NO 235
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 235
gtctcgtggg ctcggagatg tgtataagag acagwnnnnn nwgcaagacc ggagactggt    60

<210> SEQ ID NO 236
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 236
gtctcgtggg ctcggagatg tgtataagag acagwnnnnn nwgaccttcc gcggcatcta    60

<210> SEQ ID NO 237
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 237
gtctcgtggg ctcggagatg tgtataagag acagwnnnnn nwcaggtacc gtgcgacatc    60

<210> SEQ ID NO 238
<211> LENGTH: 60
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 238
gtctcgtggg ctcggagatg tgtataagag acagwnnnnn nwcagcgtgt ccaggaagcc    60

<210> SEQ ID NO 239
<211> LENGTH: 71
<212> TYPE: DNA
<213> ORGANISM: Artificial Sequence
<220> FEATURE:
<223> OTHER INFORMATION: synthetic nucleotide construct
<220> FEATURE:

```
<221> NAME/KEY: misc_feature
<222> LOCATION: (36)..(41)
<223> OTHER INFORMATION: N is A, C, G, or T

<400> SEQUENCE: 239
gtctcgtggg ctcggagatg tgtataagag acagwnnnnn nwgacaacag tcaaacaaca    60
attctttgta c                                                        71

<210> SEQ ID NO 240
<211> LENGTH: 63
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(41)
<223> OTHER INFORMATION: N is A, C, G, or T

<400> SEQUENCE: 240
gtctcgtggg ctcggagatg tgtataagag acagwnnnnn nwtgactcca cgagaacttg    60
atc                                                                 63

<210> SEQ ID NO 241
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification linked to [18-carbon
      spacer (x3)] = /5Biosg//iSp18//iSp18//iSp18/

<400> SEQUENCE: 241
gggacggcct gagtctcc                                                 18

<210> SEQ ID NO 242
<211> LENGTH: 18
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification linked to [18-carbon
      spacer (x3)] = /5Biosg//iSp18//iSp18//iSp18/

<400> SEQUENCE: 242
ctgggtgtgc caggacag                                                 18

<210> SEQ ID NO 243
<211> LENGTH: 35
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification linked to [18-carbon
      spacer (x3)] = /5Biosg//iSp18//iSp18//iSp18/

<400> SEQUENCE: 243
ttgattgtat agtcagatag ttactttaaa aaatt                              35
```

<210> SEQ ID NO 244
<211> LENGTH: 20
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification linked to [18-carbon spacer (x3)] = /5Biosg//iSp18//iSp18//iSp18/

<400> SEQUENCE: 244
gcagcagctg acagacctaa                    20

<210> SEQ ID NO 245
<211> LENGTH: 21
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification linked to [18-carbon spacer (x3)] = /5Biosg//iSp18//iSp18//iSp18/

<400> SEQUENCE: 245
ggaccggatt acccaagaca g                    21

<210> SEQ ID NO 246
<211> LENGTH: 27
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification linked to [18-carbon spacer (x3)] = /5Biosg//iSp18//iSp18//iSp18/

<400> SEQUENCE: 246
ggaaataaat gggaaagaac atcctcc                    27

<210> SEQ ID NO 247
<211> LENGTH: 32
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification linked to [18-carbon spacer (x3)] = /5Biosg//iSp18//iSp18//iSp18/

<400> SEQUENCE: 247
aatcagtaac cttaaaaatt tgtgttattt cg                    32

<210> SEQ ID NO 248
<211> LENGTH: 27
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification linked to [18-carbon

```
      spacer (x3)] = /5Biosg//iSp18//iSp18//iSp18/

<400> SEQUENCE: 248
atgtctccaa tttctgaagc aattttg                                       27

<210> SEQ ID NO 249
<211> LENGTH: 29
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' biotin modification linked to [18-carbon
      spacer (x3)] = /5Biosg//iSp18//iSp18//iSp18/

<400> SEQUENCE: 249
agctcatcct agtaaatgtg ttaccatac                                     29

<210> SEQ ID NO 250
<211> LENGTH: 58
<212> TYPE: DNA
<213> ORGANISM: Artificial Sequence
<220> FEATURE:
<223> OTHER INFORMATION: synthetic nucleotide construct

<400> SEQUENCE: 250
aatgatacgg cgaccaccga gatctacact ctttccctac acgacgctct tccgatct    58

<210> SEQ ID NO 251
<211> LENGTH: 19
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (1)..(1)
<223> OTHER INFORMATION: 5' phosporylation (5Phos)

<400> SEQUENCE: 251
gatcggaaga gcgtcgtgt                                                19

<210> SEQ ID NO 252
<211> LENGTH: 58
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(40)
<223> OTHER INFORMATION: N is A, C, G, or T

<400> SEQUENCE: 252
gtgactggag ttcagacgtg tgctcttccg atctwnnnnn wctcacgcgc caatcggt    58

<210> SEQ ID NO 253
<211> LENGTH: 58
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(40)
<223> OTHER INFORMATION: N is A, C, G, or T
```

<400> SEQUENCE: 253
gtgactggag ttcagacgtg tgctcttccg atctwnnnnn waggcagcca ggcaggaa    58

<210> SEQ ID NO 254
<211> LENGTH: 65
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(40)
<223> OTHER INFORMATION: N is A, C, G, or T

<400> SEQUENCE: 254
gtgactggag ttcagacgtg tgctcttccg atctwnnnnn wagaagccat tgagagagca    60
aggta    65

<210> SEQ ID NO 255
<211> LENGTH: 65
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(40)
<223> OTHER INFORMATION: N is A, C, G, or T

<400> SEQUENCE: 255
gtgactggag ttcagacgtg tgctcttccg atctwnnnnn wcgaaggtca tcaacaccaa    60
ttcca    65

<210> SEQ ID NO 256
<211> LENGTH: 65
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(40)
<223> OTHER INFORMATION: N is A, C, G, or T

<400> SEQUENCE: 256
gtgactggag ttcagacgtg tgctcttccg atctwnnnnn waggatgagt tttgtgaaag    60
gctgg    65

<210> SEQ ID NO 257
<211> LENGTH: 66
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(40)
<223> OTHER INFORMATION: N is A, C, G, or T

<400> SEQUENCE: 257
gtgactggag ttcagacgtg tgctcttccg atctwnnnnn wggaacacca atactcagga    60
gctata    66

<210> SEQ ID NO 258
<211> LENGTH: 76

<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(40)
<223> OTHER INFORMATION: N is A, C, G, or T

<400> SEQUENCE: 258
gtgactggag ttcagacgtg tgctcttccg atctwnnnnn wtatggacac tacaaaggaa    60
agaatagaaa aaagta    76

<210> SEQ ID NO 259
<211> LENGTH: 76
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(40)
<223> OTHER INFORMATION: N is A, C, G, or T

<400> SEQUENCE: 259
gtgactggag ttcagacgtg tgctcttccg atctwnnnnn wgtccatttg ttcaagtttt    60 tcctttaaa tcaaat    76

<210> SEQ ID NO 260
<211> LENGTH: 76
<212> TYPE: DNA
<213> ORGANISM: Artificial Sequence
<220> FEATURE:
<223> OTHER INFORMATION: synthetic nucleotide construct
<220> FEATURE:
<221> NAME/KEY: misc_feature
<222> LOCATION: (36)..(40)
<223> OTHER INFORMATION: N is A, C, G, or T

<400> SEQUENCE: 260
gtgactggag ttcagacgtg tgctcttccg atctwnnnnn wttggattct ttaataacag    60
ctataactac aaatgg    76

<210> SEQ ID NO 261
<211> LENGTH: 22
<212> TYPE: DNA
<213> ORGANISM: Artificial Sequence
<220> FEATURE:
<223> OTHER INFORMATION: synthetic nucleotide construct

<400> SEQUENCE: 261
gtgactggag ttcagacgtg tg    22

```
<210> SEQ ID NO 262
<211> LENGTH: 52
<212> TYPE: DNA
<213> ORGANISM: Artificial Sequence
<220> FEATURE:
<223> OTHER INFORMATION: synthetic nucleotide construct
<220> FEATURE:
<221> NAME/KEY: modified_base
<222> LOCATION: (24)..(25)
<223> OTHER INFORMATION: 3' end of position 24 (T) conjugated with index
      sequence to 5' end of positin 25 (G)

<400> SEQUENCE: 262
caagcagaag acggcatacg agatgtgact ggagttcaga cgtgtgctct tc            52
```

PRIMER EXTENSION TARGET ENRICHMENT

CROSS-REFERENCE TO RELATED PATENT APPLICATIONS

The present application claims benefit of priority to U.S. Provisional Patent Application No. 62/361,426, filed Jul. 12, 2016 and U.S. Provisional Patent Application No. 62/469,480, filed Mar. 9, 2017, each of which are incorporated by reference in their entirety.

BACKGROUND OF THE INVENTION

Sample preparation for high-throughput sequencing typically involves an enrichment step that increases the ratio of target nucleic acids to non-target nucleic acids in a sample. Such enrichment can utilize a number of different physicochemical attributes of the target and non-target nucleic acids. See, Mamanova et al., Nat. Methods, 7:111-118 (2010). For example, target nucleic acids having known sequence attributes can be enriched by selecting from a sample nucleic acid fragments having the target sequences. Sequence-based enrichment techniques known in the art include but are not limited to hybrid capture, multiplex PCR amplification, primer extension target enrichment (PETE), linear array, and bead based methods.

BRIEF SUMMARY OF THE INVENTION

Described herein are improved methods and compositions for primer extension target enrichment (PETE) of target nucleic acids from a sample. Methods and compositions described herein can, e.g., be used for preparation of samples for analysis by high-throughput sequencing. In some cases, the methods and compositions described herein can provide increased sensitivity, decreased background, or increased efficiency in high-throughput sequencing library preparation or analysis. In some cases, the improvement is provided by the use of two unidirectional primers that are sequentially hybridized to the same target polynucleotide and extended with a polymerase.

In some embodiments, a method for enriching a target polynucleotide from a sample is provided, the method comprising: providing a reaction mixture comprising the sample and a first target-specific primer, wherein the sample comprises single-stranded target polynucleotide having a 3' and a 5' end and a plurality of structurally different single-stranded non-target polynucleotides; hybridizing a first target-specific primer to the single-stranded target polynucleotide in the reaction mixture, wherein the first target-specific primer hybridizes at least 6 nucleotides from the 3' end of the single-stranded target polynucleotide; extending the hybridized first target-specific primer with a DNA polymerase to form a first double-stranded product comprising the target polynucleotide hybridized to the extended first target-specific primer, wherein the hybridized target polynucleotide comprises a single-stranded overhang region of at least 6 consecutive nucleotides at the 3' end; removing single-stranded target and non-target polynucleotides that are not hybridized to extended target-specific primer, if present from the reaction mixture; hybridizing a second target-specific primer to the single-stranded overhang region at the 3' end of the hybridized target polynucleotide, wherein the second target-specific primer comprises a 3' hybridizing region and a barcode region; and extending the hybridized second target-specific primer with a DNA polymerase, wherein the DNA polymerase comprises strand displacement activity, 5'-3' double stranded DNA exonuclease activity, or a combination thereof, thereby displacing or degrading the extended first target-specific primer and forming a second double-stranded product comprising a barcode, wherein the second double-stranded product comprises the target polynucleotide hybridized to an extended second target-specific primer, wherein the extended second target-specific primer comprises: i) a complement of at least a portion of the target polynucleotide; and, ii) a single-stranded 5' overhang region comprising the barcode.

In some embodiments, the first target-specific primer comprises an affinity ligand and: —the extending comprises immobilizing the first double-stranded product onto a solid surface, wherein the solid surface comprises an affinity element that specifically binds the affinity ligand of the first target-specific primer; and—the removing comprises washing away non-immobilized polynucleotides. In some embodiments, the first target-specific primer is covalently attached to a solid surface and: —the hybridizing comprises contacting the solid surface to which the first target-specific primer is covalently attached to the single-stranded target polynucleotide in the reaction mixture; and—the removing comprises washing away non-immobilized polynucleotides. In some embodiments, —the extending in c) comprises extending the hybridized first target-specific primer in the presence of nucleotides that are covalently linked to an affinity ligand, thereby incorporating nucleotides linked to the affinity ligand into the extended first target-specific primer and then immobilizing the first double-stranded product onto a solid surface, wherein the solid surface comprises an affinity element that specifically binds the affinity ligand incorporated into the extended first target-specific primer; and—the removing in d) comprises washing away non-immobilized polynucleotides.

In some embodiments, the removing further comprises removing un-extended first target-specific primer, if present, by contacting the un-extended primer with a 5' to 3' single-stranded exonuclease. In some embodiments, the first target-specific primer comprises an affinity ligand and: the hybridizing a second target-specific primer comprises hybridizing the second target-specific primer to an immobilized first double-stranded product; and the extending the hybridized second target-specific primer comprises extending the second target-specific primer with the DNA polymerase comprising strand displacement activity and/or 5'-3' double-stranded exonuclease activity, thereby releasing the target polynucleotide into solution.

In some embodiments, the method further comprises: attaching (e.g., ligating or attaching by primer extension) a first and a second universal adapter to:) a first and a second end, respectively, of the second double-stranded product; or a 5' and 3' end, respectively, of a single-stranded extended second target-specific primer recovered from the second double-stranded product, or a first and a second end of a double-stranded amplification product of the recovered single-stranded extended second target-specific primer. The method can further comprise hybridizing a first universal primer to the first universal adapter and a second universal primer to the second universal adapter and extending the hybridized universal primers with a polymerase, thereby amplifying: the target polynucleotide of the universal adapter ligated second double-stranded product; or the target polynucleotide of the universal adapter ligated recovered second target-specific primer, or a double-stranded product thereof.

In some embodiments, the first or second universal adapter comprises a second barcode and the ligating the universal adapter comprising the second barcode ligates the second barcode to the extended second target-specific primer. In some embodiments, the second universal adapter is ligated to a 3' end of the recovered single-stranded extended second target-specific primer by a method comprising: i) contacting the recovered single-stranded extended second target-specific primer with a terminal transferase, thereby appending a 3' tail region comprising at least about 3, or about 8, consecutive nucleotides of the same sequence to the 3' end of the recovered single-stranded extended second target-specific primer and generating a tailed single-stranded extended second target-specific primer; ii) contacting the tailed single-stranded extended second target-specific primer with a second universal adapter comprising a double-stranded polynucleotide comprising a single-stranded 3' overhang region that is complementary to the 3' tail region of the tailed single-stranded extended second target-specific primer, thereby hybridizing the second universal adapter to the tailed single-stranded extended second target-specific primer; and iii) ligating a 5' end of the hybridized second universal adapter to the 3' tail region of the tailed single-stranded extended target-specific primer.

In some embodiments, the first universal adapter is ligated to a 5' end of the recovered single-stranded second target-specific primer by a method comprising: i) contacting the tailed or recovered single-stranded second target-specific primer with a second universal adapter comprising a double-stranded polynucleotide comprising a single-stranded 5' overhang region that is complementary to at least a portion of the barcode region of the tailed or recovered single-stranded second target-specific primer, thereby hybridizing the second universal adapter to the tailed or recovered single-stranded second target-specific primer; and iii) ligating a 3' end of the hybridized second universal adapter to a 5' end of the barcode region of the tailed or recovered single-stranded second target-specific primer. In some embodiments, the method further comprises: contacting the second double-stranded product with a universal adaptor loaded transposase to catalyze fragmentation and in vitro integration of first or second universal adapters at fragment ends; and hybridizing a first universal primer to the first universal adapters and a second universal primer to the second universal adapters and extending the hybridized universal primers with a polymerase, thereby amplifying fragments comprising first and second universal adapters.

In some embodiments: —the single-stranded target polynucleotide comprises RNA, preferably mRNA; and—the extending comprises extending the first target-specific primer with an RNA-dependent DNA polymerase to form a first double stranded product, wherein the first double-stranded product comprises a cDNA:RNA hybrid. In some embodiments, the hybridized target polynucleotide of the second double-stranded product formed by the extending of the second target-specific primer comprises a 3' single-stranded overhang region comprising at least 1 nucleotide (e.g., from 1 to 5, from 1-10, from 1-100, or from 1 to 1,000), and the method further comprises: trimming the 3' overhang region of the hybridized target polynucleotide with an enzyme comprising 3' to 5' single-stranded DNA exonuclease activity; and extending the trimmed 3' end of the hybridized target polynucleotide with a DNA polymerase, thereby incorporating a complement of the single-stranded 5' overhang region of the extended second target-specific primer that comprises the barcode into the target polynucleotide of the second double-stranded product.

In some embodiments, the method comprises: ligating a first universal adapter comprising a first universal primer binding site to the second double-stranded product formed by the extending of the second target-specific primer, the trimmed second double-stranded product formed by the ligating of the first and second universal adaptors, or the trimmed and extended second double-stranded product formed by the hybridizing of the first universal primer to the first universal adaptor, wherein the first universal adapter is ligated to a 3' end of the extended second target-specific primer and the 5' end of the target polynucleotide; and ligating a second universal adapter comprising a second universal primer binding site to the single-stranded 5' overhang region of the extended second target-specific primer of the second double-stranded product formed by the extending of the second target-specific primer, the trimmed second double-stranded product formed by the ligating of the first and second universal adaptors, or the trimmed and extended second double-stranded product formed the hybridizing of the first universal primer to the first universal adaptor.

In some embodiments, —the ligating of the second universal adaptor comprises ligating the second universal adapter to the second double-stranded product formed by the extending of the second target-specific primer, or the trimmed second double-stranded product formed by the ligating of the first and second universal adaptors; and—the hybridizing of the first universal primer to the first universal adaptor comprises incorporating a complement of the barcode and a complement of the second universal primer binding site into the target polynucleotide of the second double-stranded product. In some embodiments, the second universal adapter is a double-stranded polynucleotide comprising a single-stranded 5' overhang region, wherein the single-stranded 5' overhang region is complementary to at least a portion of the single-stranded 5' overhang region of the extended second target-specific primer. In some embodiments, the ligating of the second universal adaptor comprises ligating a first universal adapter that is resistant to a 5' to 3' double-stranded DNA exonuclease activity, and the method further comprises: recovering the target polynucleotide comprising the complement of the barcode and the complement of the second universal primer binding site from the second double-stranded product formed by the hybridizing of the first universal primer to the first universal adaptor by contacting the second double-stranded product formed by the hybridizing of the first universal primer to the first universal adaptor with an enzyme comprising the 5' to 3' double-stranded DNA exonuclease activity, thereby degrading the extended second target-specific primer.

In some embodiments, the ligating of the second universal adaptors comprises ligating a first universal adapter comprising an affinity ligand, wherein the affinity ligand is attached to a strand of the first universal adapter that is ligated to the target polynucleotide of the double-stranded product, and the method further comprises: recovering the target polynucleotide comprising the complement of the barcode and the complement of the second universal primer binding site from the second double-stranded product formed by the hybridizing of the first universal primer to the first universal adaptor by i) immobilizing the second double-stranded product to a solid surface comprising an affinity element that specifically binds the affinity ligand; and ii) eluting the extended second target-specific primer from the second double-stranded product to release the extended second target-specific primer into solution.

In some embodiments, the eluting comprises heating the second double-stranded product to a temperature sufficient to release the extended second target specific primer into solution. In some embodiments, the temperature sufficient to release the extended second target specific primer into solution comprises a temperature of at least 75° C., 80° C., 90° C., or 95° C. In some embodiments, the eluting comprises contacting the second double-stranded product with a denaturing agent under conditions that release the extended second target specific primer into solution. In some embodiments the denaturing agent comprises an aqueous solution of an alkali hydroxide.

In some embodiments, the ligating of the second universal adaptors comprises ligating a second universal adapter comprising an affinity ligand, wherein the affinity ligand is attached to a strand of the second universal adapter that is ligated to the extended second target-specific primer, and the method further comprises: recovering the target polynucleotide comprising the complement of the barcode and the complement of the second universal primer binding site from the second double-stranded product formed by the hybridizing of the first universal primer to the first universal adaptor by i) immobilizing the second double-stranded product to a solid surface comprising an affinity element that specifically binds the affinity ligand; and ii) eluting the target polynucleotide from the second double-stranded product to release the target polynucleotide into solution. In some embodiments, the eluting comprises heating the second double-stranded product to a temperature sufficient to release the target polynucleotide into solution. In some embodiments, the temperature sufficient to release the target polynucleotide into solution comprises a temperature of at least 75° C., 80° C., 90° C., or 95° C.

In some embodiments, the eluting comprises contacting the second double-stranded product with a denaturing agent under conditions that release the target polynucleotide into solution. In some embodiments, the denaturing agent comprises an aqueous solution of an alkali hydroxide. In some embodiments, the ligating of the second universal adaptors comprises ligating a first or second universal adapter comprising a label to the second double-stranded product formed by the hybridizing of the first universal primer to the first universal adaptor, and the method further comprises: recovering the second double-stranded product formed by the hybridizing of the first universal primer to the first universal adaptor by i) immobilizing the universal adapter comprising the label, thereby immobilizing the second double-stranded product; ii) washing the immobilized second double-stranded product; and iii) eluting the second double-stranded product into solution.

In some embodiments, the label of the labeled first or second universal adapter comprises an affinity ligand, the immobilizing comprises contacting the affinity ligand to a solid surface comprising an affinity element that specifically binds the affinity ligand, and the eluting comprises contacting the immobilized second-double stranded product with an denaturing agent under conditions sufficient to disrupt the affinity ligand: affinity element interaction and release the second double-stranded product into solution. In some embodiments, the conditions sufficient to disrupt the affinity ligand: affinity element interaction comprise 8 M urea, 6 M guanidine, a pH of less than 2.0, or a pH of greater than 10.0 (e.g., a pH of or about 11, or 12).

In some embodiments, the label of the labeled first or second universal adapter is covalently attached via a linker to a solid surface before or after ligation to the second double-stranded product, and the eluting comprises cleaving the linker to release the second double-stranded product into solution. In some embodiments, the cleavage agent is a thiol that cleaves a disulfide linker to release the second double-stranded product into solution. In some embodiments, the second universal adapter comprises a second barcode, ligating the second universal adapter comprising the second barcode ligates the second barcode to the extended second target-specific primer, and extending the trimmed 3' end of the hybridized target polynucleotide with the DNA polymerase incorporates a complement of the second barcode into the target polynucleotide. In some embodiments, the method further comprises hybridizing a first and second universal primer to the first and second universal adapters respectively, and extending the universal primers with a polymerase, thereby amplifying the target polynucleotide.

In another aspect, the present invention provides a method for enriching a plurality of structurally different target polynucleotides from a sample, wherein the method comprises performing any one of the foregoing embodiments for each structurally different target polynucleotide, wherein the hybridizing of the first target-specific primer to the single-stranded target polynucleotide comprises hybridizing a plurality of structurally different first target-specific primers to the plurality of structurally different single-stranded target polynucleotides in a single reaction mixture. In some embodiments, the method comprises attaching a first and a second universal adapter to at least a portion of the plurality of the target polynucleotides or a plurality of second target-specific primer extension products by ligation or Tn5 transposase-mediated attachment.

In yet another aspect, the present invention provides a method for sequencing a plurality of target polynucleotides from a sample comprising the plurality of target polynucleotides and a plurality of non-target polynucleotides, the method comprising: enriching the target polynucleotides from the sample by performing one or more of the foregoing methods to produce an enriched and adapter-attached sample; and sequencing the enriched and adapter-attached sample. In some embodiments, the percent of on-target reads from the enriched and adapter ligated sample is at least about 10%, at least about 15%, at least about 25%, at least about 50%, at least about 65%, at least about 70%, at least about 75%, at least about 80%, at least about 85%, at least about 90%, or at least about 95%. In some embodiments, the percent of on-target reads from the enriched and adapter ligated sample is from about 25% to about 99%, from about 50% to about 99%, from about 50% to about 90%, from about 50% to about 85%, from about 65% to about 99%, from about 65% to about 90%, from about 65% to about 85%, from about 75% to about 99%, from about 75% to about 90%, or from about 75% to about 85%.

In some embodiments, the method comprises a step of removing the extended second target-specific primer from the second double-stranded product using an endonuclease. In some embodiments, extending the hybridized second target-specific primer is performed in the presence of one or more non-conventional nucleotides. In some embodiments, the non-conventional base introduces an abasic site that can be specifically cleaved without cleaving DNA in the same reaction. Exemplary enzymes that cleave abasic sites include, e.g., Tth Endonuclease IV, Endonuclease IV or Endonuclease VIII. In some embodiments, the non-conventional base that introduces the basic site is Int 1',2'-Dideoxyribose. Other non-conventional bases can be selected from, e.g., deoxyuracil and deoxyinosine. In some embodiments, the extended second target-specific primer contains deoxyinosine and is removed from the second double-stranded product using endonuclease V; and in other embodiments, the extended second target-specific primer contains deoxyuracil and is removed from the second double-stranded product using uracil-N-DNA glycosylase and endonuclease VIII.

In some embodiments, the universal adaptor comprises one or more non-conventional nucleotides selected from deoxyuracil, deoxyinosine, and Int 1',2'-Dideoxyribose, and prior to universal amplification, the sample is contacted with an endonuclease. In some embodiments, the universal adaptor contains deoxyinosine and is removed from the second double-stranded product using endonuclease V; and in other embodiments, the universal adaptor contains deoxyuracil and is removed from the second double-stranded product using uracil-N-DNA glycosylase and endonuclease VIII.

In some embodiments, the first target-specific primer is part of an oligonucleotide having a 3' end and a 5' end, the first target-specific primer is at the 3' end of the oligonucleotide, and the oligonucleotide further comprises the second target-specific primer, the first target-specific and the second target-specific primer are linked in the oligonucleotide by one or more non-conventional nucleotide(s), and the hybridizing of the first target-specific primer comprises hybridizing the oligonucleotide to the single-stranded target polynucleotide and before the hybridizing of the second target-specific primer, the method further comprises treating the oligonucleotide to cleave and release the second target-specific primer from the oligonucleotide, wherein the released second target-specific primer has a 3' end available for extension. In some embodiments, the non-conventional nucleotide is deoxyinosine and the endonuclease is endonuclease V. In some embodiments, the non-conventional nucleotide is deoxyuracil and the endonuclease is endonuclease VIII and the sample is further contacted with uracil-N-DNA glycosylase (UNG). In some embodiments, the non-conventional nucleotide is Int 1',2'-Dideoxyribose and the endonuclease is Tth Endonuclease IV, Endonuclease IV or Endonuclease VIII.

In some embodiments, the method comprises attaching universal adapters to: target polynucleotides (e.g., the single-stranded target polynucleotide or double-stranded polynucleotides that are later denatured or otherwise rendered single-stranded) before the hybridizing of the first target-specific primer to the single stranded target; or the hybridized target polynucleotide after the extending of the hybridized first target-specific primer and before the hybridizing of the second target-specific primer. In some embodiments, the attaching comprises ligation. In some embodiments, the attaching comprises tagmentation. In some embodiments, the universal adaptor comprises one or more barcode sequences.

Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Spring Harbor Lab Press (Cold Spring Harbor, NY 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein, the term "substantially all" in reference to removing substantially all of a component of a reaction mixture means removing at least 90%, 95%, 99%, of the component from the reaction mixture.

As used herein, the term "barcode" refers to a nucleic acid sequence that can be detected and identified. Barcodes can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides long. Barcodes can employ error correcting codes such that one or more errors in synthesis, replication, and/or sequencing can be corrected to identify the barcode sequence. Examples of error correcting codes and their use in barcodes and barcode identification and/or sequencing include, but are not limited to, those described in U.S. 2010/0,323,348; and U.S. Pat. No. 8,715,967. In some cases, the barcodes are designed to have a minimum number of distinct nucleotides with respect to all other barcodes of a population. The minimum number can be 1, 2, 3, 4, 5, 6, 7, 8, 9, 10, 11, 12, 13, 14, 15, or more. Thus, for example, a population of barcodes having a minimum number of at least 5 distinct nucleotides will differ at least 5 nucleotide positions from all other barcodes in the population.

As used herein, the term "multiplex identifier," "MID," and the like, refers to a barcode that identifies a source or sample. As such, all or substantially all, MID barcoded polynucleotides from a single source or sample will share an MID of the same sequence; while all, or substantially all (e.g., at least 90% or 99%), MID barcoded polynucleotides from different sources or samples will have a different MID barcode sequence. Polynucleotides from different sources or samples and having different MIDs can then be mixed and sequenced in parallel while maintaining source/sample information. Thus sequence reads can be assigned to individual samples.

As used herein, the term "universal identifier," "universal molecular identifier," "unique molecular identifier," "UID," and the like, refers to a barcode that identifies a polynucleotide to which it is attached. Typically, all, or substantially all (e.g., at least 90% or 99%), UID barcodes in a mixture of UID barcoded polynucleotides are unique.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologues, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

"Polymerase" refers to an enzyme that performs template-directed synthesis of polynucleotides. A DNA polymerase can add free nucleotides only to the 3' end of the newly forming strand. This results in elongation of the newly forming strand in a 5'-3' direction. No known DNA polymerase is able to begin a new chain (de novo). DNA polymerase can add a nucleotide only on to a pre-existing 3'—OH group, and, therefore, needs a primer at which it can add the first nucleotide. Non-limiting examples of polymerases include prokaryotic DNA polymerases (e.g. Pol I, Pol II, Pol III, Pol IV and Pol V), eukaryotic DNA polymerase, archaeal DNA polymerase, telomerase, reverse transcriptase and RNA polymerase. Reverse transcriptase is an RNA-dependent DNA polymerase which synthesizes DNA from an RNA template. The reverse transcriptase family contain both DNA polymerase functionality and RNase H functionality, which degrades RNA base-paired to DNA. RNA polymerase, is an enzyme that synthesizes RNA using DNA as a template during the process of gene transcription. RNA polymerase polymerizes ribonucleotides at the 3' end of an RNA transcript.

In some embodiments, a polymerase from the following may be used in a polymerase-mediated primer extension, end-modification (e.g., terminal transferase, degradation, or polishing), or amplification reaction: archaea (e.g., *Thermococcus litoralis* (Vent, GenBank: AAA72101), *Pyrococcus furiosus* (Pfu, GenBank: D12983, BAA02362), *Pyrococcus woesii*, *Pyrococcus* GB-D (Deep Vent, GenBank: AAA67131), *Thermococcus kodakaraensis* KODI (KOD, GenBank: BD175553, BAA06142; *Thermococcus* sp. strain KOD (Pfx, GenBank: AAE68738)), *Thermococcus gorgonarius* (Tgo, Pdb: 4699806), *Sulfolobus solataricus* (GenBank: NC002754, P26811), Aeropyrum pernix (GenBank: BAA81109), *Archaeglobus fulgidus* (GenBank: 029753), *Pyrobaculum aerophilum* (GenBank: AAL63952), *Pyrodictium occultum* (GenBank: BAA07579, BAA07580), *Thermococcus* 9 degree Nm (GenBank: AAA88769, Q56366), *Thermococcus fumicolans* (GenBank: CAA93738, P74918), *Thermococcus hydrothermalis* (GenBank: CAC18555), *Thermococcus* sp. GE8 (GenBank: CAC12850), *Thermococcus* sp. JDF-3 (GenBank: AX135456; WO0132887), *Thermococcus* sp. TY (GenBank: CAA73475), *Pyrococcus abyssi* (GenBank: P77916), *Pyrococcus glycovorans* (GenBank: CAC12849), *Pyrococcus horikoshii* (GenBank: NP 143776), *Pyrococcus* sp. GE23 (GenBank: CAA90887), *Pyrococcus* sp. ST700 (GenBank: CAC 12847), *Thermococcus pacificus* (GenBank: AX411312.1), *Thermococcus zilligii* (GenBank: DQ3366890), *Thermococcus aggregans*, *Thermococcus barossii*, *Thermococcus celer* (GenBank: DD259850.1), *Thermococcus profundus* (GenBank: E14137), *Thermococcus siculi* (GenBank: DD259857.1), *Thermococcus thioreducens*, *Thermococcus onnurineus* NA1, *Sulfolobus acidocaldarium, Sulfolobus tokodaii, Pyrobaculum calidifontis, Pyrobaculum islandicum* (GenBank: AAF27815), *Methanococcus jannaschii* (GenBank: Q58295), *Desulforococcus* species TOK, *Desulfurococcus, Pyrolobus, Pyrodictium, Staphylothermus, Vulcanisaetta, Methanococcus* (GenBank: P52025) and other archaeal B polymerases, such as GenBank AAC62712, P956901, BAAA07579)), thermophilic bacteria *Thermus* species (e.g., *flavus, ruber, thermophilus, lacteus, rubens, aquaticus*), *Bacillus stearothermophilus, Thermotoga maritima, Methanothermus fervidus*, KOD polymerase, TNA1 polymerase, *Thermococcus* sp. 9 degrees N-7, T4, T7, phi29, *Pyrococcus furiosus, P. abyssi, T. gorgonarius, T. litoralis, T. zilligii*, T. sp. GT, P. sp. GB-D, KOD, Pfu, *T. gorgonarius, T. zilligii, T. litoralis* and *Thermococcus* sp. 9N-7 polymerases.

The term "thermostable polymerase," refers to an enzyme that is stable to heat, is heat resistant, and retains sufficient activity to effect subsequent polynucleotide extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in, e.g., U.S. Pat. Nos. 4,683,202, 4,683,195, and 4,965,188, which are incorporated herein by reference. As used herein, a thermostable polymerase is suitable for use in a temperature cycling reaction such as the polymerase chain reaction ("PCR"), a primer extension reaction, or an end-modification (e.g., terminal transferase, degradation, or polishing) reaction. Irreversible denaturation for purposes herein refers to permanent and complete loss of enzymatic activity. For a thermostable polymerase, enzymatic activity refers to the catalysis of the combination of the nucleotides in the proper manner to form polynucleotide extension products that are complementary to a template nucleic acid strand. Thermostable DNA polymerases from thermophilic bacteria include, e.g., DNA polymerases from *Thermotoga maritima, Thermus aquaticus, Thermus thermophilus, Thermus flavus, Thermus filiformis, Thermus* species sps117, *Thermus* species Z05, *Thermus caldophilus, Bacillus caldotenax, Thermotoga neopolitana, Thermosipho africanus*, and other thermostable DNA polymerases disclosed above.

In some cases, the nucleic acid (e.g., DNA or RNA) polymerase may be a modified naturally occurring Type A polymerase. A further embodiment of the invention generally relates to a method wherein a modified Type A polymerase, e.g., in a primer extension, end-modification (e.g., terminal transferase, degradation, or polishing), or amplification reaction, may be selected from any species of the genus Meiothermus, *Thermotoga*, or *Thermomicrobium*. Another embodiment of the invention generally pertains to a method wherein the polymerase, e.g., in a primer extension, end-modification (e.g., terminal transferase, degradation or polishing), or amplification reaction, may be isolated from any of *Thermus aquaticus* (Taq), *Thermus thermophilus, Thermus caldophilus*, or *Thermus filiformis*. A further embodiment of the invention generally encompasses a method wherein the modified Type A polymerase, e.g., in a primer extension, end-modification (e.g., terminal transferase, degradation, or polishing), or amplification reaction, may be isolated from *Bacillus stearothermophilus, Sphaerobacter thermophilus, Dictoglomus thermophilum*, or *Escherichia coli*. In another embodiment, the invention generally relates to a method wherein the modified Type A polymerase, e.g., in a primer extension, end-modification (e.g., terminal transferase, degradation, or polishing), or amplification reaction, may be a mutant Taq-E507K polymerase. Another embodiment of the invention generally pertains to a method wherein a thermostable polymerase may be used to effect amplification of the target nucleic acid.

As used herein the term "primer" refers to an oligonucleotide which binds to a specific region of a single-stranded template nucleic acid molecule and initiates nucleic acid synthesis via a polymerase-mediated enzymatic reaction, extending from the 3' end of the primer and complementary to the sequence of the template molecule. PCR amplification primers can be referred to as 'forward' and 'reverse' primers, one of which is complementary to a nucleic acid strand and the other of which is complementary to the complement of that strand. Typically a primer comprises fewer than about 100 nucleotides and preferably comprises fewer than about 30 nucleotides. Exemplary primers range from about 5 to about 25 nucleotides. Primers can comprise, for example, RNA and/or DNA bases, as well as non-naturally-occurring bases. The directionality of the newly forming strand (the daughter strand) is opposite to the direction in which DNA polymerase moves along the template strand. In some cases, a target-specific primer specifically hybridizes to a target polynucleotide under hybridization conditions. Such hybridization conditions can include, but are not limited to, hybridization in isothermal amplification buffer (20 mM Tris-HCl, 10 mM $(NH_4)_2SO_4$, 50 mM KCl, 2 mM $MgSO_4$, 0.1% TWEEN® 20, pH 8.8 at 25° C.) at a temperature of about 40° C., 45° C., 50° C., 55° C., 60° C., 65° C., or 70° C.

As used herein, the term "universal primer" and "universal primers" refers to a primer that can hybridize to and support amplification of target polynucleotides having a shared complementary universal primer binding site. Similar, the term "universal primer pair" refers to a forward and reverse primer pair that can hybridize to and support PCR amplification of target polynucleotides having shared complementary forward and reverse universal primer binding sites. Such universal primer(s) and universal primer binding site(s) can allow single or double-primer mediated universal amplification (e.g., universal PCR) of target polynucleotide regions of interest.

As used herein the term "sample" refers to any biological sample that comprises nucleic acid molecules, typically comprising DNA and/or RNA. Samples may be tissues, cells or extracts thereof, or may be purified samples of nucleic acid molecules. Use of the term "sample" does not necessarily imply the presence of target sequence within nucleic acid molecules present in the sample.

BRIEF DESCRIPTION OF THE DRAWINGS

FIGS. 1A-E illustrate an embodiment of unidirectional double primer extension target enrichment (UD-PETE). In the embodiment illustrated, the first primer extension product is hybridized to a target polynucleotide and extended with a polymerase (FIG. 1A). The first primer, and thus the first primer extension product, is biotinylated. Biotinylated first primer, or first primer extension product is captured onto an anti-biotin (e.g., streptavidin) coated solid surface and hybridization (FIG. 1B) and extension of the second target-specific primer releases target polynucleotide away from the immobilized first primer extension product (FIG. 1C). A first and second adapter containing a first and second universal primer binding site respectively can be ligated to the second target-specific primer extension product (FIG. 1D). The adapter ligated extension product can be amplified by universal PCR (FIG. 1E).

FIGS. 2A-E illustrate an alternate embodiment of UD-PETE. In this embodiment, a double-stranded polynucleotide containing the single-stranded target polynucleotide hybridized to the second target-specific primer extension product is ligated to an adapter containing a universal primer hybridization site (FIG. 2D) and digested at an unhybridized 3' single-stranded overhang region of the target polynucleotide with an enzyme that exhibits 3' to 5' single-stranded exonuclease activity (FIG. 2E).

FIGS. 3A-D illustrate methods of incorporating MID and UID barcodes into the original target polynucleotide and recovering the barcoded original single-stranded target polynucleotide and removing the hybridized second target-specific primer extension product.

DETAILED DESCRIPTION OF THE INVENTION

I. Introduction

Figure 2A:
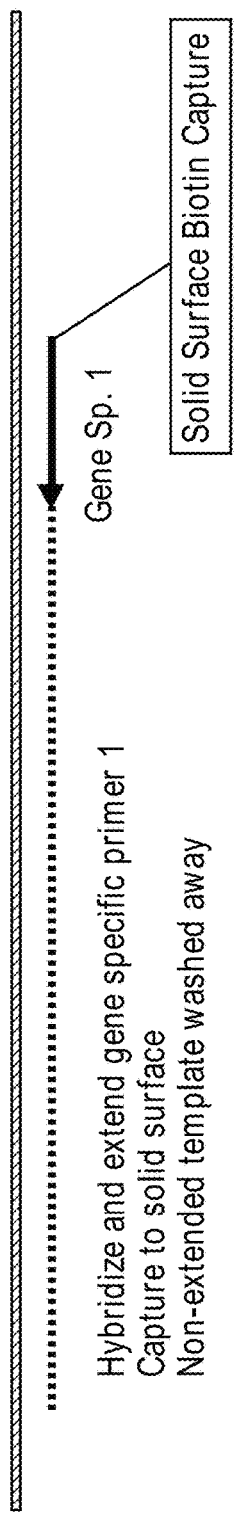
Figure 2B:
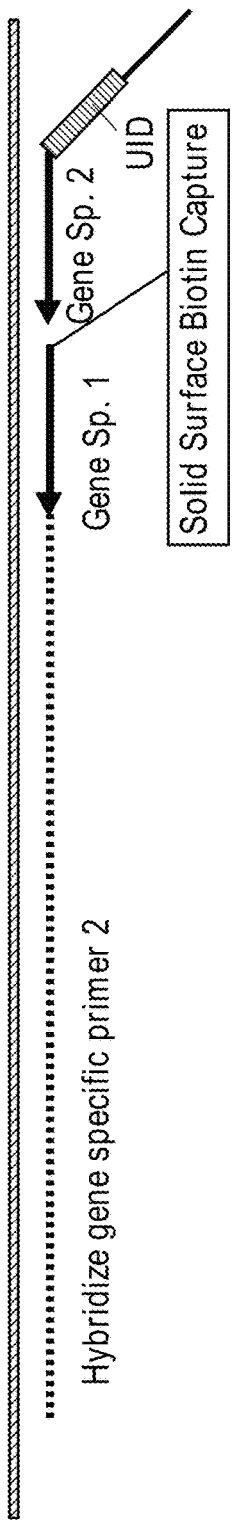
Figure 2C:
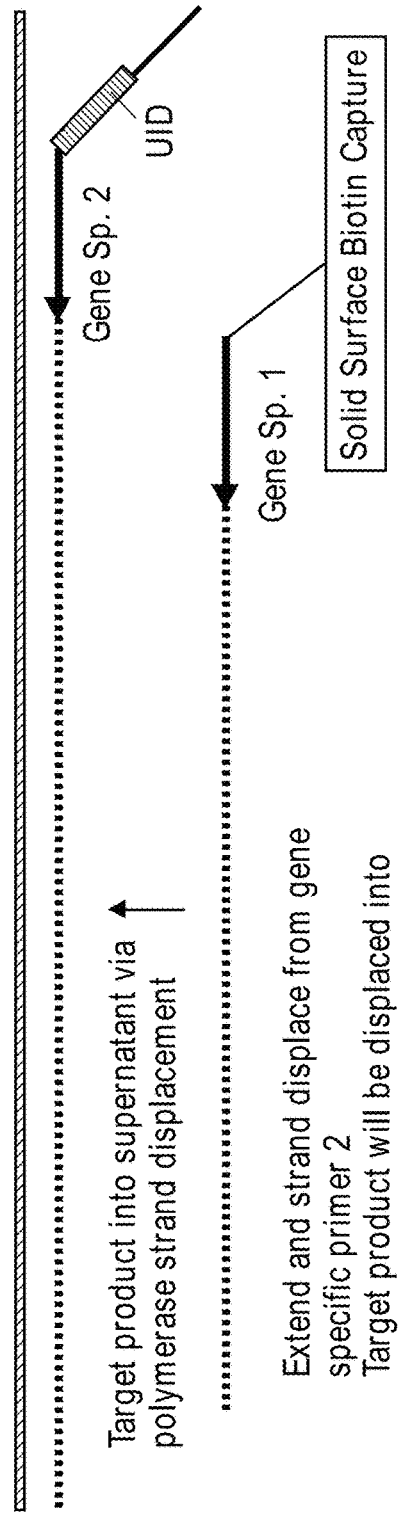
Figure 3C:
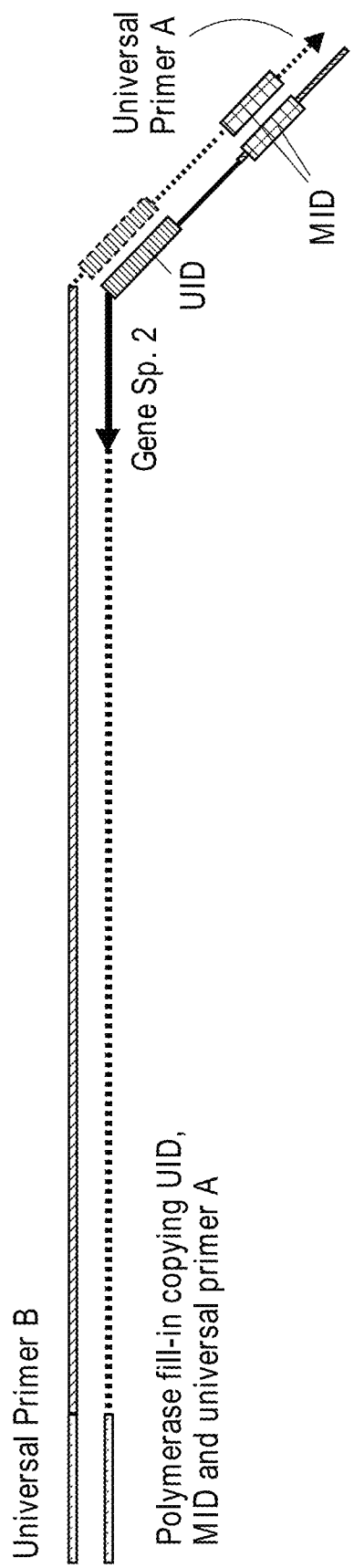
Figure 3D:
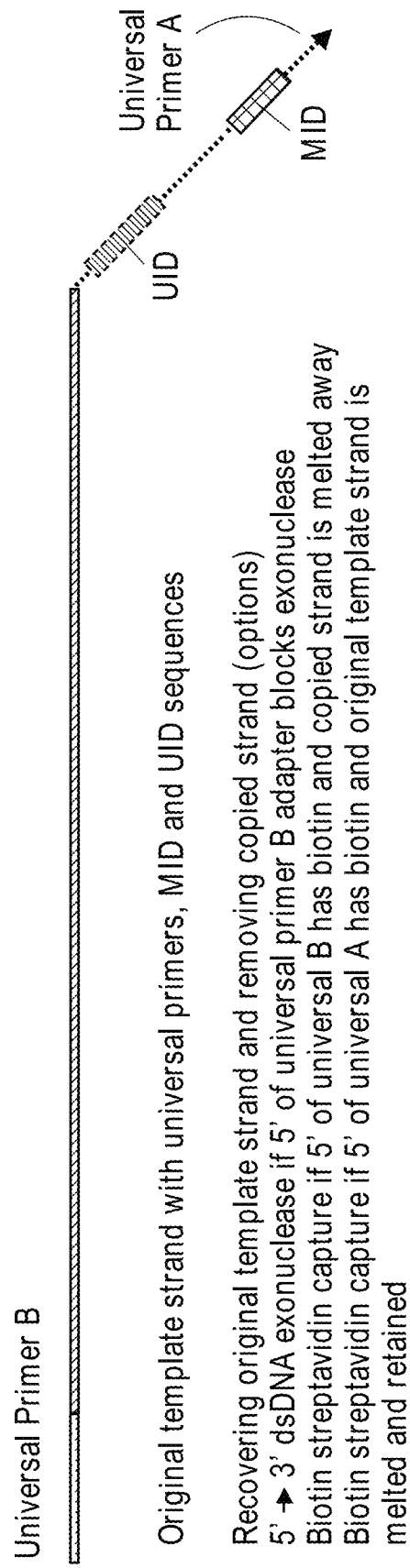

The present invention provides a primer extension target enrichment (PETE) method that includes two unidirectional primers and compositions for performing and using the unidirectional double primer PETE (UD-PETE) method. The use of two unidirectional primers increases the stringency of the enrichment step as compared to methods that require only a single primer or single bait for enrichment of each structurally distinct target polynucleotide. Thus, in some cases, the UD-PETE method provides improved or synergistic target enrichment in comparison to other target enrichment methods such as, e.g., single primer extension target enrichment methods.

Moreover, in contrast to multiplex PCR based methods in which multiple first and second amplification primers are in the same reaction mixture at the same time, the UD-PETE method can include a step of removing un-extended first primers before introducing second primers into a reaction mixture. Thus, in some cases, the method can reduce or eliminate competition between first and second primers. As such, in some cases, the first or second primers, or both can be used at significantly higher concentrations in the UD-PETE reaction mixture as compared to, e.g., multiplex PCR based methods. Additionally, or alternatively, an increased number of first or second primers can be used in the FP-PETE reaction mixture as compared to, e.g., multiplex PCR based methods.

In one embodiment, a first primer is hybridized to a 3' region of a single-stranded target polynucleotide and extended with a DNA polymerase. A second primer can be hybridized to a 3' region of the same single-stranded target polynucleotide that is 3' of the region to which the first primer hybridized. The second primer can then be extended with a DNA polymerase. Thus, the first and second primer are both hybridized to the same end and extended in the same direction (i.e., unidirectionally) relative to the target polynucleotide.

In a further embodiment, the first target-specific primer sequence and the second target-specific primer sequence can be provided as parts of a single oligonucleotide wherein the first target-specific primer sequence and the second target-specific primer sequence are linked and separated by at least one non-conventional base (e.g., selected from deoxyuracil, deoxyinosine, Int 1',2'-Dideoxyribose) that can be cleaved without cleaving naturally-occurring DNA in the same reaction. The oligonucleotide is used as the first-target-specific primer in a first extension reaction. After the first extension reaction is completed, the oligonucleotide can be treated with an endonuclease that targets the non-conventional base(s) to release the second target-specific primer sequence, which will have a 3'-OH end that is available for primer extension. The second target-specific primer can then be used in a strand displacement reaction as described above and elsewhere herein to generate the second target-specific primer extension product.

II. Methods

Described herein are unidirectional double primer extension target enrichment methods (UD-PETE) for enriching a target polynucleotide from a sample.

a. Forming a First Primer Extension Product

In some embodiments, the methods include a) providing a reaction mixture containing the sample and a first target-specific primer, wherein the sample contains a single-stranded target polynucleotide having 3' and a 5' end and a plurality of structurally different single-stranded non-target polynucleotides. In some embodiments, the methods further include b) hybridizing a first target-specific primer to the single-stranded target polynucleotide in the reaction mixture. Generally, the first target-specific primer is hybridized to a first hybridizing region of the single-stranded target polynucleotide that is far enough in the 5' direction from the 3' end of the single-stranded target polynucleotide that a second unidirectional primer can be hybridized to second hybridizing region of the target polynucleotide that is 3' of the first hybridizing region and does not overlap with the first hybridizing region. For example in some cases, the first target-specific primer hybridizes at least 6 nucleotides from the 3' end of the single-stranded target polynucleotide. In some cases, the first target-specific primer hybridizes at least 7, 8, 9, 10, 11, 12, 13, 14, 15, 16, 17, 18, 19, 20, 21, 22, 23, 24, 25, 26, 27, 28, 29, or 30 nucleotides from the 3' end of the single-stranded target polynucleotide. The target polynucleotide can in some embodiments comprise universal adaptor sequences on either end of the polynucleotide.

In some cases, the first target-specific primer hybridizes to the 5'-most nucleotide of the target polynucleotide. In some cases, the first target-specific primer hybridizes to the penultimate 5' nucleotide of the target polynucleotide, but not the 5'-most nucleotide of the target polynucleotide. In some cases, the first target-specific primer hybridizes to a region that is within 10 or 100 nucleotides of the 5'-most nucleotide of the target polynucleotide. In some cases, the first target-specific primer hybridizes to a region that is at least 6 nucleotides from the 3' end of the target polynucleotide and more than 100 nucleotides 3' to the 5'-most nucleotide of the target polynucleotide.

In some cases, the first target-specific primer hybridizes to a region of the target polynucleotide that is at least 6 nucleotides and no more than 500 nucleotides from the 3' end of the target polynucleotide, at least 8 nucleotides and no more than 500 nucleotides from the 3' end of the target polynucleotide, at least 10 nucleotides and no more than 500 nucleotides from the 3' end of the target polynucleotide, at least 12 nucleotides and no more than 500 nucleotides from the 3' end of the target polynucleotide, at least 15 nucleotides and no more than 500 nucleotides from the 3' end of the target polynucleotide, or at least 20 nucleotides and no more than 500 nucleotides from the 3' end of the target polynucleotide. In some cases, the first target-specific primer hybridizes to a region of the target polynucleotide that is at least 6 nucleotides and no more than 100 nucleotides from the 3' end of the target polynucleotide, at least 8 nucleotides and no more than 100 nucleotides from the 3' end of the target polynucleotide, at least 10 nucleotides and no more than 100 nucleotides from the 3' end of the target polynucleotide, at least 12 nucleotides and no more than 100 nucleotides from the 3' end of the target polynucleotide, at least 15 nucleotides and no more than 100 nucleotides from the 3' end of the target polynucleotide, at least 20 nucleotides and no more than 100 nucleotides from the 3' end of the target polynucleotide, at least 6 nucleotides and no more than 50 nucleotides from the 3' end of the target polynucleotide, at least 8 nucleotides and no more than 50 nucleotides from the 3' end of the target polynucleotide, at least 10 nucleotides and no more than 50 nucleotides from the 3' end of the target polynucleotide, at least 12 nucleotides and no more than 50 nucleotides from the 3' end of the target polynucleotide, at least 15 nucleotides and no more than 50 nucleotides from the 3' end of the target polynucleotide, or at least 20 nucleotides and no more than 50 nucleotides from the 3' end of the target polynucleotide.

In some embodiments, the method further includes c) extending the hybridized first target-specific primer with a DNA polymerase to form a first double-stranded product comprising the target polynucleotide hybridized to the extended first target-specific primer. The hybridized target polynucleotide of the double-stranded product can include a single-stranded overhang region at the 3' end. The length of the single-stranded overhang region at the 3' end can be, at least in part, determined by the distance between the 3' end and the position at which the first target-specific primer hybridizes to the target polynucleotide. Thus, a first target-specific primer that hybridizes at least 6 nucleotides from the 3' end of the single-stranded target polynucleotide and is subsequently extended by a DNA polymerase can produce a double-stranded product having a hybridized target polynucleotide with a single-stranded overhang region of at least 6 consecutive nucleotides at the 3' end.

As such, in some cases, the single-stranded overhang region of the double-stranded product produced by extension of the first target-specific primer can have a length of, or of at least, 7, 8, 9, 10, 11, 12, 13, 14, 15, 16, 17, 18, 19, 20, 21, 22, 23, 24, 25, 26, 27, 28, 29, or 30 nucleotides. In some cases, the single-stranded overhang region of the double-stranded product produced by extension of the first target-specific primer can have a length of, or of at least, 6 to 500, 8 to 500, 10 to 500, 12 to 500, 15 to 500, 20 to 500, 6 to 100, 8 to 100, 10 to 100, 12 to 100, 15 to 100, 20 to 100, 6 to 50, 8 to 50, 10 to 50, 12 to 50, 15 to 50, or 20 to 50 nucleotides. In some cases, the single-stranded overhang region of the double-stranded product produced by extension of the first target-specific primer can have a length of at least 40; 50; 100; 250; 500; 1,000; or 10,000 nucleotides.

In some embodiments, the method includes d) removing single-stranded target and non-target polynucleotides that are not hybridized to extended target-specific primer, if present from the reaction mixture. In some cases, the removing of d) includes removing un-extended first target-specific primers. In some cases, the removing of d) includes contacting single-stranded target and non-target polynucleotides with a 5' to 3' single-stranded exonuclease. In some cases, the removing of d) includes contacting single-stranded target and non-target polynucleotides, including un-extended first target-specific primers with a 5' to 3' single-stranded exonuclease.

In some embodiments, the first target-specific primers are labeled first target-specific primers, wherein the label is an affinity ligand covalently linked to the primer. Exemplary affinity ligands include, but are not limited to, biotin or a derivative thereof, such as iminobiotin. In some cases, the labeled first target-specific primers are immobilized to a solid surface. The labeled first target-specific primers can be immobilized before or after, or at the same time as, hybridizing to the single-stranded target polynucleotide in the reaction mixture. Alternatively, the labeled first target-specific primers can be immobilized after hybridizing to the single-stranded target polynucleotide in the reaction mixture and extending the hybridized first target-specific primer with the DNA polymerase.

In some embodiments, the first target-specific primer is covalently linked to an affinity ligand, hybridized to the target polynucleotide, and extended with a polymerase to produce an immobilized double-stranded product. In such embodiments, the removing single-stranded target and non-target polynucleotides that are not hybridized to extended target-specific primer of d) can include washing away non-immobilized polynucleotides. In some cases, the removing single-stranded target and non-target polynucleotides that are not hybridized to extended target-specific primer of d) can include removing the immobilized double-stranded product from the reaction mixture; and, optionally, placing the immobilized double-stranded product into a different reaction mixture.

In some embodiments, the first target-specific primers are not labeled with an affinity ligand and at least some free nucleotides are provided that are linked to an affinity label such that at least some nucleotides that are incorporated into the extended target-specific primer are covalently linked to an affinity label, for example an affinity ligand including, but not limited to, biotin or a derivative thereof, such as iminobiotin.

In some embodiments, universal adapter sequences can be attached to the double-stranded product prior to formation of the second primer extension product discussed below. For example, universal adapter sequences can be attached by ligation. In some embodiments, the universal adapter sequences can include one or more barcode sequences (e.g., a sample (MID) barcode).

In some embodiments, the first target-specific primer sequence (as described above) is provided as a 3' sequence of an oligonucleotide that also comprises the second target-specific primer sequence at the 5' end of the oligonucleotide. The first and second target-specific primer sequences are linked and separated by one or more non-conventional bases that can be cleaved without cleaving the DNA in the reaction. Exemplary non-conventional bases can include but are not limited to deoxyuracil, deoxyinosine, and Int 1',2'-Dideoxyribose. The oligonucleotide can then hybridized to a target polynucleotide and extended with a polymerase to form the first primer extension product. As discussed elsewhere subsequently, the oligonucleotide can be cleaved to release the second target-specific primer from the oligonucleotide, thereby allowing the second target-specific primer to be available for primer extension.

b. Forming a Second Primer Extension Product

In some embodiments, the method further includes e) hybridizing a 3' hybridizing region of a second target-specific primer to the single-stranded overhang region at the 3' end of the hybridized target polynucleotide. In some cases, the second target-specific primer contains a 3' hybridizing region that hybridizes to the target polynucleotide and a 5' region that does not hybridize to the target polynucleotide. In some cases, the 5' region that does not hybridize to the target polynucleotide contains a barcode (e.g., a UID barcode) region. In some cases, the second target-specific primer contains a 5'-terminal phosphate. In such embodiments, a polymerase extension product of the second target-specific primer can therefore contain a 5'-terminal phosphate.

In some cases, the 5' region that does not hybridize to the target polynucleotide additionally, or alternatively, contains a [SPLINT] region. The [SPLINT] region can include an adapter hybridization site of at least 2 nucleotides in length. In some cases, the adapter hybridization site is at least 4 nucleotides in length, at least 6 nucleotides in length, at least 8 nucleotides in length, from 2 to 10 nucleotides in length, or from 2 to 8 nucleotides in length. The [SPLINT] region can be complementary to a single-stranded 5' overhang region of a double-stranded adapter, such that when the single-stranded 5' overhang region of the double-stranded adapter hybridizes to the [SPLINT] region, a 3'-OH of the adapter can be ligated to a 5' terminal phosphate of a second target-specific primer or an extended second target-specific primer (e.g., an extended second target-specific primer hybridized to a target polynucleotide). In some embodiments, [SPLINT] comprises or consists of 6 consecutive nucleotides that are complementary to a single-stranded 5' overhang region of a double-stranded adapter. In some embodiments, [SPLINT] comprises or consists of the sequence CGA TCT.

In some embodiments, the nucleotide at the 3' end of the second target-specific primer hybridizes to the 5'-most nucleotide of the single-stranded overhang region. In some cases, the nucleotide at the 3' end of the second target-specific primer hybridizes to a nucleotide of the single-stranded overhang region of the hybridized target polynucleotide that is at least 1 nucleotide 3' of the 5'-most nucleotide of the single-stranded overhang region. In some cases, the nucleotide at the 3' end of the second target-specific primer hybridizes to a nucleotide of the single-stranded overhang region of the hybridized target polynucleotide that is, or is at least, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides 3' of the 5'-most nucleotide of the single-stranded overhang region.

In some cases, the gap on the target polynucleotide between the 3' end of the second target-specific primer hybridized to the target polynucleotide and the 5'-most nucleotide of the first target-specific primer (e.g., extended first target-specific primer) that is hybridized to the target polynucleotide is from 0 to about 10,000 or more nucleotides, from about 1 to about 10,000 or more nucleotides, from 0 to about 1,000 or more nucleotides, from 1 to about 1,000 or more nucleotides, from about 1 to about 500 nucleotides, from about 3 to about 500 nucleotides, from about 5 to about 500 nucleotides, or from about 10 to about 500 nucleotides in length. In some cases, the gap is less than 1,000; 500; 250; 100; 50; or 10 nucleotides in length.

In some cases, the second target-specific primer hybridizes to a region of the target polynucleotide that overlaps with the region to which the first target-specific primer hybridizes. The number of overlapping targeted nucleotides (nucleotides of the target polynucleotide that hybridize to both first and second target-specific primer) can be 0 (i.e., no overlap), 1, 2, 3, 4, 5, 6, 7, 8, 9, 10, 11, or 12, e.g., from about 1 to about 12, from about 1 to about 10, from about 1 to about 8, from about 1 to about 6, or from about 1 to about 4.

In some embodiments, the method further comprises f) extending the hybridized second target-specific primer with a DNA polymerase, thereby forming a second double-stranded product that contains the target polynucleotide hybridized to an extended second target-specific primer. The second double-stranded product can have a 3' single-stranded overhang region, a 5' single-stranded overhang region, or a combination thereof.

For example, in some cases, the second target-specific primer hybridizes to a region of the target polynucleotide that is, or is at least, one nucleotide 5' of the 3' end of the target polynucleotide. In such cases, the second double-stranded product can contain a 3' single-stranded overhang region having a length of, or of at least, one nucleotide. In some cases, the 3' single-stranded overhang region of the second double-stranded product can have a length of, or of at least, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some cases, the 3' single-stranded overhang region of the second double-stranded product can have a length of, or of at least, 6 to 500, 8 to 500, 10 to 500, 12 to 500, 15 to 500, 20 to 500, 6 to 100, 8 to 100, 10 to 100, 12 to 100, 15 to 100, 20 to 100, 6 to 50, 8 to 50, 10 to 50, 12 to 50, 15 to 50, or 20 to 50 nucleotides.

As described above, the second target-specific primer can contain a 3' hybridizing region that hybridizes to the target polynucleotide and a 5' region that does not hybridize to the target polynucleotide. In such cases, the second double-stranded product produced by extending hybridized second target-specific primer can contain a 5' single-stranded overhang region corresponding to the 5' region of the primer that does not hybridize to the target polynucleotide. In some cases, the 5' region of the primer that does not hybridize to the target polynucleotide contains a barcode (e.g., a UID barcode). In such cases, the extending of the second target-specific primer can thereby produce a second double-stranded product containing the target polynucleotide hybridized to the extended second target-specific primer, wherein the extended second target-specific primer comprises a complement of at least a portion of the target polynucleotide, and a single-stranded 5' overhang region comprising the barcode.

In some cases, the DNA polymerase exhibits strand displacement activity. In some cases, the DNA polymerase exhibits 5'-3' DNA exonuclease activity that digests a single strand of a double-stranded DNA substrate (referred to herein as 5'-3' double-stranded DNA exonuclease activity) or double-stranded DNA exonuclease activity. In some cases, the DNA polymerase exhibits both strand displacement and 5'-3' double-stranded DNA exonuclease activity. In some cases, the strand displacement, 5'-3' double-stranded DNA exonuclease activity, or combination thereof, can displace target polynucleotide (e.g., original target polynucleotide molecule from a provided sample) into solution.

For example, in some cases, a first double-stranded product containing the target polynucleotide hybridized to the extended first target-specific primer is immobilized on a solid surface, e.g., by affinity capture of a ligand (e.g., biotin or a derivative thereof) covalently linked to the extended first target-specific primer. In such cases, the strand displacement activity of the DNA polymerase that extends the hybridized second target-specific primer displaces the target polynucleotide from the sample into solution. Alternatively, 5'-3' exonuclease activity can degrade extended first target-specific primer that is immobilized by affinity capture and hybridized to target polynucleotide, wherein the 5'-3' exonuclease activity thereby releases the target polynucleotide into solution.

In some cases, single-stranded extended second target-specific primer can be recovered from the second double-stranded product, producing a recovered single-stranded extended second target-specific primer. In some cases, the extended second target-specific primer can be recovered from the second double-stranded product before attachment of a first or second universal adapter. In some cases, the extended second target-specific primer can be recovered from the second double-stranded product after attachment of a first universal adapter and before attachment of a second universal adapter. In some cases, the extended second target-specific primer can be recovered from the second double-stranded product after attachment of a first universal adapter and a second universal adapter.

For example, in some cases, the second target-specific primer is blocked at a 5' end, such that the extended second target-specific primer is resistant to 5'-3' exonuclease activity. In such cases, the second double-stranded product can be contacted with a single-stranded, double-stranded, or single and double-stranded 5'-3' exonuclease to degrade the target polynucleotide in the second double-stranded product. In some cases, the single and double-stranded 5'-3' exonuclease is provided by the same enzyme. In other cases, the contacting the second double-stranded product with a single and double-stranded 5'-3' exonuclease is performed by contacting the second double-stranded product with two different enzymes. In some cases, the target polynucleotide in the second double-stranded product is degraded by contacting with 5'-3' exonuclease activity and purifying the single-stranded extended second target-specific primer (e.g., by column, bead, resin, batch, gel, or membrane-based nucleic acid purification methods including, but not limited to, solid-phase reversible immobilization methods (SPRI)).

In some embodiments, the target polynucleotide is RNA (e.g., mRNA). In such embodiments, extending the hybridized first target-specific primer is performed with an RNA-dependent DNA polymerase, and the first double-stranded product thus formed is a cDNA/RNA hybrid. Similarly, extending the hybridized second target-specific primer thus forms a second double-stranded product that is also a cDNA/RNA hybrid. In such cases, the extended second target-specific primer can be recovered by digesting the RNA of the cDNA/RNA hybrid with an enzyme that exhibits RNase H activity.

Figure 5:
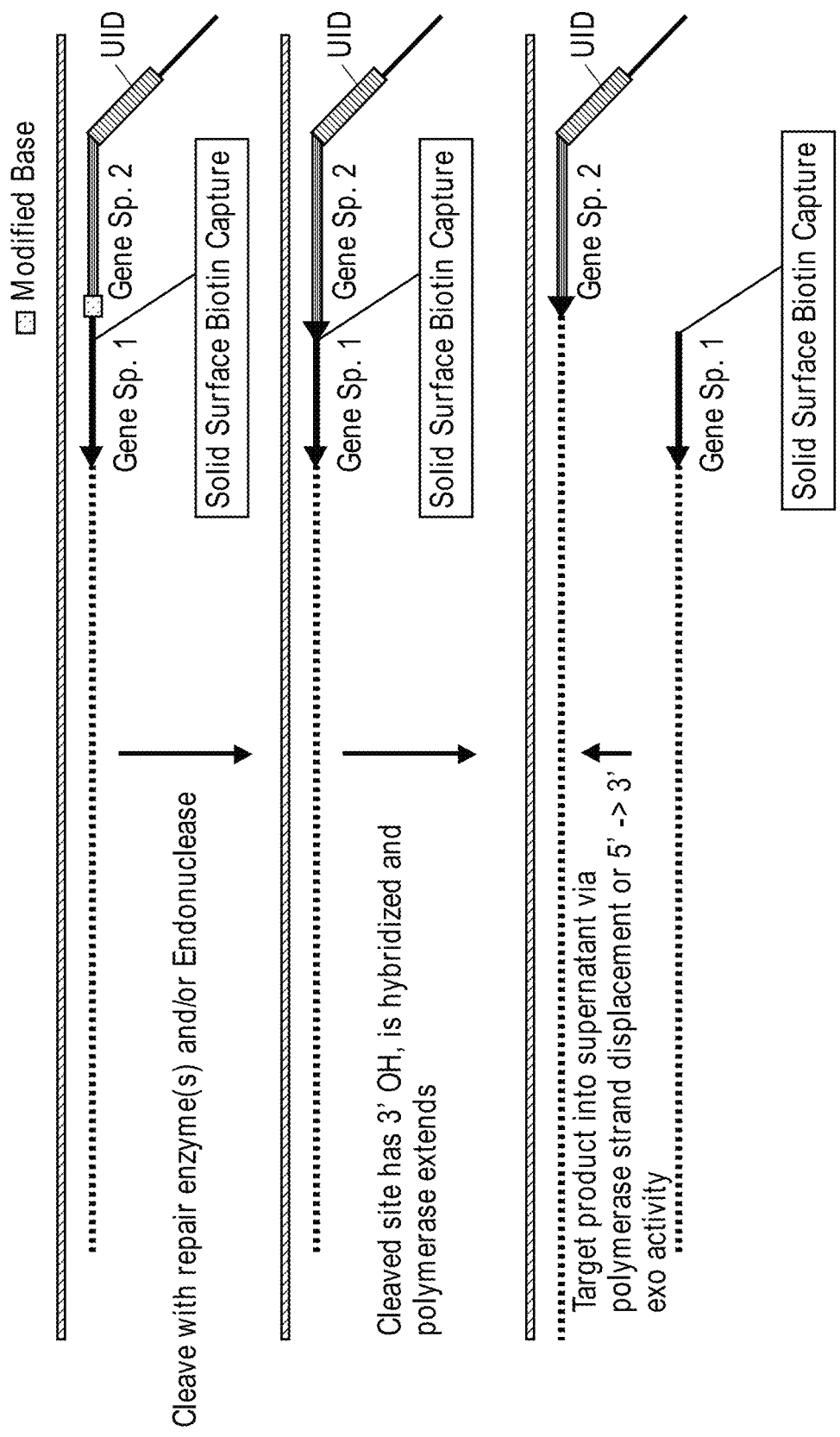
FIG. 5 illustrates an alternate embodiment of UD-PETE. In this embodiment, an oligonucleotide comprising a first target-specific primer sequence is linked to a second target-specific primer sequence by one or more non-conventional bases (also referred to herein as "modified bases." The oligonucleotide is hybridized to a target polynucleotide and extended with a polymerase to form the first primer extension product (top panel). The oligonucleotide, and thus the first primer extension product, is optionally biotinylated. Biotinylated oligonucleotide or first primer extension product is optionally captured onto an anti-biotin (e.g., streptavidin) coated solid surface. The first primer extension primer is contacted with an endonuclease that targets the non-conventional base(s) to release the second target-specific primer sequence having a 3'-OH. The second target-specific primer can then be hybridized to the target polynucleotide and extended with a polymerase having strand displacement activity to generate a second primer extension product. The first primer extension product is thus displaced or digested. Universal adapters can be subsequently added to the second primer extension product, (not depicted in FIG. 5) as shown for example in FIGS. 1D-E.
Figure 6:
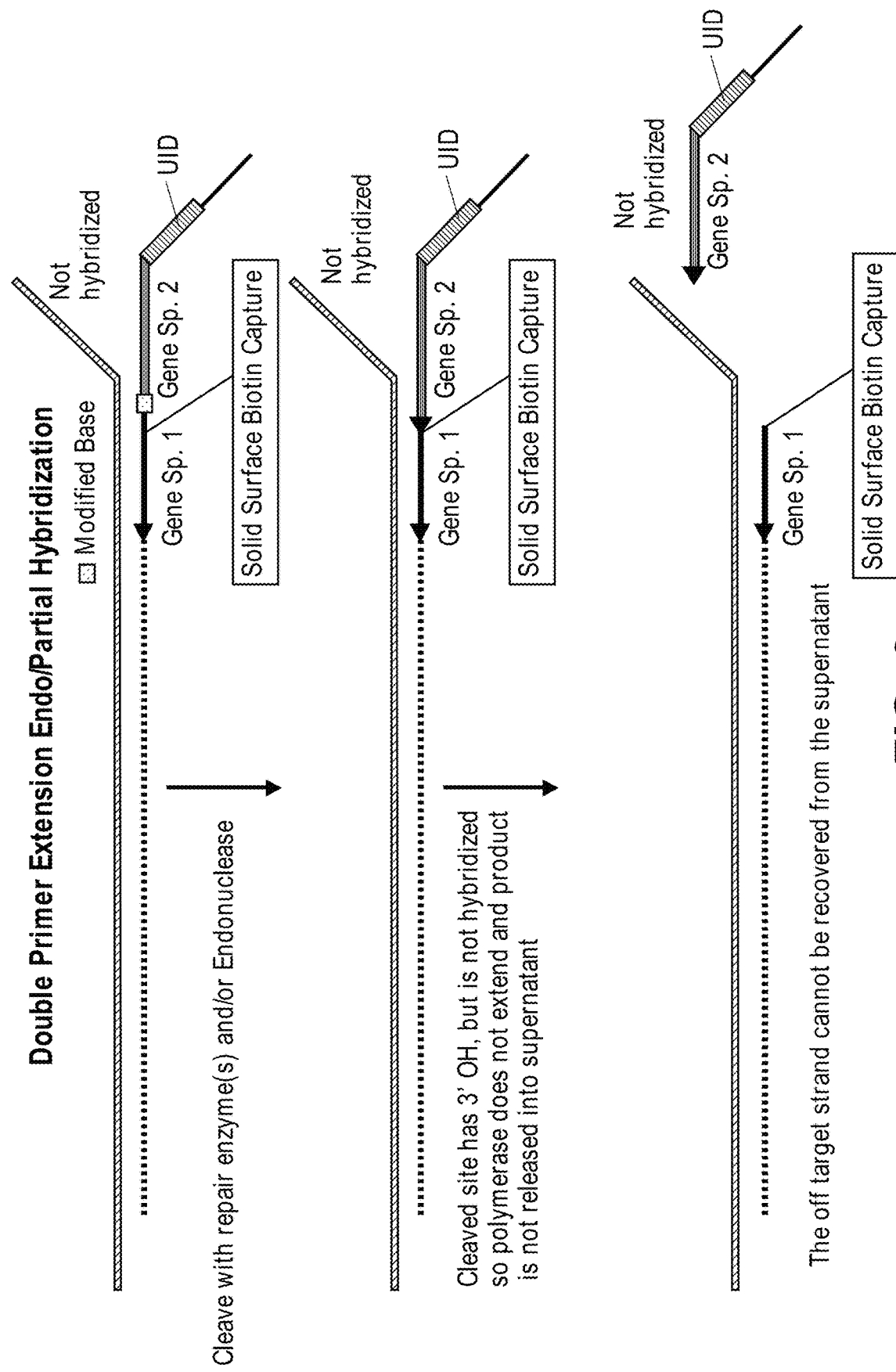
FIG. 6 illustrates an alternate embodiment of that shown in FIG. 0.5, wherein a non-target polynucleotide is hybridized with the oligonucleotide. The first primer sequence hybridizes to the non-target polynucleotide but that second primer sequence does not hybridize and thus a second primer extension product is not formed.

In embodiments in which the first and second target specific primers are provided as parts of a single oligonucleotide (with the first target-specific primer sequencing being at the 3' end of the oligonucleotide), the first and second target-specific primers sequences can be separated following initial priming based on the first target-specific primer sequence. See, e.g., FIG. 5. For example, one or more non-conventional bases separating the first and second target-specific primer sequences can be cleaved to separate the second target-specific primer sequence from the first target-specific primer sequence, leaving a 3'-OH moiety on the second target-specific primer to allow for subsequent primer extension from the second target-specific primer. For example, an endonuclease that targets the non-conventional base can be used to release the second primer from the oligonucleotide such that the second primer has a free 3'-OH. Tth Endonuclease IV, Endonuclease IV or Endonuclease VIII. Exemplary endonucleases can include but are not limited to, Tth Endonuclease IV, Endonuclease IV, or *E. coli* endonuclease VIII (which cleave at abasic sites) or *E. coli* endonuclease V (which cleaves at deoxyinosine sites). In the embodiment where deoxyuracil is incorporated, the reaction mixture can be contacted with uracil-N-DNA glycosylase (UNG). UNG cleaves the uracil from DNA leaving an abasic site. In some embodiments, the non-conventional base that introduces the abasic site is Int 1',2'-Dideoxyribose. The sample can then be further contacted with an endonuclease cleaving the DNA at abasic sites. The released second target-specific primer can then be hybridized to the target polynucleotide and extended with a polymerase having strand displacement activity as described above, thereby releasing or removing the first primer extension product and generating the second primer extension product.

c. Attachment of Universal Adapters

In some embodiments, the methods further include attaching a first universal adapter, or a first and second universal adapter to the second double-stranded product. Additionally or alternatively, the methods further include attaching a first universal adapter, or a first and second universal adapter to a recovered single-stranded extended second target-specific primer. In some cases, the first universal adapter is attached to the second double-stranded product, the first adapter-attached extended second target-specific primer is recovered from the double-stranded product, and a second universal adapter is attached to the first adapter-attached and recovered single-stranded extended second target-specific primer.

In some cases, attachment of a first universal adapter, second universal adapter, or the combination thereof includes ligating the one or more adapter(s) to the second double-stranded product, or recovered single-stranded extended second target-specific primer. In some cases, the ligation can require a 5'-terminal phosphate on a donor strand. In some cases a 5'-terminal phosphate is provided by using a second target-specific primer having a 5'-terminal phosphate. In some cases, a 5'-terminal phosphate is provided by contacting the second double-stranded product, or recovered single-stranded extended second target-specific primer with an enzyme that can append a 5'-terminal phosphate to a polynucleotide (e.g., T4 polynucleotide kinase or a 3' phosphatase minus derivative thereof).

In some cases, a first universal adapter is attached to a recovered single-stranded extended second target-specific primer by ligation. For example, a first universal adapter can be a splint adapter that is ligated to a recovered single-stranded extended second target-specific primer. Splint adapters can contain a double stranded region and a 5' single-stranded overhang region, wherein the 5' single-stranded overhang region is complementary to and hybridizes under hybridization conditions with the [SPLINT] region of the recovered single-stranded extended second target-specific primer. The splint adapter can be configured to hybridize to the [SPLINT] region such that a 3'-OH of the adapter (e.g., on the opposite strand as the 5' single-stranded overhang region of the splint adapter) can be ligated to a 5'-terminal phosphate of the recovered single-stranded extended second target-specific primer. The 5' single-stranded overhang region of the splint adapter can be at least 2 nucleotides in length, at least 4 nucleotides in length, at least 6 nucleotides in length, at least 8 nucleotides in length, from 2 to 10 nucleotides in length, or from 2 to 8 nucleotides in length. In some embodiments, the 5' single-stranded overhang region comprises or consists of 6 consecutive nucleotides that are complementary to a [SPLINT] region of the recovered single-stranded extended second target-specific primer. In some embodiments, the 5' single-stranded overhang region comprises or consists of the sequence AGA TCG.

In some cases, the first universal adapter can contain a barcode. For example, the first universal adapter can contain an MID barcode. Thus, attachment (e.g., ligation) of a first universal adapter can attach an MID barcode, a first universal primer binding site, or a combination thereof, to the recovered single-stranded extended second target-specific primer. In some cases, the attachment (e.g., ligation) of a first universal adapter can attach an MID barcode, a first universal primer binding site, or a combination thereof, to the second double-stranded product.

In some cases, a second universal adapter is attached to a recovered single-stranded extended second target-specific primer (e.g., after attachment of first universal adapter) by ligation. For example, a 3' end of a recovered single-stranded extended second target-specific primer (e.g., after attachment of first universal adapter) can be contacted with a terminal transferase, thereby appending a 3' tail region to the 3' end of the recovered single-stranded extended second target-specific primer and generating a tailed single-stranded extended second target-specific primer. The tailed single-stranded extended second target-specific primer can be contacted with a second universal adapter that is a splint adapter having a double-stranded region and a 3' single-stranded overhang region that is complementary to the 3' tail region of the tailed single-stranded extended second target-specific primer, thereby hybridizing the second universal adapter to the tailed single-stranded extended second target-specific primer. The hybridized second universal adapter can be hybridized such that a 5'-terminal phosphate of the adapter is adjacent to, and can be ligated with, a 3'-terminal OH of the tailed single-stranded extended second target-specific primer. Thus, the 5' end of the hybridized second universal adapter can be contacted with a ligase and ligated to the 3' tail region of the tailed single-stranded extended target-specific primer.

In some cases, the 3' tail region contains, or contains at least about, 2, 3, 4, 5, 6, 7, 8, 9, 10, 11, 12, 13, 14, 15, 16, 17, 18, 19, or 20 consecutive nucleotides of the same sequence. In some cases, the 3' tail region contains from 2 to about 20, from 2 to about 15, from 2 to about 12, from 2 to about 10, or from 2 to about 8 consecutive nucleotides of the same sequence. In some cases, the 3' tail region contains from 3 to about 20, from 3 to about 15, from 3 to about 12, from 3 to about 10, or from 3 to about 8 consecutive nucleotides of the same sequence.

First, second, or first and second universal adapters can be attached by tagmentation. Methods and compositions for tagmentation include, but are not limited to those described in U.S. Pat. Nos. 5,965,443; 6,437,109; 7,083,980; 7,608, 434; and 9,238,671. In an exemplary embodiment, a second double-stranded product is contacted with a transposase (e.g., a Tn5 transposase or mutant thereof) loaded with first and second adapters, or a pool of first adapter-loaded transposase and second adapter-loaded transposase. The adapter-loaded transposase or pool of adapter-loaded transposases is allowed to fragment the second double-stranded product and covalently link first or second adapters to the end of the fragments, resulting in a pool of: i) fragments having first adapters on both ends; ii) fragments having second adapters on both ends; iii) fragments having a first adapter on an first end and a second adapter on a second end.

Adapter-attached second double-stranded product, recovered single-stranded extended second target-specific primer, or tagmentation fragments thereof, can contain a first universal primer binding site and a second universal primer binding site or complement thereof. Thus, the adapter-attached polynucleotide can be amplified by universal PCR. In one embodiment, a single-stranded polynucleotide (e.g., recovered single-stranded extended second target-specific primer) contains one universal primer binding site at a 3' end and a complement of a different universal primer binding site at the 5' end. In such embodiments, a universal primer can be hybridized to the universal primer binding site and extended with a polymerase, thereby producing a double-stranded product having both first and second universal primer binding sites. In some embodiments, the single-stranded polynucleotide has a second universal primer binding site at a 3' end (e.g., attached by ligation of second universal adapter) and a complement of a first universal primer binding site at a 5' end (e.g., attached by ligation of first universal adapter).

d. Barcoding Original Target Polynucleotide

Described above are methods of UD-PETE in which a barcoded (e.g., UID barcoded) second target-specific primer is hybridized to target polynucleotide, extended, and the extension product recovered. In such embodiments, the barcode is incorporated into the extended second target-specific primer. Thus, polymerase errors that are introduced during the extension of second target-specific primer cannot be distinguished from true variants in the sample from which the target polynucleotide is provided. Described herein are methods of UD-PETE in which a barcoded (e.g., UID barcoded) second target-specific primer is used to attach a barcode (e.g., UID barcode) directly to the original target polynucleotide. Thus, polymerase errors are not introduced into the target polynucleotide sequence.

The methods described herein can include preliminary steps of first target-specific hybridization, extension, and second target-specific hybridization as described above. Moreover, the methods described herein can include subsequent steps of universal adapter attachment (e.g., ligation, tagmentation, etc.) as described above.

In some embodiments, the barcoded (e.g., UID barcoded) second target-specific primer is hybridized to target polynucleotide and extended to produce a second double-stranded product wherein the target polynucleotide in the second double-stranded product contains a 3' single-stranded overhang region having a length of at least 1 nucleotide. Alternatively, the barcoded (e.g., UID barcoded) second target-specific primer can be hybridized to target polynucleotide and extended to produce a second double-stranded product wherein the target polynucleotide in the second double-stranded product does not have a 3' single-stranded overhang region. For example, the barcoded (e.g., UID barcoded) second target-specific primer can hybridize to the target polynucleotide such that the 3' terminal nucleotide of the target polynucleotide is hybridized to a nucleotide of the 3' hybridizing region (e.g., the 5'-terminal nucleotide of the 3' hybridizing region) of the second target-specific primer.

In embodiments wherein the target polynucleotide in the second double-stranded product contains a 3' single-stranded overhang region having a length of at least 1 nucleotide, the 3' single-stranded overhang region can be contacted with a 3'-5' single-stranded DNA exonuclease to remove the overhang region. For example, the 3' single-stranded overhang region can be contacted with Exo I to digest the overhang region. As another example, the 3' single-stranded overhang region can be contacted with T4 polymerase to digest the overhang region.

Second double-stranded product wherein the target polynucleotide in the second double-stranded product does not have a 3' single-stranded overhang region (e.g., after digestion with a 3'-5' single-stranded DNA exonuclease) can then be contacted with a DNA polymerase to extend the 3' end of the original target polynucleotide. The extension reaction can be templated by the 5' overhang region of the extended second target-specific primer. Thus, if the second target-specific primer is barcoded (e.g., UID barcoded) the extension can attach the barcode (i.e., a complement of the barcode sequence of the second target-specific primer) to a 3' end of the original template strand. Similarly, if the second target-specific primer contains a [SPLINT] region, the extension can attach a [SPLINT] region (i.e., a complement of the [SPLINT] region of the second target-specific primer) to a 3' end of the original template strand. In some cases, the extension incorporates a barcode and a [SPLINT] region to a 3' end of the original template strand. In some cases, the extension incorporates from 5' to 3' a barcode and a [SPLINT] region into a 3' end of the original template strand.

In some embodiments, a first universal adapter is attached to the second double-stranded product before digestion of the 3' single-stranded overhang region, if present. In other embodiments, a first universal adapter is attached to the second double-stranded product after digestion of the 3' single-stranded overhang region, if present. In some cases, a first universal adapter is attached to the second double-stranded product after incorporation of a barcode (e.g., UID barcode), a [SPLINT] region, or a barcode and [SPLINT] region by polymerase-mediated extension of the 3' end of the target polynucleotide in the second double-stranded product. In some cases, a first universal adapter is attached to the second double-stranded product before incorporation of a barcode (e.g., UID barcode), a [SPLINT] region, or a barcode and [SPLINT] region by polymerase-mediated extension of the 3' end of the target polynucleotide in the second double-stranded product.

In an exemplary embodiment, a first universal adapter (e.g., double-stranded first universal adapter) is attached (e.g., ligated) to an end of the second double-stranded product that contains the 3' end of the extended second target-specific primer and the 5' end of the target polynucleotide. In some cases, a double-stranded first universal adapter having a blunt end is ligated to the end of the second double-stranded product that contains the 3' end of the extended second target-specific primer in a blunt end ligation reaction. Alternatively, a double-stranded first universal adapter having a cohesive end (i.e., complementary single-stranded overhang) can be ligated to a compatible cohesive end of the second double-stranded product that contains the 3' end of the extended second target-specific primer in a cohesive-end ligation reaction.

For example, in some cases, the 3' end of the extended second target-specific primer contains one, at least one, two, or at least two consecutive adenine nucleotides and the double-stranded first universal adapter contains one, at least one, two, or at least two consecutive thymine nucleotides for T-A ligation to the end of the second double-stranded product. In some cases, a DNA polymerase is selected for second target-specific primer extension to preferentially produce either blunt or cohesive ends and a corresponding blunt or cohesive end first universal adapter is used. Ligation can be performed by contacting the first universal adapter and second double-stranded product with a ligase (e.g., T4 DNA ligase).

A first universal adapter and a second universal adapter are typically attached (e.g., ligated) to opposite ends of the second double-stranded product. In some cases, the first and second universal adapter are attached before extension of the 3' end of the target polynucleotide in the second double-stranded product. In some cases, the first universal adapter is attached before the extension and the second universal adapter is attached after the extension. In some cases, the first universal adapter is attached to the end of the second double-stranded product containing the 3' end of the extended second target-specific primer, and the second universal adapter is attached to the end of the second double-stranded product containing the 5' end of the extended second-target specific primer. Alternatively, the first universal adapter is attached to the end of the second double-stranded product containing the 5' end of the extended second target-specific primer, and the second universal adapter is attached to the end of the second double-stranded product containing the 3' end of the extended second-target specific primer.

In some embodiments, the second target-specific primer contains a UID barcode and [SPLINT] region and a universal adapter containing an MID barcode and universal primer binding site is attached (e.g., ligated) to the 5' end of the extended second target-specific primer in the second double-stranded product. In such cases, attachment of the MID barcoded universal adapter before extension of the 3' end of the target polynucleotide can incorporate the universal primer site and MID barcode into the original target polynucleotide. In some cases, the MID barcoded universal adapter is attached first, and a different universal adapter is attached to the other end of the second double-stranded product second. However, the relative order in which universal adapters are attached to opposite ends of second-double stranded product is interchangeable for different workflows.

e. Recovering Original Target Polynucleotide

In some embodiments, after first and second adapter are ligated, original single-stranded target polynucleotide is recovered. In some cases, the recovered original single-stranded target polynucleotide is barcoded. The recovered barcoded original single-stranded target polynucleotide can contain a UID, an MID, or a UID and an MID. In an exemplary embodiment, the recovered barcoded original single-stranded target polynucleotide contains from 5' to 3': a second universal primer binding site or complement thereof, an original target polynucleotide region that contains consecutive nucleotides from the original target polynucleotide molecule, a UID barcode, an MID barcode, and a first universal primer binding site or complement thereof.

In some embodiments, the barcoded original single-stranded target polynucleotide is recovered from the second double-stranded product by 5' to 3' double-stranded exonuclease digestion (e.g., digestion of the double-stranded product with an exonuclease enzyme that degrades a single strand of a double-stranded DNA substrate to produce a single-stranded product). In such embodiments, the universal adapter attached to the end of the second double-stranded product containing the 3' end of the extended second target-specific primer can be blocked at a 5' end such that the 5' end of the adapter-attached original target polynucleotide is blocked from 5' to 3' double-stranded exonuclease digestion. Alternatively, the universal adapter attached to the end of the second double-stranded product containing the 3' end of the extended second target-specific primer can be labeled (e.g., at a 5' end) with an affinity ligand (e.g., biotin) such that the second double-stranded product containing adapter-attached original target polynucleotide can be captured and the copied strand eluted away, e.g., by heating. As yet another alternative, the universal adapter attached to the end of the second double-stranded product containing the 5' end of the extended second target-specific primer can be labeled (e.g., at a 5' end) with an affinity ligand (e.g., biotin) such that the second double-stranded product containing adapter-attached original target polynucleotide can be captured and the original template strand eluted away, e.g., by heating or chemical elution (e.g., by contacting with an acid, or base, or nucleophile to disrupt the affinity between ligand and capture agent or cleave a link between affinity ligand and nucleic acid), and recovered.

In some embodiments, the barcoded original single-stranded target polynucleotide is recovered from the second double-stranded product through the use of endonucleases. Specifically, endonucleases are used to degrade the second primer extension product without degrading the original strand. Certain endonucleases are known to cleave the nucleic acid backbone (phosphodiester bonds) at specific sites. For example, *E. coli* endonuclease VIII cleaves at abasic sites while *E. coli* endonuclease V cleaves at deoxyinosine sites. In some embodiments, the non-conventional base introduces an abasic site that can be specifically cleaved without cleaving DNA in the same reaction. Exemplary enzymes that cleave abasic sites include, e.g., Tth Endonuclease IV, Endonuclease IV or Endonuclease VIII. In some embodiments, the non-conventional base that introduces the abasic site is Int 1',2'-Dideoxyribose. In some embodiments, one or both of first and second primer extension reactions are performed in the presence of non-conventional nucleotides that can be incorporated by the extending DNA polymerase and enable subsequent endonuclease digestion. In some embodiments, the extension reaction is performed in the presence of deoxyuracil triphosphate (dUTP). In some embodiments, dUTP is entirely replacing dTTP in the extension reaction. In other embodiments, a mixture of dUTP and dTTP is used. The ratio of dUTP to dTTP can be between 0:1, 1:1, 1:100. Following the incorporation of dU in place of some or all dT nucleotides in one or both of first and second primer extension products enables them to be digested with uracil-N-DNA glycosylase (UNG). UNG cleaves the uracil from DNA leaving an abasic site. In some embodiments, the reaction mixture comprising one or both of first and second primer extension products with abasic sites can be treated with an endonuclease cleaving DNA at abasic sites. In some embodiments, the endonuclease is *E. coli* endonuclease VIII. In some embodiments, one or both of first and second primer extension products with abasic sites can be cleaved non-enzymatically, e.g., by heat treatment. In some embodiments, the efficiency of the heat cleavage can be increased by the addition of polyamine compounds such as spermidine, spermine, triethylenetetramine, and trimethylenediamine, see U.S. Pat. No. 8,669, 061. In other embodiments, the extension reaction is performed in the presence of deoxyinosine triphosphate (dITP). Because dITP is incorporated by DNA polymerases opposite any base, dITP in the reaction mixture may partially or completely replace any one of dATP, dCTP, dGTP and dTTP. In some embodiments, dITP is simply added to the mixture of the dATP, dCTP, dGTP and dTTP without reducing the amount of any of the four bases. In some embodiments, the reaction mixture comprising one or both of first and second primer extension products with deoxyinosines (dI) can be treated with an endonuclease cleaving DNA at dI sites. In some embodiments, the endonuclease is $E.\ coli$ endonuclease V. In some embodiments, the DNA fragments resulting from exonuclease digestion are further digested with exonuclease or removed from the reaction mixture by any other means (e.g., size separation).

In some embodiments, the strand paired with the barcoded original single-stranded target polynucleotide (the second primer extension product) is not removed by endonucleases but is rendered non-amplifiable in the amplification step. In this embodiment, only the primer binding site contains non-conventional nucleotides such as deoxyuracil or deoxyinosine or Int 1',2'-Dideoxyribose. The endonuclease digestion degrades the primer binding site portion of the second primer extension product preventing primer annealing and amplification. In some embodiments, the primer is a universal primer. In this embodiment, an oligonucleotide containing the primer binding site is synthesized by any method known in the art that allows non-conventional nucleotides such as deoxyuracil (dU) or deoxyinosine (dI) or Int 1',2'-Dideoxyribose to be incorporated. In the embodiment where dU is incorporated, the reaction mixture is contacted with uracil-N-DNA glycosylase (UNG). UNG cleaves the uracil from DNA leaving an abasic site. The sample is further contacted with an endonuclease cleaving the DNA at abasic sites. In some embodiments, the endonuclease is $E.\ coli$ endonuclease VIII. Following the endonuclease digestion, the primer binding site no longer supports primer binding and extension.

In the embodiment where dI is incorporated, the reaction mixture is contacted with an endonuclease such as $E.\ coli$ endonuclease V. Following the endonuclease digestion, the primer binding site no longer supports primer binding and extension.

f. UD-PETE for Library Construction and Analysis

Described herein are unidirectional double-primer extension target enrichment (UD-PETE) methods for enriching a plurality of structurally different target polynucleotides from a sample. The enriched target polynucleotides can be a library for downstream analysis (e.g., a high-throughput sequencing library). In some embodiments, the plurality of structurally different target polynucleotides includes target polynucleotides encoding, or encoding at least, 100; 1,000; 5,000; 15,000; 20,000; 30,000; 40,000; 50,000; 100,000; 250,000; 500,000; or 1,000,000 different target sequences. In some cases, at least some proportion of the different target sequences overlap by at least 1 nucleotide but do not overlap by all nucleotides.

The plurality of structurally different target polynucleotides can, e.g., be or include a panel of target polynucleotides that are implicated in, or useful for, diagnosis or monitoring of cancer. As another example, the plurality of structurally different target polynucleotides can, e.g., be or include a panel of target polynucleotides that are implicated in, or useful for, diagnosis or monitoring of an autoimmune disease, such as multiple sclerosis or systemic lupus erythematosus. As yet another example, the plurality of structurally different target polynucleotides can, e.g., be subset, or all, or substantially all (e.g., >90%), immune receptor targets (e.g., B cell receptors (BCRs), T cell receptors (TCRs), γ/δ TCRs, α/β TCRS, TCR β-chains, TCR δ-chains, TCR α-chains, TCR γ-chains, BCR heavy chains, BCR light chains, BCR κ-chains, BCR λ-chains, or a combination or subset of a combination of one or more thereof). In some cases, the plurality of structurally different target polynucleotides can be all or substantially all (e.g., >90%), exomes in a genomic sample. In some cases, the combination of structurally different target polynucleotides encode all or substantially all (e.g., >90%) of the genomic sequence in a sample. In some cases, the combination of structurally different target polynucleotides encode a fraction (e.g., about or at least about 1%, 5%, 10%, 15%, 20%, 25%, 30%, 35%, 40%, or 45%), a substantial fraction (e.g., about or at least about 50%, 75%, or 90%), or substantially all (e.g., at least 95%, 99%, 99.9%, or 99.99%), of the mRNA sequences in the sample.

Generally, the methods involve performing one or more of the foregoing first target-specific primer hybridization and extension reactions in a reaction mixture (e.g., in a single reaction mixture) using a plurality of structurally different first target-specific primers that hybridize to a plurality of structurally different target polynucleotides to thereby generate a plurality of extended first target-specific primers. In some cases, single stranded target or non-target polynucleotides, or both, in a reaction mixture are removed using one or more of the methods described herein. For example, the removing can include single-stranded exonuclease digestion. Additionally or alternatively, the removing can include immobilization of double-stranded products containing an affinity liganded (e.g., biotinylated) first target-specific primer extension product and washing away of non-immobilized polynucleotides. In some cases, the first target-specific primer is immobilized because it is covalently attached to a solid surface (e.g., before or after hybridization to target polynucleotide or before or after extension of the first target specific primer that is hybridized to the target polynucleotide). In such cases, the double-stranded products containing the immobilized first target-specific primer can be washed to remove non-immobilized polynucleotides. Methods and compositions for covalently attaching a target-specific primer to a solid surface are well known in the art and include, but are not limited to, those utilizing N-Hydroxysuccinimide-, epoxy-, or aldehyde-based chemistries. In some cases, the removing also removes un-extended first target-specific primers (e.g., single-stranded exonuclease digestion).

Similarly, the method can further include performing one or more of the foregoing second target-specific primer hybridization and extension reactions (e.g., in a single reaction mixture) using a plurality of structurally different second target-specific primers that hybridize to the plurality of structurally different target polynucleotides to thereby generate a plurality of extended second target-specific primers.

In some embodiments, the method can include trimming 3' overhang regions of the plurality of structurally different hybridized target polynucleotides produced by second target-specific primer extension as described herein (e.g., with a 3' to 5' single stranded DNA exonuclease). Alternatively, the method can include hybridizing the second target-specific primers such that the 3' overhang regions of the plurality of structurally different hybridized target polynucleotides are absent (i.e., the 3' terminal nucleotide of the target polynucleotide is hybridized to the second target-specific primer). In such embodiments, the method can include extending a 3' end of the hybridized target polynucleotide (e.g., a trimmed 3' end), thereby incorporating additional 5' sequence of the second-primer extension product (e.g., a barcode such as a UID barcode) as described herein. In some cases, the extending the 3' end of the hybridized target polynucleotide is performed after attachment (e.g., ligation) of a first or a first and second adapter, thus incorporating an adapter sequence including, but not limited to, a universal primer binding sequence, a barcode (e.g., an MID barcode), or the combination thereof.

In some embodiments, the plurality of structurally different target polynucleotides having one or more incorporated barcodes, one or more universal primer binding sites, or a combination thereof, can be recovered from double-stranded products containing such. Methods for recovering such target polynucleotides are described above. In some cases, the target polynucleotides are recovered by 5' to 3' double-stranded DNA exonuclease digestion of 5' blocked target polynucleotides (e.g., target polynucleotides attached at the 5' end to a 5' blocked universal adapter). In some cases, the target polynucleotides are recovered by immobilization of affinity ligand labeled (e.g., biotinylated) target polynucleotide (e.g., target polynucleotides attached at the 5' end to an affinity ligand labeled universal adapter) or otherwise immobilized target polynucleotide and washing away, melting away, or melting and washing away, of hybridized second target-specific primer extension product. In some cases, the target polynucleotides are recovered by immobilization of affinity ligand labeled (e.g., biotinylated) second target-specific primer extension product (e.g., second target-specific primer extension products attached at the 5' end to an affinity ligand labeled universal adapter) or otherwise immobilized target polynucleotide, washing away, melting away, or melting and washing away, of hybridized target polynucleotide, and recovering single-stranded target polynucleotide in solution. In some cases, the immobilized target polynucleotide is attached at the 5' end to a universal adapter that is covalently attached to a solid surface (e.g., via N-Hydroxysuccinimide-, aldehyde-, or epoxy-based chemistry).

In some embodiments, double-stranded products containing first target-specific primers and/or second target-specific primers that are hybridized to target polynucleotides are recovered. For example, the double-stranded products can be immobilized by immobilization of labeled second target-specific primer extension product that is hybridized to target polynucleotide. In some cases, the labeled second target-specific primer extension product is a second target-specific primer extension product attached at the 5' end to a labeled universal adapter, wherein the label is an affinity ligand (e.g., biotin) or label suitable for covalent attachment to a solid surface. The immobilized double-stranded product can then be washed and eluted. For example, a covalent attachment between the label and solid surface can be cleaved to elute the double-stranded product.

In some embodiments, the method includes attaching (e.g., ligating) a first and second universal adapter (e.g., containing forward and reverse universal primer binding sites respectively) to opposite ends of a plurality of structurally different double-stranded products generated by the second target-specific primer hybridization and extension. In some embodiments, extended second target-specific primers are recovered from the double-stranded products generated by second target-specific primer hybridization and extension as described herein. In such embodiments, the method can further include attaching (e.g., ligating) a first and second universal adapter (e.g., containing forward and reverse universal primer binding sites respectively) to opposite ends of a plurality of structurally different extended and recovered second target-specific primers.

In some embodiments, a first, second, or first and second universal adapter is attached by splint ligation using an adapter that hybridizes to, e.g., a splint region of a second-target specific primer or a tail region generated by a terminal transferase reaction, as described herein. In some embodiments, a first, second, or first and second universal adapter is attached by tagmentation (e.g., transposase mediated adapter attachment), as described herein.

One or more of the foregoing plurality of i) adapter-attached double-stranded products; ii) adapter-attached second target-specific primer extension products; or iii) adapter-attached target polynucleotides can be amplified by universal amplification (e.g., universal PCR). Adapter-attached double-stranded products that can be amplified by universal amplification include those containing second-primer extension products, those containing a target polynucleotide (e.g., trimmed target polynucleotide, barcoded target polynucleotide (e.g., UID barcoded, MID barcoded, or the combination thereof), or trimmed and barcoded target polynucleotide), or those containing a second target-specific primer extension product hybridized to one of the foregoing target polynucleotides.

Adapter-attached second target-specific primer extension products that can be amplified by universal amplification include, but are not limited to, adapter-attached tailed second target-specific primer extension products, adapter-attached recovered second target-specific primer extension products, or adapter-attached tailed and recovered second target-specific primer extension products, as described herein. Adapter-attached target polynucleotides that can be amplified by universal amplification include, but are not limited to, adapter-attached trimmed target polynucleotide, barcoded target polynucleotide (e.g., UID barcoded, MID barcoded, or the combination thereof), or trimmed and barcoded target polynucleotide, as described herein.

Described herein are methods for analyzing target polynucleotide sequences enriched from a sample. Generally, the methods include performing any one or more of the UD-PETE methods described herein to obtain a sample enriched for a target polynucleotide, plurality of structurally different target polynucleotides, extended second target-specific primers, a plurality of structurally different extended second target-specific primers, or amplification products thereof. In some cases, the enriched polynucleotides, extended primers, or amplification products thereof contain a sequencing platform-specific adapter region at one or both ends that is compatible for sequencing with one or more known high-throughput sequencing platforms (e.g., a sequencing platform from Illumina, Complete Genomics, BGI, 454 Life Sciences, Ion Torrent, Pacific Biosciences, Genia, or Oxford Nanopore). In some cases, the sequencing platform-specific adapter region is attached by attaching first, second, or first and second universal adapter(s) as described above. The enriched polynucleotides, extended primers, or amplification products thereof contain a sequencing platform-specific adapter region at one or both ends that is compatible for sequencing with one or more known high-throughput sequencing platforms can then be sequenced using the appropriate platform and protocols.

UD-PETE methods described herein can provide enrichment of target polynucleotides, copies thereof (e.g., second target-specific primer extension products), or amplification products thereof from a sample, such that high-throughput sequencing of the enriched sample provides a high number of on-target reads (e.g., a high number of on-target reads in comparison to single-primer PETE, hybrid capture, or multiplex PCR, or a combination thereof). As used herein, "on-target reads" refers to sequence reads of polynucleotides that contain a region that is substantially the same as, or complementary to, the 3' hybridizing region of the second target-specific primers used in the second target-specific primer extension reaction.

In some cases, "on-target reads" additionally or alternatively refers to sequence reads of polynucleotides that contain a region that is substantially the same as, or complementary to, the 3' hybridizing region of the first target-specific primers used in the reaction. Typically, the region is the same as or complementary to a sequence of a polynucleotide that is expected to hybridize to the first, second, or first and second target-specific primer(s) under typical hybridization conditions (e.g., target-specific primer hybridization conditions) used in PETE applications. Such hybridization conditions can include, but are not limited to, hybridization in isothermal amplification buffer (20 mM Tris-HCl, 10 mM $(NH_4)_2SO_4$, 50 mM KCl, 2 mM $MgSO_4$, 0.1% TWEEN® 20, pH 8.8 at 25° C.) at a temperature of about 40° C., 45° C., 50° C., 55° C., 60° C., 65° C., or 70° C.

In some cases, the on-target reads produced by high-throughput sequencing of a sample generated by one or more of the methods described herein can be at least, or at least about, 5%, 10%, 15%, 20%, 25%, 30%, 35%, 40%, 45%, 50%, 55%, 60%, 65%, 70%, 75%, 80%, 85%, 90%, or higher.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

EXAMPLES

Example 1. Removal of the Second Primer Extension Product from the Original Strand In this example, the steps of hybridizing and extending a first target-specific primer to form a first double-stranded product, removing single-stranded target and non-target polynucleotides that are not hybridized to extended target-specific primer, hybridizing and extending a second target-specific primer to form a second double-stranded product comprising a barcode are performed as described generally herein, except that the second primer extension product has been synthesized in the presence of deoxyuracil and a mixture of UNG and endonuclease VIII is used to remove it as described below.

20 μL of the primer extension reaction was mixed with the buffer and the two-enzyme mixture (USER®, New England BioLabs, Mass.) as recommended by the manufacturer and incubated for 10 min at 37 deg. The undegraded DNA (the original strand) was separated from the products of degradation and the reaction mixture using KapaPure SPRI beads (KAPA). The purified DNA was analyzed by qPCR.

Figure 4:
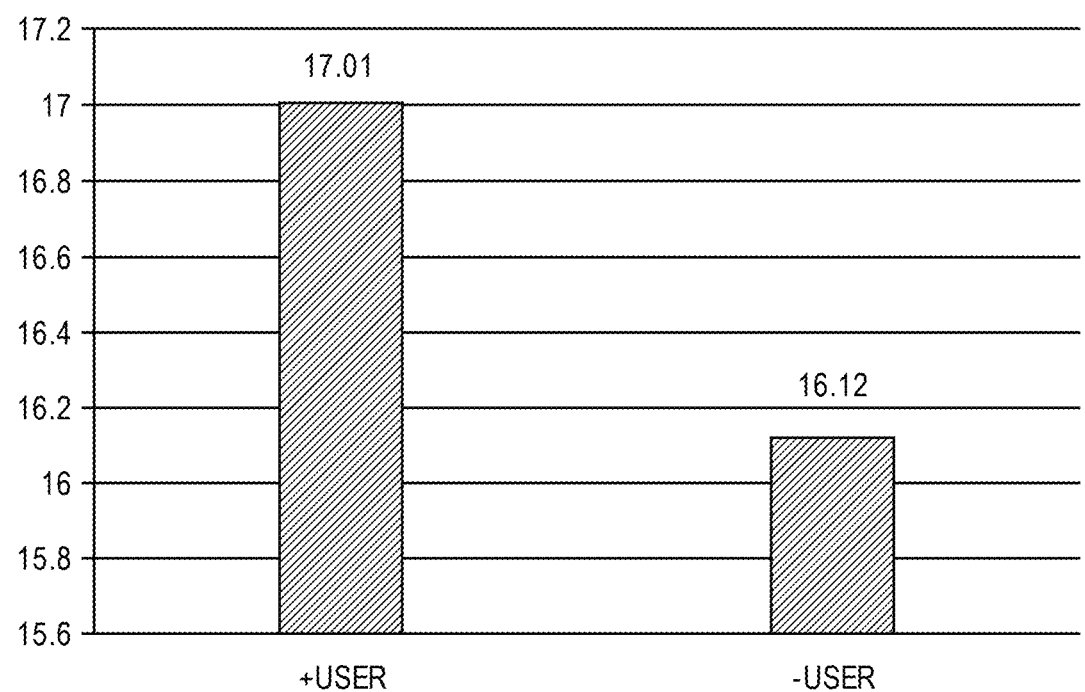
FIG. 4 illustrates the results of incorporating cleavable nucleotides according to the method of the invention.

FIG. 4 shows PCR Ct (Cq) values from the amplification reaction performed with and without the removal of the second strand. With the digestion, the total amount of amplifiable strands of DNA is reduced by half (only 1 strand of the 2 in duplex DNA has a uracil incorporated). As expected, the data shows this 50% reduction as a 1 cycle increase in Ct of the PCR.

Example 2

Libraries were prepared from 50 ng Promega Male human genomic DNA, sheared using Covaris E220, and a mix of 117 target specific primers. These libraries were sequenced to determine the success of enrichment of the target regions during the library preparation.

Library preparation commenced with the shearing of high quality DNA using Covaris physical shearing through sonication as shown below.

To physically shear human genomic DNA, a Covaris E220 system was used. The water bath on the instrument is filled to water level 6 and allowed to degas and cool to 7 C. Once complete a maximum of 5 μg and 130 μL of genomic DNA (promega male, Catalog #G152A) in 10 mM Tris—1 mM EDTA, pH 8.0 is loaded into microTUBE AFA Fiber Snap-Cap (PN 520045). The samples are then placed into a Rack 96 Place microTUBE Crimp-Cap (PN 500282). The rack is set to the home position and shearing begins per sizing guidelines provided by Covaris. An Intensifier (PN 500141) was used but Y-dithering was not, per Covaris guidelines. For mean target peak sizing of 300 bp, the following parameters were set: Peak Incident Power (W) is set to 140, Duty Factor is set to 10%, Cycles per Burst is set to 200, and Treatment Time is set to 80 s. Once complete, remove samples from the Covaris E220 and transfer sheared DNA into microcentrifuge tubes.

The fragmented DNA was run on an AGILENT Bioanalyzer to assess shearing success.

Sheared DNA was then used as the input DNA into the Primer 1 Hybridization and Extension Reaction outlined in Table 2.

TABLE 2

| Component | uL into Reactions | Final Concentration |
| --- | --- | --- |
| DNA | Total 50 ng | 1 ng/uL |
| KAPA 2G Multiplex Mastermix | 10 | 1x |
| 117 Target Specific Biotinylated Primers | 1.5 | 300 nM total, 2.56 nM each |
| dATP | 1.9 | 3.8 mM |
| MgCl2 | 5 | 5 mM |
| Water | Up to 50 uL | n/a |

Samples were then incubated as outlined in Table 3.

TABLE 3

| Step | ° C. | Time | Ramp Rate |
| --- | --- | --- | --- |
| Denaturation | 95 | 5 min | Standard to 80° C. |
|  | 80 | 1 second | 0.1-0.3° C./second to 60° C. |
| Hybridization | 60 | 10 min | Standard to 65° C. |
| Extension | 65 | 2 min | Standard to 4° C. |
|  | 4 | HOLD |  |

Following hybridization and extension with biotinylated primers, samples were mixed at a 1:1 ratio with Dynabeads™ MyOne™ Streptavidin T1 beads. These beads were prepared prior to addition to DNA samples by washing four times with 1× Binding and Wash (B&W) buffer, and resuspending in 2×B&W buffer. The composition of the B&W buffer is described in Table 4.

TABLE 4

| Component | Final in 2x Buffer | Final in 1x Buffer |
|---|---|---|
| Tris-HCl (pH 7.5) | 40 mM | 20 mM |
| EDTA | 2 mM | 1 mM |
| NaCl | 2M | 1M |
| Tween | 0.1% | 0.05% |
| Water | — | — |

Samples were incubated with 50 uL MyOne™ beads for 10 minutes at room temperature on a rotor. Once biotinylated DNA had bound to beads, samples were placed on a magnet for 3 minutes and the supernatant was then removed and discarded. Beads were washed with the 1×B&W buffer described in Table 4 four times to remove non-biotinylated DNA. The samples were then washed with 10 mM Tris pH 7.5 to remove excess salts and were then resuspended in 20 uL of 10 mM Tris, pH 7.5.

The resuspended beads were then taken into the Ligation Reaction for ligation of the adaptor sequences to the 3'end of DNA extended in the Primer 1 Hybridization and Extension Reaction. The composition of the Ligation Reaction is described in Table 5.

TABLE 5

| Component | uL into Reactions | Final Concentration |
|---|---|---|
| DNA + Beads | 20 | |
| TA Adaptor | 1 | 20 mM |
| KAPA Ligation Buffer* | 10 | 1x |
| KAPA Ligation Enzyme* | 5 | 1x |
| Water | Up to 50 uL | n/a |

*From the KAPA LTP Library Preparation Kit

Ligation Reactions were incubated at 20° C. for 30 minutes.

Following ligation samples were placed on a magnet at room temperature for 1-3 minutes, the supernatant was removed, and samples were washed twice with the 1×B&W buffer described in Table 4.

The samples were then washed with 10 mM Tris pH 8.0 to remove excess salts and were then resuspended in 20 uL of 10 mM Tris, pH 7.5.

These samples were then taken into the Primer 2 Hybridization Reaction outlined in Table 6. During this reaction, target specific primers with outnested portions, equivalent to the sequencing adaptor, are hybridized upstream of the primers added in Primer 1 Hybridization and Extension.

TABLE 6

| Component | uL into Reactions | Final Concentration |
|---|---|---|
| DNA + Beads | 20 | |
| KAPA2G Buffer A | 10 | 1x |
| 117 Outnested Target Specific Primers | 1.5 | 300 nM total, 2.56 nM each |
| Water | Up to 50 uL | n/a |

Primer 2 Hybridization Reactions were incubated at 50° C. Samples were then washed as described for the Ligation reactions. Samples were resuspended in 20 uL 10 mM Tris, pH 7.5.

The resuspended beads were then taken into the Extension 2 Reaction. This reaction enabled the extension of Primer 2 and resulted in the release of target DNA molecules into solution. The composition of the Extension 2 reaction is described in Table 7.

TABLE 7

| Component | uL into Reactions | Final Concentration |
|---|---|---|
| DNA + Beads | 20 | |
| KAPA2G Buffer A | 10 | 1x |
| dNTPs | 1 | 0.2 mM each |
| KAPA2G Fast DNA Polymerase | 1 | 5 U |
| Water | Up to 50 uL | n/a |

Extension 2 Reaction samples were incubated at 50° C. for 2 minutes and were then placed directly onto a magnet on ice for 1-3 minutes.

The supernatant (45 uL) was then removed without disturbing the beads, and added to an equal volume (45 uL) of SPRI® beads. A 1×clean-up was performed and samples were eluted in 25 uL 10 mM Tris, pH 7.5.

A qPCR reaction was performed to determine the number of cycles (Ct+5) required to amplify the captured molecules for sequencing. Samples crossed threshold after 24 cycles.

TABLE 8

| Component | uL into Reactions | Final Concentration |
|---|---|---|
| DNA | 2 | |
| KAPA HiFi SybrFast Mix Optimixed for Roche LC480 HotStart ReadyMix | 5 | 1x |
| P1 Primer | 1.5 | 750 nM |
| Indexed Adaptor Primer | 1.5 | 750 nM |
| Water | Up to 50 uL | n/a |

The last step of the library preparation was the Amplification Reaction. This reaction increased the concentration of the samples, completed the sequencing adaptor sequences and added sample indexes. The amplification reaction and cycling parameters are outlined in Tables 9 and 10.

TABLE 9

| Component | uL into Reactions | Final Concentration |
|---|---|---|
| DNA | 20 | |
| KAPA HiFi HotStart ReadyMix | 25 | 1× |
| P1 Primer | 1.25 | 250 nM |
| Indexed Adaptor Primer | 1.25 | 250 nM |
| Water | Up to 50 uL | n/a |

TABLE 10

| Step | ° C. | Time | Cycles |
|---|---|---|---|
| Initial Denaturation | 98 | 1 min | n/a |
| Denaturation | 98 | 15 sec | 26 (10 ng) or 28 (50 ng) |
| Hybridization | 60 | 30 sec | |
| Extension | 72 | 30 sec | |
| Final Extension | 72 | 1 min | n/a |
| | 4 | HOLD | n/a |

A 1×SPRI® clean-up of the PCR product was then performed and the library was eluted in 25 uL 10 mM Tris, pH 7.5.

Libraries were sequenced on the Illumina MiSeq system using v3 chemistries. Libraries were prepared using standard guidelines for denaturation and dilution.

Figure 7A:
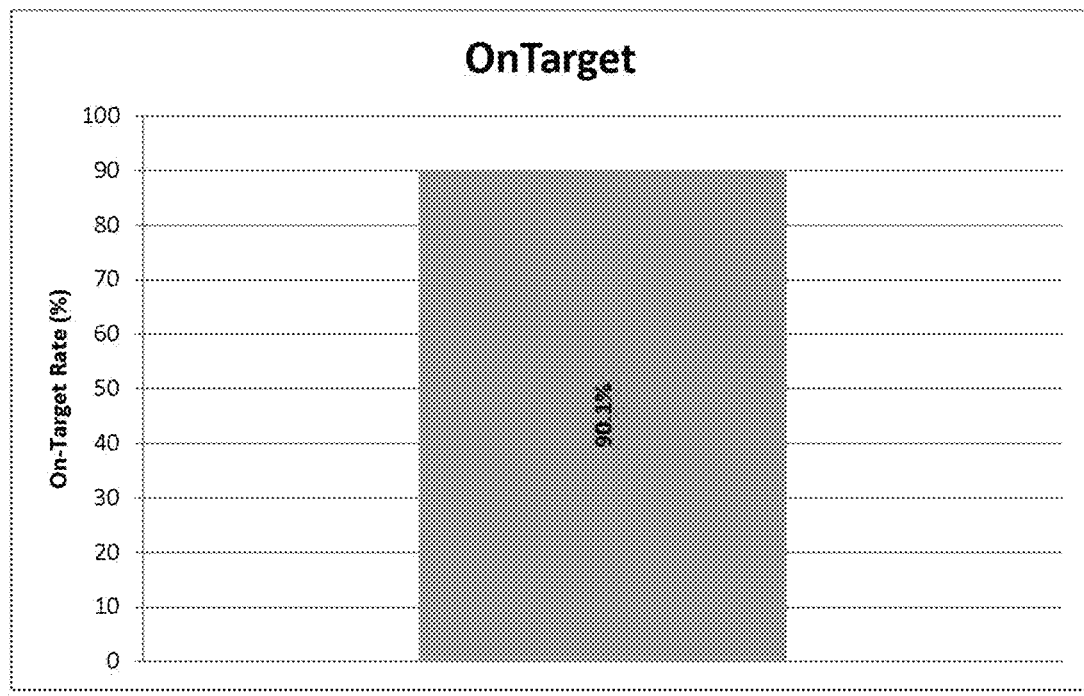
FIGS. 7A-B depict On-Target Rate and Coverage Uniformity as described in Example 2.
Figure 7B:
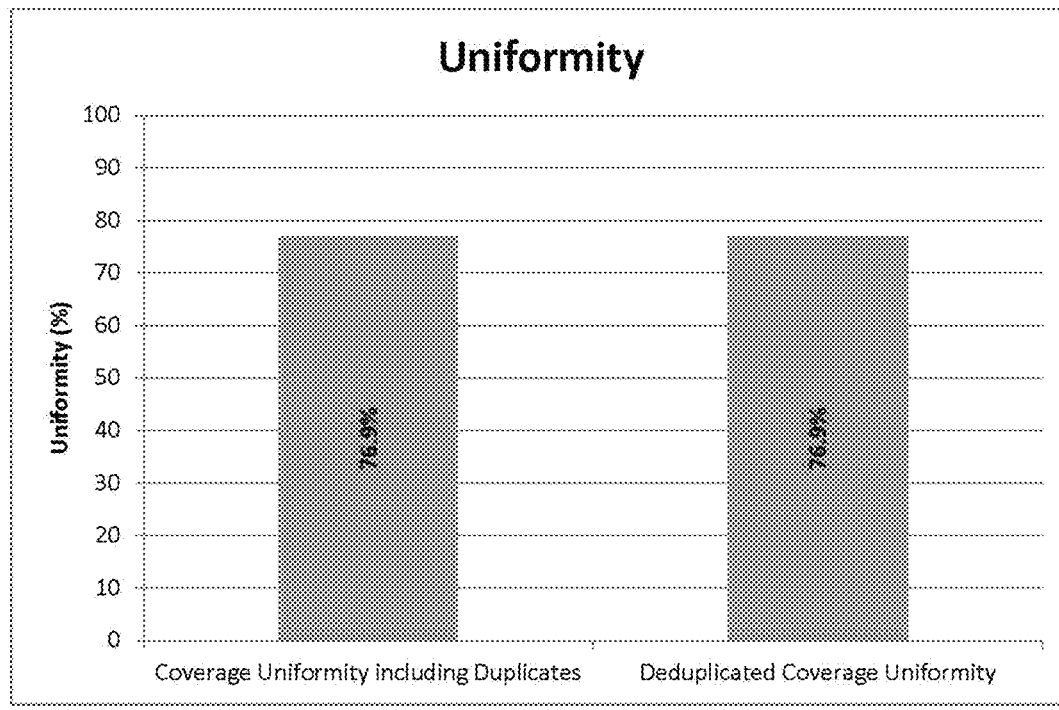

The sequencing results for 50 ng of Covaris sheared DNA included are On-Target Rate and Coverage Uniformity. See, FIG. 7A-B. On-Target rate was calculated as the percent of reads with primers were found mapping to the correct location and a number of bases downstream of the primer matching an expected sequence. Coverage uniformity is calculated as a percent of the total probes that fell within a 0.5× and 2× range of the mean coverage uniformity.

The following oligos were used to during the preparation of libraries:

```
For the
Ligation

20170324P5_TA    AATGATACGGCGACCACCGAGATCTACACTAGATCGCTCGTCGGCAGCG
[N/S/E]501       TCAGATGTGTATAAGAGACAGT (SEQ ID NO: 1)
20170324P5_C     /5Phos/CTGTCTCTTATACACATCTGACGCTGCCGACGA (SEQ ID
TA33             NO: 2)

For qPCR

C5 Universal     AATGATACGGCGACCACCGA (SEQ ID NO: 3)
Primer
20170324P7_      CAAGCAGAAGACGGCATACGAGAT[index]GTCTCGTGGGCTCGGAGA
N70X             TGTGTATAAGAGACAG (SEQ ID NO: 4)

For Final
Amplification

20170324P7_      CAAGCAGAAGACGGCATACGAGAT[index]GTCTCGTGGGCTCGGAGA
N70X             TGTGTATAAGAGACAG (SEQ ID NO: 5)
C5 Universal     AATGATACGGCGACCACCGA (SEQ ID NO: 6)
Primer
```

```
sequence
                                            (SEQ ID NO: 7)
/5Biosg/TGAAAGCTGTACCATACCTGT (SEQ ID NO: 8)
/5Biosg/AGGTTAATATCCGCAAATGACTTG (SEQ ID NO: 9)
/5Biosg/AGATGATCCGACAAGTGAGAG (SEQ ID NO: 10)
/5Biosg/TACGTCTCCTCCGACCAC (SEQ ID NO: 11)
/5Biosg/CGCAGCCTGTACCCAGTG (SEQ ID NO: 12)
/5Biosg/GCGGAAGATGAAGATTTCGGAT (SEQ ID NO: 13)
/5Biosg/GTTAGCTCATTTTTGTTAATGGTGG (SEQ ID NO: 14)
/5Biosg/TTAAACTTTTCTTTTAGTTGTGCTGA (SEQ ID NO: 15)
/5Biosg/GTATGCAACATTTCTAAAGTTACCTAC (SEQ ID NO: 16)
/5Biosg/AAGACCATAACCCACCACAG (SEQ ID NO: 17)
/5Biosg/CTGGAAAGGGACGAACTGGT (SEQ ID NO: 18)
/5Biosg/CGACCCAGTTACCATAGCAA (SEQ ID NO: 19)
/5Biosg/AGAAAATGGAAGTCTATGTGATCAAG (SEQ ID NO: 20)
/5Biosg/CATTTTAAATTTTCTTTCTCTAGGTGAAG (SEQ ID NO: 21)
/5Biosg/GGTCTTGGCCGAGGTCTC (SEQ ID NO: 22)
/5Biosg/CAGCACCATGGGCACGTC (SEQ ID NO: 23)
/5Biosg/GAGAGGTGGAAAGCGAGAG (SEQ ID NO: 24)
/5Biosg/CACTCTTGCCCACACCGC (SEQ ID NO: 25)
/5Biosg/CTGTATTTATTTCAGTGTTACTTACCTG (SEQ ID NO: 26)
/5Biosg/TTATATTCAATTTAAACCCACCTATAATGG (SEQ ID NO: 27)
/5Biosg/GTATCAAAGAATGGTCCTGCAC (SEQ ID NO: 28)
/5Biosg/ACACAACACAAAATAGCCGTATA (SEQ ID NO: 29)
/5Biosg/TCTATTCTTTCCTTTGTAGTGTCCA (SEQ ID NO: 30)
/5Biosg/TGATTTCTGTTTTTACCTCCTAAAGAA (SEQ ID NO: 31)
/5Biosg/ATCTTTAAAGAGAAATTTGCTAAAGCTGTG (SEQ ID NO: 32)
/5Biosg/ACGTGTTTTGATCAAAGAAGAGG (SEQ ID NO: 33)
/5Biosg/AGCCTCACGTTGGTCCAC (SEQ ID NO: 34)
/5Biosg/GGATGGCTAGGCGAGGAG
```

-continued

/5Biosg/AGGGACTAGGCGTGGGAT (SEQ ID NO: 35)

/5Biosg/CCAAGCCCTAGGGTGGTG (SEQ ID NO: 36)

/5Biosg/ACGCTCTTCTCACTCATATCC (SEQ ID NO: 37)

/5Biosg/AAGAAATCTTAGACGTAAGCCCCTC (SEQ ID NO: 38)

/5Biosg/TCCCATACCCTCTCAGCG (SEQ ID NO: 39)

/5Biosg/GGATGAGCTACCTGGAGGAT (SEQ ID NO: 40)

/5Biosg/ATTTTGAGTGTTAGACTGGAAACT (SEQ ID NO: 41)

/5Biosg/GGGCAGTGCTAGGAAAGAG (SEQ ID NO: 42)

/5Biosg/TGCTTACCTCGCTTAGTGC (SEQ ID NO: 43)

/5Biosg/GCCGGGGATGTGATGAGA (SEQ ID NO: 44)

/5Biosg/CAGGGGTCAGAGGCAAGC (SEQ ID NO: 45)

/5Biosg/AGGGCCACTGACAACCAC (SEQ ID NO: 46)

/5Biosg/TGTTTCTGTCATCCAAATACTCC (SEQ ID NO: 47)

/5Biosg/AGTGAGGAATCAGAGGCCT (SEQ ID NO: 48)

/5Biosg/GTGCTGTGACTGCTTGTAGA (SEQ ID NO: 49)

/5Biosg/ACGGCCAGGCATTGAAGT (SEQ ID NO: 50)

/5Biosg/AAACCGTAGCTGCCCTGG (SEQ ID NO: 51)

/5Biosg/TCAAAATTGCTTCAGAAATTGGAG (SEQ ID NO: 52)

/5Biosg/ACAAGGTGGAGAGAGTGAAAC (SEQ ID NO: 53)

/5Biosg/GCCATCGTTGTCCACTGAA (SEQ ID NO: 54)

/5Biosg/TGGTGTTCCATTGCTTACTTTG (SEQ ID NO: 55)

/5Biosg/GCAGAGAAGTTATATGCTGAGGAG (SEQ ID NO: 56)

/5Biosg/CTGCTGCTGGAATTGGTGT (SEQ ID NO: 57)

/5Biosg/TCAAAGAAACACCTTGCTGGA (SEQ ID NO: 58)

/5Biosg/CACCGCATCGACTCCACC (SEQ ID NO: 59)

/5Biosg/CAGCTGGTTCCGGAAGAAA (SEQ ID NO: 60)

/5Biosg/TGCAGATTGGGCCTTGGG (SEQ ID NO: 61)

-continued

/5Biosg/TGGAAATTTCTGGGCCATGA (SEQ ID NO: 62)

/5Biosg/ACAGAGAAATGTTGTACAGATTGAG (SEQ ID NO: 63)

/5Biosg/TCAATAGTGCAGATGGGAGG (SEQ ID NO: 64)

/5Biosg/GCGGGTCTCTCGGAGGAA (SEQ ID NO: 65)

/5Biosg/AGAAGCAAGAAAATACCCCT (SEQ ID NO: 66)

/5Biosg/CGACTTTGTGACCTTCGGC (SEQ ID NO: 67)

/5Biosg/CCAATGGACTGTTTTACAATGCC (SEQ ID NO: 68)

/5Biosg/TTATTTTATTTTACAGAGTAACAGACTAGC (SEQ ID NO: 69)

/5Biosg/CCAAACTGACCAAACTGTTCTTATTAC (SEQ ID NO: 70)

/5Biosg/TGATGCTTGGCTCTGGAAT (SEQ ID NO: 71)

/5Biosg/CGAAAGACCCTAGCCTTAGAT (SEQ ID NO: 72)

/5Biosg/GTTTCGTATTTATAGCTGATTTGATGG (SEQ ID NO: 73)

/5Biosg/CCTTATGATTCATCAGGAGAGCATTTAA (SEQ ID NO: 74)

/5Biosg/TCTGGATCCCACACCTTTAC (SEQ ID NO: 75)

/5Biosg/GCTATGGCTTTCCTAGAATAGAAAC (SEQ ID NO: 76)

/5Biosg/TTTTTCATGAAGATGCATACAACG (SEQ ID NO: 77)

/5Biosg/GAAGAATGTAATTGATAATCTTTACCTCTT (SEQ ID NO: 78)

/5Biosg/GCTGCTCGCAACGTCCTC (SEQ ID NO: 79)

/5Biosg/CGTTTGGAAAGCTAGTGGTTC (SEQ ID NO: 80)

/5Biosg/TCTCCAGAGTGCTCTAATGAC (SEQ ID NO: 81)

/5Biosg/CCATCACCACTTACCTTGTTG (SEQ ID NO: 82)

/5Biosg/CAGAGACTTGGCAGCCAG (SEQ ID NO: 83)

/5Biosg/AGAAATATCCTCCTTACTCATGGT (SEQ ID NO: 84)

/5Biosg/GCTTTTACTGATTAACGTAAATACAAGAT (SEQ ID NO: 85)

/5Biosg/CTTTTAAGTGGTAGCCATAGTATGat (SEQ ID NO: 86)

/5Biosg/TTCAGCAAATCGAAAGGACAT (SEQ ID NO: 87)

/5Biosg/AATTGTTTATCATACAGACACTTCATTT (SEQ ID NO: 88)

-continued

/5Biosg/TCAACTACACGAATGGACCA (SEQ ID NO: 89)

/5Biosg/TGAGGAATTTGTCTTGGCGAG (SEQ ID NO: 90)

/5Biosg/CCAAGGCATCTCATCGTAGTA (SEQ ID NO: 91)

/5Biosg/GTCAGACAATTTTAATACTGGCAAC (SEQ ID NO: 92)

/5Biosg/GTTCTGAAAAGATAGAAGTTTGGAG (SEQ ID NO: 93)

/5Biosg/TTGCAGATCTCCACCACTG (SEQ ID NO: 94)

/5Biosg/GGTCTACCACTGAATTACATTGTG (SEQ ID NO: 95)

/5Biosg/CGGAAAATTCAAATAGGACATGTTCTATG (SEQ ID NO: 96)

/5Biosg/GAATGAAAGATGGGCAAGACC (SEQ ID NO: 97)

/5Biosg/CACATTTTGGACAGCAGGAAT (SEQ ID NO: 98)

/5Biosg/AGGCAGAATCAGCTCCATCC (SEQ ID NO: 99)

/5Biosg/GACTTATTGTGTAGAAGATACTCCAATA (SEQ ID NO: 100)

/5Biosg/TCAGACGACACAGGAAGC (SEQ ID NO: 101)

/5Biosg/AGCACCCTAGAACCAAATCC (SEQ ID NO: 102)

/5Biosg/CGAAATCTCCCTCCAAAAGTG (SEQ ID NO: 103)

/5Biosg/TGAGAGTCGTTCGATTGCCA (SEQ ID NO: 104)

/5Biosg/GACAAACCATGCCACCAAG (SEQ ID NO: 105)

/5Biosg/TGAAAAGAGAGAGTGGACC (SEQ ID NO: 106)

/5Biosg/ACGGAAAGTACTCCAGATGG (SEQ ID NO: 107)

/5Biosg/GTTCAGGAAAATGACAATGGGA (SEQ ID NO: 108)

/5Biosg/GTCCTTTCTGTAGGCTGGAT (SEQ ID NO: 109)

/5Biosg/CACAAAATGGATCCAGACAACT (SEQ ID NO: 110)

/5Biosg/AGTTGTTAAACATATCCTATTATGACTTG (SEQ ID NO: 111)

/5Biosg/GTGAGGGCTGAGGTGACC (SEQ ID NO: 112)

/5Biosg/GCCAGTTAACGTCTTCCTTCT (SEQ ID NO: 113)

/5Biosg/TTCTGGCCACCATGCGAA (SEQ ID NO: 114)

/5Biosg/CTCACAGCAGGGTCTTCTC (SEQ ID NO: 115)

/5Biosg/TCAAGATCACAGATTTTGGGC (SEQ ID NO: 116)

/5Biosg/CACGTGTTGAAGTCCTCGT (SEQ ID NO: 117)

/5Biosg/CTCCCGGGCTGAACTTTC (SEQ ID NO: 118)

/5Biosg/TGCGGGCATGGTTACTGC (SEQ ID NO: 119)

/5Biosg/CGATGGCCCAGCTCCTCA (SEQ ID NO: 120)

/5Biosg/CACGGGTCGGGTGAGAGT (SEQ ID NO: 121)

/5Biosg/TTTTTTCCTTAGTCTTTCTTTGAAGC (SEQ ID NO: 122)

/5Biosg/TCATATTCACTAAGCGCTACTAGA (SEQ ID NO: 123)

sequence

GTCTCGTGGGCTCGGAGATGTGTATAAGAGACAGWNNNNNNWGTTAATCAACTGATGCAAACTCTTG (SEQ ID NO: 124)

GTCTCGTGGGCTCGGAGATGTGTATAAGAGACAGWNNNNNNWAAATAATGCTCCTAGTACCTGTAGA (SEQ ID NO: 125)

GTCTCGTGGGCTCGGAGATGTGTATAAGAGACAGWNNNNNNWTCCTTTAATACAGAATATGGGTAAAGAT (SEQ ID NO: 126)

GTCTCGTGGGCTCGGAGATGTGTATAAGAGACAGWNNNNNNWTGTAAACCTTGCAGACAAACTC (SEQ ID NO: 127)

GTCTCGTGGGCTCGGAGATGTGTATAAGAGACAGWNNNNNNWCCATGAGGCAGAGCATACG (SEQ ID NO: 128)

GTCTCGTGGGCTCGGAGATGTGTATAAGAGACAGWNNNNNNWACATCCTGGTAGCTGAGGG (SEQ ID NO: 129)

GTCTCGTGGGCTCGGAGATGTGTATAAGAGACAGWNNNNNNWGTCTTTTGGTTTTTCTTGATAGTATTAATG (SEQ ID NO: 130)

GTCTCGTGGGCTCGGAGATGTGTATAAGAGACAGWNNNNNNWTTCTTCCTAAGTGCAAAAGATAACT (SEQ ID NO: 131)

GTCTCGTGGGCTCGGAGATGTGTATAAGAGACAGWNNNNNNWCAGTGTTTCTTTTAAATACCTGTTAAGTTT (SEQ ID NO: 132)

GTCTCGTGGGCTCGGAGATGTGTATAAGAGACAGWNNNNNNWCCACAGTTGCACAATATCCTTT (SEQ ID NO: 133)

-continued (SEQ ID NO: 134)
GTCTCGTGGGCTCGGAGATGTGTATAAGAGACAGWNNNNNNWTGCAGCAA
TTCACTGTAAAGC (SEQ ID NO: 135)
GTCTCGTGGGCTCGGAGATGTGTATAAGAGACAGWNNNNNNWCTAATGTA
TATATGTTCTTAAATGGCTACG (SEQ ID NO: 136)
GTCTCGTGGGCTCGGAGATGTGTATAAGAGACAGWNNNNNNWCCAGGACC
AGAGGAAACCT (SEQ ID NO: 137)
GTCTCGTGGGCTCGGAGATGTGTATAAGAGACAGWNNNNNNWAAATAGTT
TAAGATGAGTCATATTTGTGG (SEQ ID NO: 138)
GTCTCGTGGGCTCGGAGATGTGTATAAGAGACAGWNNNNNNWCTGTGGGG
TGGAGAGCTG (SEQ ID NO: 139)
GTCTCGTGGGCTCGGAGATGTGTATAAGAGACAGWNNNNNNWGGTCACAC
TTGTTCCCCAC (SEQ ID NO: 140)
GTCTCGTGGGCTCGGAGATGTGTATAAGAGACAGWNNNNNNWCCGTTTGA
TCTGCTCCCT (SEQ ID NO: 141)
GTCTCGTGGGCTCGGAGATGTGTATAAGAGACAGWNNNNNNWCTGGATGG
TCAGCGCACT (SEQ ID NO: 142)
GTCTCGTGGGCTCGGAGATGTGTATAAGAGACAGWNNNNNNWGTTATGAT
TTTGCAGAAAACAGATCT (SEQ ID NO: 143)
GTCTCGTGGGCTCGGAGATGTGTATAAGAGACAGWNNNNNNWACTATAAT
TACTCCTTAATGTCACTTAT (SEQ ID NO: 144)
GTCTCGTGGGCTCGGAGATGTGTATAAGAGACAGWNNNNNNWTGAATGGT
CAGAGAAACCTTTATC (SEQ ID NO: 145)
GTCTCGTGGGCTCGGAGATGTGTATAAGAGACAGWNNNNNNWTGCAGTTG
TTTACCATGATAACG (SEQ ID NO: 146)
GTCTCGTGGGCTCGGAGATGTGTATAAGAGACAGWNNNNNNWCGAAATAA
CACAAATTTTTAAGGTTACTGA (SEQ ID NO: 147)
GTCTCGTGGGCTCGGAGATGTGTATAAGAGACAGWNNNNNNWTGATTACA
CAGTATCCTCGACAT (SEQ ID NO: 148)
GTCTCGTGGGCTCGGAGATGTGTATAAGAGACAGWNNNNNNWCTGAAAAG
AGTGAAGGATATAGGATAC (SEQ ID NO: 149)
GTCTCGTGGGCTCGGAGATGTGTATAAGAGACAGWNNNNNNWACTGTTCT
TCCTCAGACATTCA (SEQ ID NO: 150)
GTCTCGTGGGCTCGGAGATGTGTATAAGAGACAGWNNNNNNWCCACAGAG
AAGTTGTTGAGGG (SEQ ID NO: 151)
GTCTCGTGGGCTCGGAGATGTGTATAAGAGACAGWNNNNNNWGCCTTGTA
CTGCAGAGACAA (SEQ ID NO: 152)
GTCTCGTGGGCTCGGAGATGTGTATAAGAGACAGWNNNNNNWTACGGGCT
TGGTCC (SEQ ID NO: 153)
GTCTCGTGGGCTCGGAGATGTGTATAAGAGACAGWNNNNNNWTACAGCGG
AGAAGGGAGCG (SEQ ID NO: 154)
GTCTCGTGGGCTCGGAGATGTGTATAAGAGACAGWNNNNNNWCAGGTAGG
ATCCAGCCCA (SEQ ID NO: 155)
GTCTCGTGGGCTCGGAGATGTGTATAAGAGACAGWNNNNNNWATCCCCCA
AAGCCAACAA (SEQ ID NO: 156)
GTCTCGTGGGCTCGGAGATGTGTATAAGAGACAGWNNNNNNWGTTTGGGG
GTGTGTGGTC (SEQ ID NO: 157)
GTCTCGTGGGCTCGGAGATGTGTATAAGAGACAGWNNNNNNWGGTGCTTC
CCATTCCAGG (SEQ ID NO: 158)
GTCTCGTGGGCTCGGAGATGTGTATAAGAGACAGWNNNNNNWACAGTCAA
GAAGAAAACGGC (SEQ ID NO: 159)
GTCTCGTGGGCTCGGAGATGTGTATAAGAGACAGWNNNNNNWAGAGGAGC
TGGTGTTGTTG (SEQ ID NO: 160)
GTCTCGTGGGCTCGGAGATGTGTATAAGAGACAGWNNNNNNWACCGCTTC
TTGTCCTGCT (SEQ ID NO: 161)
GTCTCGTGGGCTCGGAGATGTGTATAAGAGACAGWNNNNNNWGAGCAGTA
AGGAGATTCCCC (SEQ ID NO: 162)
GTCTCGTGGGCTCGGAGATGTGTATAAGAGACAGWNNNNNNWAAATCGGT
AAGAGGTGGGC (SEQ ID NO: 163)
GTCTCGTGGGCTCGGAGATGTGTATAAGAGACAGWNNNNNNWCCCCCTAC
TGCCACCTG (SEQ ID NO: 164)
GTCTCGTGGGCTCGGAGATGTGTATAAGAGACAGWNNNNNNWCCACCACA
CTATGTCGAAG (SEQ ID NO: 165)
GTCTCGTGGGCTCGGAGATGTGTATAAGAGACAGWNNNNNNWGGCCAGAC
CTAAGAGCAATC

```
                                        (SEQ ID NO: 166)
GTCTCGTGGGCTCGGAGATGTGTATAAGAGACAGWNNNNNNWGCCTCACA

ACCTCCCAT (SEQ ID NO: 167)
GTCTCGTGGGCTCGGAGATGTGTATAAGAGACAGWNNNNNNWACAAAAGA

AATGCAGGGGAT (SEQ ID NO: 168)
GTCTCGTGGGCTCGGAGATGTGTATAAGAGACAGWNNNNNNWGCAAGAAG

CCCAGACGGA (SEQ ID NO: 169)
GTCTCGTGGGCTCGGAGATGTGTATAAGAGACAGWNNNNNNWTTTCACTG

TTTCCAAAGGATCAA (SEQ ID NO: 170)
GTCTCGTGGGCTCGGAGATGTGTATAAGAGACAGWNNNNNNWTGCATAGT

TTGATGTGCCATAG (SEQ ID NO: 171)
GTCTCGTGGGCTCGGAGATGTGTATAAGAGACAGWNNNNNNWTGCATGAC

TTTGAGGGACAG (SEQ ID NO: 172)
GTCTCGTGGGCTCGGAGATGTGTATAAGAGACAGWNNNNNNWCATTTATT

TCCTATAGCTCCTGAGTAT (SEQ ID NO: 173)
GTCTCGTGGGCTCGGAGATGTGTATAAGAGACAGWNNNNNNWTGTTACTT

CTTGGCACTTTAGC (SEQ ID NO: 174)
GTCTCGTGGGCTCGGAGATGTGTATAAGAGACAGWNNNNNNWCTTTTCTG

TTAGGTCTGTCAC (SEQ ID NO: 175)
GTCTCGTGGGCTCGGAGATGTGTATAAGAGACAGWNNNNNNWGGATTACC

CAAGACAGAGCA (SEQ ID NO: 176)
GTCTCGTGGGCTCGGAGATGTGTATAAGAGACAGWNNNNNNWGGGTATGG

ACACGTTCACC (SEQ ID NO: 177)
GTCTCGTGGGCTCGGAGATGTGTATAAGAGACAGWNNNNNNWACTGCTTC

TGGGCGTTTG (SEQ ID NO: 178)
GTCTCGTGGGCTCGGAGATGTGTATAAGAGACAGWNNNNNNWGAGCCGTC

CTGGGATTGC (SEQ ID NO: 179)
GTCTCGTGGGCTCGGAGATGTGTATAAGAGACAGWNNNNNNWAGATAAGA

ATAAAACACATACAAGTTGG (SEQ ID NO: 180)
GTCTCGTGGGCTCGGAGATGTGTATAAGAGACAGWNNNNNNWTGTTTTTG

AACTGTCGTATTTTTCAAT (SEQ ID NO: 181)
GTCTCGTGGGCTCGGAGATGTGTATAAGAGACAGWNNNNNNWTTGACCAT

GACCATGTAAACG (SEQ ID NO: 182)
GTCTCGTGGGCTCGGAGATGTGTATAAGAGACAGWNNNNNNWTCTCACTC

ACCGGGCGAG (SEQ ID NO: 183)
GTCTCGTGGGCTCGGAGATGTGTATAAGAGACAGWNNNNNNWCTACATTA

ATAACCATAAAGCATGAACTAT (SEQ ID NO: 184)
GTCTCGTGGGCTCGGAGATGTGTATAAGAGACAGWNNNNNNWGGAAGAAT

TTTTTGATGAAACAAGACG (SEQ ID NO: 185)
GTCTCGTGGGCTCGGAGATGTGTATAAGAGACAGWNNNNNNWAAGCCTTT

ATTCTCAACTGCC (SEQ ID NO: 186)
GTCTCGTGGGCTCGGAGATGTGTATAAGAGACAGWNNNNNNWGGGAAAAA

TATGACAAAGAAAGCTATATAA (SEQ ID NO: 187)
GTCTCGTGGGCTCGGAGATGTGTATAAGAGACAGWNNNNNNWCCTGAAGG

TAAACATCATTTGCTC (SEQ ID NO: 188)
GTCTCGTGGGCTCGGAGATGTGTATAAGAGACAGWNNNNNNWCCAATCTC

TTCATAAATCTTTTCTCAATG (SEQ ID NO: 189)
GTCTCGTGGGCTCGGAGATGTGTATAAGAGACAGWNNNNNNWTTTTGATG

ACATTGCATACATTCG (SEQ ID NO: 190)
GTCTCGTGGGCTCGGAGATGTGTATAAGAGACAGWNNNNNNWGTAACATT

TCCAATCTACTAATGCTAATAC (SEQ ID NO: 191)
GTCTCGTGGGCTCGGAGATGTGTATAAGAGACAGWNNNNNNWGACAGTGA

TTATCTGAGTAAACAAC (SEQ ID NO: 192)
GTCTCGTGGGCTCGGAGATGTGTATAAGAGACAGWNNNNNNWCGTGTGTA

GACAGGTTTCAGTC (SEQ ID NO: 193)
GTCTCGTGGGCTCGGAGATGTGTATAAGAGACAGWNNNNNNWCACCAATT

TTAAGACAAAACGCT (SEQ ID NO: 194)
GTCTCGTGGGCTCGGAGATGTGTATAAGAGACAGWNNNNNNWCCATGACA

AGATTTTCCCTTACC (SEQ ID NO: 195)
GTCTCGTGGGCTCGGAGATGTGTATAAGAGACAGWNNNNNNWGTTATATA

TTCAAATAACACCCAATGAAGA (SEQ ID NO: 196)
GTCTCGTGGGCTCGGAGATGTGTATAAGAGACAGWNNNNNNWTGTGTCCA

CCGTGATCTG (SEQ ID NO: 197)
GTCTCGTGGGCTCGGAGATGTGTATAAGAGACAGWNNNNNNWACTAAACT

CATCTGGGCCAC
```

```
                                                      (SEQ ID NO: 198)
GTCTCGTGGGCTCGGAGATGTGTATAAGAGACAGWNNNNNNWACCTACAA

ATATTTACAGGTAACCATTTA (SEQ ID NO: 199)
GTCTCGTGGGCTCGGAGATGTGTATAAGAGACAGWNNNNNNWTTCAATTC

CACCACCAGCA (SEQ ID NO: 200)
GTCTCGTGGGCTCGGAGATGTGTATAAGAGACAGWNNNNNNWTCTCCTCC

AACCTAATAGTGTATTC (SEQ ID NO: 201)
GTCTCGTGGGCTCGGAGATGTGTATAAGAGACAGWNNNNNNWCACAGAGA

CTTGGCAGCC (SEQ ID NO: 202)
GTCTCGTGGGCTCGGAGATGTGTATAAGAGACAGWNNNNNNWTTGGTTCT

TATATGCTTTTTTGCTT (SEQ ID NO: 203)
GTCTCGTGGGCTCGGAGATGTGTATAAGAGACAGWNNNNNNWGAGAATGA

TTTGACATAACCCTGA (SEQ ID NO: 204)
GTCTCGTGGGCTCGGAGATGTGTATAAGAGACAGWNNNNNNWATTTTAGC

GAAGAATAGCCAGAAT (SEQ ID NO: 205)
GTCTCGTGGGCTCGGAGATGTGTATAAGAGACAGWNNNNNNWTGAACAGT

TATAATGGTCAACTTATGA (SEQ ID NO: 206)
GTCTCGTGGGCTCGGAGATGTGTATAAGAGACAGWNNNNNNWCCATCTAT

AATGTGCTTAATTTTTAGGG (SEQ ID NO: 207)
GTCTCGTGGGCTCGGAGATGTGTATAAGAGACAGWNNNNNNWGCAGGTTA

TTGCGAGTGTTT (SEQ ID NO: 208)
GTCTCGTGGGCTCGGAGATGTGTATAAGAGACAGWNNNNNNWTTGACAAT

ATAGACAATTTAAGTCCCA (SEQ ID NO: 209)
GTCTCGTGGGCTCGGAGATGTGTATAAGAGACAGWNNNNNNWCACCAATC

GACATGATGATAATAGG (SEQ ID NO: 210)
GTCTCGTGGGCTCGGAGATGTGTATAAGAGACAGWNNNNNNWAGAGGAAG

CTTAATAGTTCTCG (SEQ ID NO: 211)
GTCTCGTGGGCTCGGAGATGTGTATAAGAGACAGWNNNNNNWGAACTTCT

TCAAAGCGAGGTT (SEQ ID NO: 212)
GTCTCGTGGGCTCGGAGATGTGTATAAGAGACAGWNNNNNNWGCCATTCA

TACCTCTCAGGAAG (SEQ ID NO: 213)
GTCTCGTGGGCTCGGAGATGTGTATAAGAGACAGWNNNNNNWCAAACACT

TACAATTTCACTAAGTCG (SEQ ID NO: 214)
GTCTCGTGGGCTCGGAGATGTGTATAAGAGACAGWNNNNNNWAGGCAAAG

TCCTTCACAGAA (SEQ ID NO: 215)
GTCTCGTGGGCTCGGAGATGTGTATAAGAGACAGWNNNNNNWCACCTCAA

GTTCCAACCACA (SEQ ID NO: 216)
GTCTCGTGGGCTCGGAGATGTGTATAAGAGACAGWNNNNNNWCACACCTT

CATCTAATGCCAAG (SEQ ID NO: 217)
GTCTCGTGGGCTCGGAGATGTGTATAAGAGACAGWNNNNNNWCTTCTATT

AACCAAGAAACAATACAGAC (SEQ ID NO: 218)
GTCTCGTGGGCTCGGAGATGTGTATAAGAGACAGWNNNNNNWCAGCTGAA

ATGAAATAGGATGTAATC (SEQ ID NO: 219)
GTCTCGTGGGCTCGGAGATGTGTATAAGAGACAGWNNNNNNWCGAAGTTC

CAGCAGTGTCAC (SEQ ID NO: 220)
GTCTCGTGGGCTCGGAGATGTGTATAAGAGACAGWNNNNNNWTGTTGAAT

TTTCTTCAGGAGCG (SEQ ID NO: 221)
GTCTCGTGGGCTCGGAGATGTGTATAAGAGACAGWNNNNNNWCTTCTGTC

AGTTCACTTGATAGTT (SEQ ID NO: 222)
GTCTCGTGGGCTCGGAGATGTGTATAAGAGACAGWNNNNNNWGTGATCTT

CCAGATAGCCCTG (SEQ ID NO: 223)
GTCTCGTGGGCTCGGAGATGTGTATAAGAGACAGWNNNNNNWAGTACCTA

AAAATAAAGCACCTACTG (SEQ ID NO: 224)
GTCTCGTGGGCTCGGAGATGTGTATAAGAGACAGWNNNNNNWTGATACTT

TATTACATTTTGCCACG (SEQ ID NO: 225)
GTCTCGTGGGCTCGGAGATGTGTATAAGAGACAGWNNNNNNWAATAAAAG

CCTCCACA (SEQ ID NO: 226)
GTCTCGTGGGCTCGGAGATGTGTATAAGAGACAGWNNNNNNWATTTCAGC

CACGGGTAATAATTT (SEQ ID NO: 227)
GTCTCGTGGGCTCGGAGATGTGTATAAGAGACAGWNNNNNNWGAAAAATA

GCCTCAATTCTTACCATC (SEQ ID NO: 228)
GTCTCGTGGGCTCGGAGATGTGTATAAGAGACAGWNNNNNNWGAACAGTG

AATATTTCCTTTGATGATATT (SEQ ID NO: 229)
GTCTCGTGGGCTCGGAGATGTGTATAAGAGACAGWNNNNNNWGTCTGGCA

CTGCTTTCCA
```

-continued

GTCTCGTGGGCTCGGAGATGTGTATAAGAGACAGWNNNNNNWGTGGCACC (SEQ ID NO: 230)

ATCTCACAATTG

GTCTCGTGGGCTCGGAGATGTGTATAAGAGACAGWNNNNNNWGGTCCATG (SEQ ID NO: 231)

TGCCCCTCCT

GTCTCGTGGGCTCGGAGATGTGTATAAGAGACAGWNNNNNNWTCTTCCCA (SEQ ID NO: 232)

TGATGATCTGTCC

GTCTCGTGGGCTCGGAGATGTGTATAAGAGACAGWNNNNNNWGGTGAAAA (SEQ ID NO: 233)

CACCGCAGCATG

GTCTCGTGGGCTCGGAGATGTGTATAAGAGACAGWNNNNNNWGTTTGTTC (SEQ ID NO: 234)

AGTTGGGAGCG

GTCTCGTGGGCTCGGAGATGTGTATAAGAGACAGWNNNNNNWGCAAGACC (SEQ ID NO: 235)

GGAGACTGGT

GTCTCGTGGGCTCGGAGATGTGTATAAGAGACAGWNNNNNNWGACCTTCC (SEQ ID NO: 236)

GCGGCATCTA

GTCTCGTGGGCTCGGAGATGTGTATAAGAGACAGWNNNNNNWCAGGTACC (SEQ ID NO: 237)

GTGCGACATC

GTCTCGTGGGCTCGGAGATGTGTATAAGAGACAGWNNNNNNWCAGCGTGT (SEQ ID NO: 238)

CCAGGAAGCC

GTCTCGTGGGCTCGGAGATGTGTATAAGAGACAGWNNNNNNWGACAACAG (SEQ ID NO: 239)

TCAAACAACAATTCTTTGTAC

GTCTCGTGGGCTCGGAGATGTGTATAAGAGACAGWNNNNNNWTGACTCCA (SEQ ID NO: 240)

CGAGAACTTGATC

Example 3: 9-Target Panel

Libraries were prepared from 10 and 50 ng Promega Male Human Genomic DNA, sheared using KAPA Frag, and a mix of 9 target specific primers. These libraries were sequenced on the Illumina Miseq to assess the success of enrichment of the target regions during the library preparation.

Figure 8A:
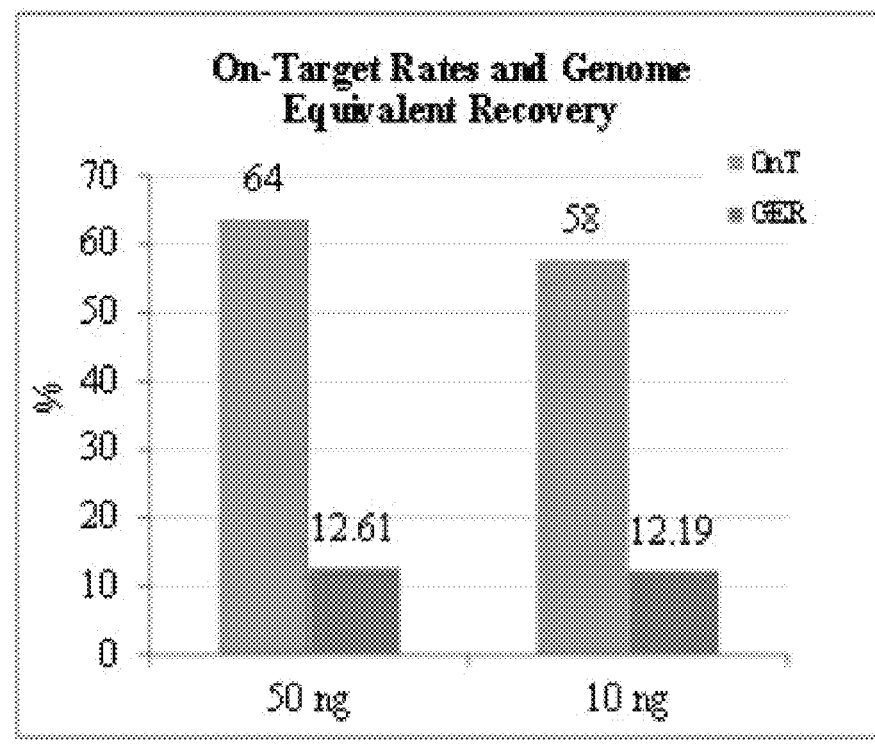
FIGS. 8A-B depict sequencing results from Example 3: on target rate and genome equivalent recovery (GER) (FIG. 8A), and probe coverage uniformity (FIG. 8B).
Figure 8B:
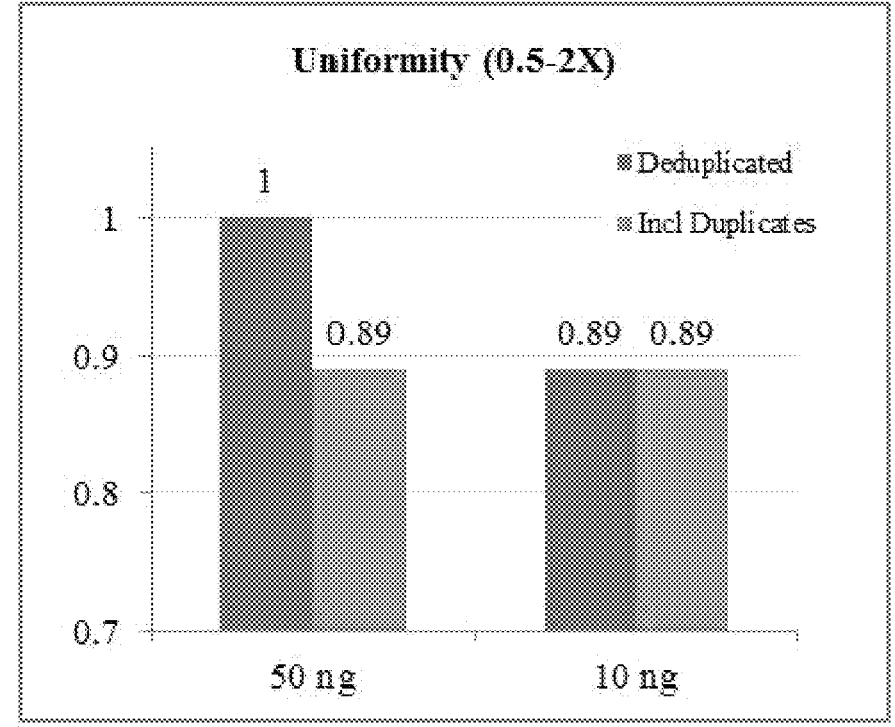

An AGILENT Bioanalyzer trace of the final libraries was prepared. FIG. 8A-B shows the high level sequencing results of the libraries; namely on target rate and genome equivalent recovery (GER) (A), as well as probe coverage uniformity (B). On-Target rate was calculated as the percent of reads with primers were found mapping to the correct location and a number of bases downstream of the primer matching an expected sequence. Coverage uniformity was calculated as a percent of the total probes that fell within a 0.5× and 2× range of the mean coverage uniformity. Libraries prepared with 10 and 50 ng input DNA performed similarly with regards to on-target rate (58-64%), GER (~12%) and uniformity (0.89-1).

Library preparation commenced with the shearing of high quality DNA using KAPA Frag (KAPA Biosystems) as shown in Table 11.

TABLE 11

| Component | uL into Reactions | Final Concentration |
|---|---|---|
| DNA | Total of 200 ng | 4 ng/uL |
| KAPA Frag Buffer | 5 | 1× |
| KAPA Frag Enzyme | 10 | 1× |
| Water | Up to 50 uL | n/a |

Samples were vortexed briefly, spun down and incubated at 37° C. for 15 minutes. After incubation, 5 uL of KAPA Frag Stop Solution was added to the reactions. Thereafter 165 uL of SPRI® beads were used to clean up the reactions. DNA was eluted in 20 uL 10 mM Tris-Cl, pH 8.0 for a final concentration of 10 ng/uL. The fragmented DNA was run on an AGILENT Bioanalyzer to assess shearing success.

Sheared DNA was then used as the input DNA into the Primer 1 Hybridization and Extension Reaction outlined in Table 12.

TABLE 12

| Component | uL into Reactions | Final Concentration |
|---|---|---|
| DNA | Total of 10 or 50 ng | 0.2 or 1 ng/uL |
| KAPA 2G Custom Mastermix | 10 | 1× |
| 9 Target Specific Biotinylated Primers | 1.5 | 30 nM total, 3.3 nM each |
| dATP | 1.9 | 3.8 mM |
| MgCl2 | 5 | 5 mM |
| Water | Up to 50 uL | n/a |

Samples were then incubated as outlined in Table 13

TABLE 13

| Step | ° C. | Time | Ramp Rate |
|---|---|---|---|
| Denaturation | 95 | 5 min | Standard to 80° C. |
| | 80 | 1 second | 0.1-0.3° C./second to 60° C. |
| Hybridization | 60 | 10 min | Standard to 65° C. |
| Extension | 65 | 2 min | Standard to 4° C. |
| | 4 | HOLD | |

Following hybridization and extension with biotinylated primers, samples were mixed at a 1:1 ratio with Dynabeads™ MyOne™ Streptavidin T1 beads. These beads were prepared prior to addition to DNA samples by washing four times with 1× Binding and Wash (B&W) buffer, and resuspending in 2×B&W buffer. The composition of the B&W buffer is described in Table 14.

TABLE 14

| Component | Final in 2× Buffer | Final in 1× Buffer |
|---|---|---|
| Tris-Cl-HCl (pH 7.5) | 40 mM | 20 mM |
| EDTA | 2 mM | 1 mM |
| NaCl | 2M | 1M |
| Tween | 0.1% | 0.05% |
| Water | — | — |

Samples were incubated with 50 uL MyOne™ beads for 10 minutes at room temperature on a rotor. Once biotinylated DNA had bound to beads, samples were placed on a magnet for 3 minutes and the supernatant was then removed and discarded. Beads were washed with the 1×B&W buffer described in Table 14 four times to remove non-biotinylated DNA, and were then resuspended in 20 µL of 10 mM Tris-Cl, pH 8.0.

The resuspended beads were then taken into the Ligation Reaction for ligation of the adaptor sequences to the 3'end of DNA extended in the Primer 1 Hybridization and Extension Reaction. The composition of the Ligation Reaction is described in Table 15.

TABLE 15

| Component | uL into Reactions | Final Concentration |
|---|---|---|
| DNA + Beads | 20 | |
| TA Adaptor | 2 | 20 mM |
| KAPA Ligation Buffer* | 10 | 1× |
| KAPA Ligation Enzyme* | 5 | 1× |
| Water | Up to 50 uL | n/a |

*From the KAPA LTP Library Preparation Kit

Ligation Reactions were incubated at 20° C. for 30 minutes.

Following ligation samples were placed on a magnet at room temperature for 1-3 minutes, the supernatant was removed, and samples were washed twice with the 1×B&W buffer described in Table 14.

Samples were then resuspended in 20 uL 10 mM Tris-Cl, pH 8.0.

These samples were then taken into the Primer 2 Hybridization Reaction outlined in Table 16. During this reaction, target specific primers with outnested portions, equivalent to the sequencing adaptor, are hybridized upstream of the primers added in Primer 1 Hybridization and Extension.

TABLE 16

| Component | uL into Reactions | Final Concentration |
|---|---|---|
| DNA + Beads | 20 | |
| KAPA2G Buffer A | 10 | 1× |
| 9 Outnested Target Specific Primers | 1.5 | 30 nM total, 3.3 nM each |
| Water | Up to 50 uL | n/a |

Primer 2 Hybridization Reactions were incubated at 50° C. for 10 minutes.

Samples were then washed as described for the Ligation reactions.

Samples were resuspended in 20 uL 10 mM Tris-Cl, pH 8.0.

The resuspended beads were then taken into the Extension 2 Reaction. This reaction enabled the extension of Primer 2 and resulted in the release of target DNA molecules into solution. The composition of the Extension 2 reaction is described in Table 17.

TABLE 17

| Component | uL into Reactions | Final Concentration |
|---|---|---|
| DNA + Beads | 20 | |
| KAPA2G Buffer A | 10 | 1× |
| dNTPs | 1 | 0.2 mM each |
| KAPA2G Fast DNA Polymerase | 1 | 5 U |
| Water | Up to 50 uL | n/a |

Extension 2 Reaction samples were incubated at 50° C. for 2 minutes and were then placed directly onto a magnet on ice for 1-3 minutes.

The supernatant (45 uL) was then removed without disturbing the beads, and added to an equal volume (45 uL) of SPRI® beads. A 1× clean-up was performed and samples were eluted in 25 uL 10 mM Tris-Cl, pH 8.0.

Figure 9:
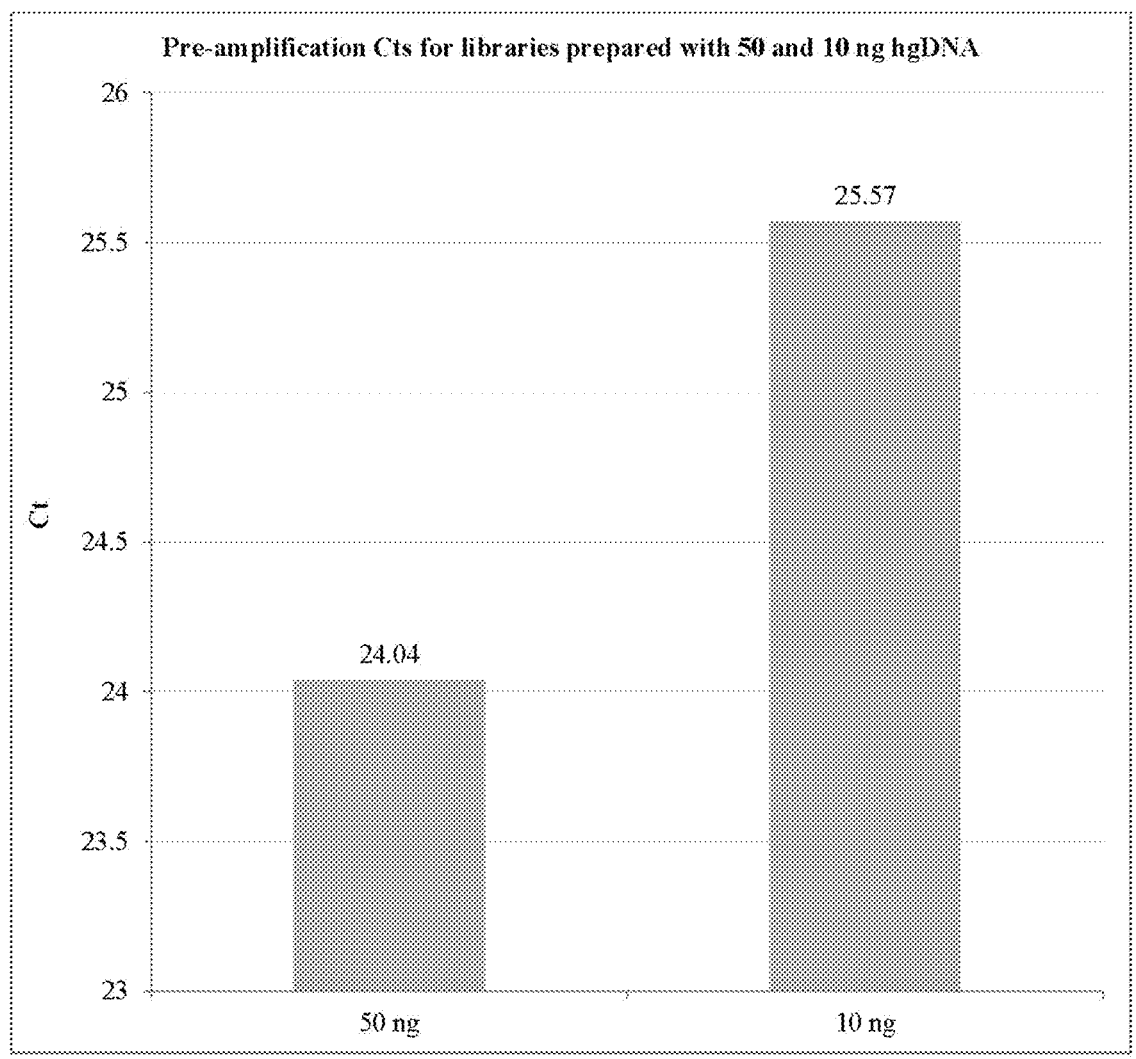
FIG. 9 depicts Cts of an amplification reaction from Example 3.

A qPCR reaction was performed to determine the number of cycles (Ct+2) required to amplify the captured molecules for sequencing. FIG. 9 shows the Cts obtained for each sample.

The last step of the library preparation was the Amplification Reaction. This reaction increased the concentration of the samples, completed the sequencing adaptor sequences and added sample indexes. The amplification reaction and cycling parameters are outlined in Tables 18 and 19.

TABLE 18

| Component | uL into Reactions | Final Concentration |
|---|---|---|
| DNA | 20 | |
| KAPA HiFi HotStart ReadyMix | 25 | 1× |
| P1 Primer | 1.25 | 250 nM |
| Indexed Adaptor Primer | 1.25 | 250 nM |
| Water | Up to 50 uL | n/a |

TABLE 19

| Step | ° C. | Time | Cycles |
|---|---|---|---|
| Initial Denaturation | 98 | 1 min | n/a |
| Denaturation | 98 | 15 sec | 26 (10 ng) or 28 (50 ng) |
| Hybridization | 60 | 30 sec | |
| Extension | 72 | 30 sec | |
| Final Extension | 72 | 1 min | n/a |
| | 4 | HOLD | n/a |

TABLE 20

| Name | Biotinylated Target Specific Sequence (Inner Primer) |
|---|---|
| chr9 − 21970722_Bio | /5Biosg//iSp18//iSp18//iSp18/ GGGACGGCCTGAGTCTCC (SEQ ID NO: 241) |
| chr14 + 105246626_Bio | /5Biosg//iSp18//iSp18//iSp18/ CTGGGTGTGCCAGGACAG (SEQ ID NO: 242) |

TABLE 20-continued

| Name | Biotinylated Target Specific Sequence (Inner Primer) |
|---|---|
| chr18 + 48591980_Bio | /5Biosg//iSp18//iSp18//iSp18/ TTGATTGTATAGTCAGATAGTTACTTTAAAAAATT (SEQ ID NO: 243) |
| chr18 − 48604592_Bio | /5Biosg//iSp18//iSp18//iSp18/ GCAGCAGCTGACAGACCTAA (SEQ ID NO: 244) |
| chr18 + 48604706_Bio | /5Biosg//iSp18//iSp18//iSp18/ GGACCGGATTACCCAAGACAG (SEQ ID NO: 245) |
| chr18 − 48591738_Bio | /5Biosg//iSp18//iSp18//iSp18/ GGAAATAAATGGGAAAGAACATCCTCC (SEQ ID NO: 246) |
| chr13 − 48919139_Bio | /5Biosg//iSp18//iSp18//iSp18/ AATCAGTAACCTTAAAAATTTGTGTTATTTCG (SEQ ID NO: 247) |
| chr18 − 48573338_Bio | /5Biosg//iSp18//iSp18//iSp18/ ATGTCTCCAATTTCTGAAGCAATTTTG (SEQ ID NO: 248) |
| chr18 + 48573611_Bio | /5Biosg//iSp18//iSp18//iSp18/ AGCTCATCCTAGTAAATGTGTTACCATAC (SEQ ID NO: 249) |

The adaptors used in the ligation reaction were prepared from the oligonucleotides listed in Table 21.

TABLE 21

| Name | Sequence |
|---|---|
| 160201P5_W | AATGATACGGCGACCACCGAGATCTACACTCTTT CCCTACACGACGCTCTTCCGATCT (SEQ ID NO: 250) |
| 160201P5_C_TA19 | /5phos/GATCGGAAGAGCGTCGTGT (SEQ ID NO: 251) |

The primers used in Primer 2 Hybridization are listed in Table 22.

TABLE 22

| Name | Outnested Target Specific Sequence (Outer Primer) |
|---|---|
| Ochr9 − 21970772n | GTGACTGGAGTTCAGACGTGTGCTCTTCCGATCT WNNNNNWCTCACGCGCCAATCGGT (SEQ ID NO: 252) |
| Ochr14 + 105246608n | GTGACTGGAGTTCAGACGTGTGCTCTTCCGATCT WNNNNNWAGGCAGCCAGGCAGGAA (SEQ ID NO: 253) |
| Ochr18 + 48591955n | GTGACTGGAGTTCAGACGTGTGCTCTTCCGATCT WNNNNNWAGAAGCCATTGAGAGAGCAAGGTA (SEQ ID NO: 254) |
| Ochr18 − 48604642n | GTGACTGGAGTTCAGACGTGTGCTCTTCCGATCT WNNNNNWCGAAGGTCATCAACACCAATTCCA (SEQ ID NO: 255) |
| Ochr18 + 48604681n | GTGACTGGAGTTCAGACGTGTGCTCTTCCGATCT WNNNNNWAGGATGAGTTTTGTGAAAGGCTGG (SEQ ID NO: 256) |
| Ochr18 − 48591788n | GTGACTGGAGTTCAGACGTGTGCTCTTCCGATCT WNNNNNWGGAACACCAATACTCAGGAGCTATA (SEQ ID NO: 257) |

TABLE 22-continued

| Name | Outnested Target Specific Sequence (Outer Primer) |
|---|---|
| Ochr13 − 48919189n | GTGACTGGAGTTCAGACGTGTGCTCTTCCGATCT WNNNNNWTATGGACACTACAAAGGAAAGAATAGA AAAAGTA (SEQ ID NO: 258) |
| Ochr18 − 48573388n | GTGACTGGAGTTCAGACGTGTGCTCTTCCGATCT WNNNNNWGTCCATTTGTTCAAGTTTTTCCTTTTA AATCAAAT (SEQ ID NO: 259) |
| Ochr18+ 48573575n | GTGACTGGAGTTCAGACGTGTGCTCTTCCGATCT WNNNNNWTTGGATTCTTTAATAACAGCTATAACT ACAAATGG (SEQ ID NO: 260) |

The primers used in the qPCR reaction are listed in Table 23.

TABLE 23

| Name | Outnested Target Specific Sequence (Outer Primer) |
|---|---|
| OUnivAmp | GTGACTGGAGTTCAGACGTGTG (SEQ ID NO: 261) |
| P1 | AATGATACGGCGACCACCGA (SEQ ID NO: 6) |

The primers used in the Amplification Reaction are listed in Table 24.

TABLE 24

| Name | Outnested Target Specific Sequence (Outer Primer) |
|---|---|
| D70X | CAAGCAGAAGACGGCATACGAGAT[index]GTGACTGGAGTT CAGACGTGTGCTCTTC (SEQ ID NO: 262) |

TABLE 24-continued

| Name | Outnested Target Specific Sequence (Outer Primer) |
|---|---|
| P1 | AATGATACGGCGACCACCGA (SEQ ID NO: 6) |

Example 4:117-Target Panel with KAPA Frag DNA

Libraries were prepared from 10 ng Coriell (NA12878) DNA, sheared using KAPA Frag as described in Example 3, and a mix of 117 target specific primers at 3.4 or 34 nM each in the Primer 1 Hybridization and Extension Reaction. These libraries were sequenced on the Illumina Nextseq (Mid Output 300×).

Figure 10A:
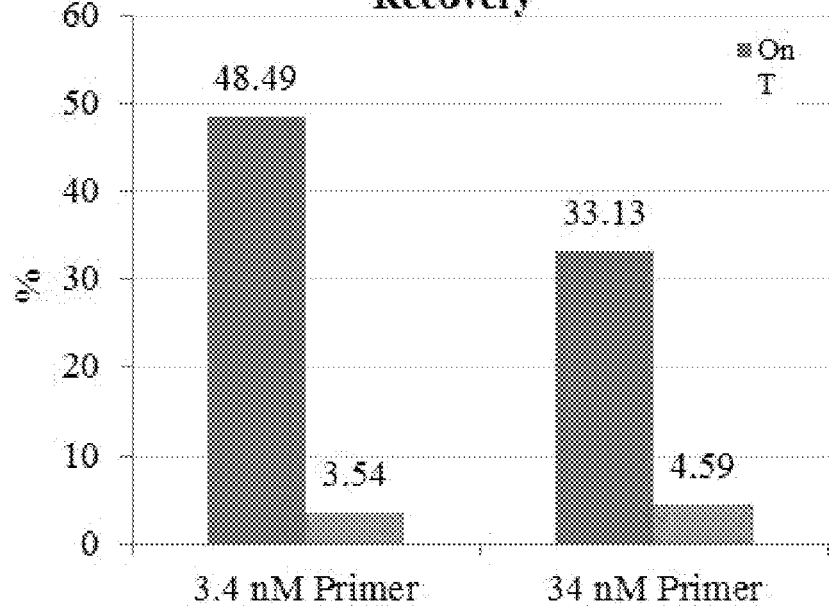
FIGS. 10A-B depict sequencing results from Example 4: on target rate and genome equivalent recovery (GER) (FIG. 10A), and probe coverage uniformity (FIG. 10B).
Figure 10B:
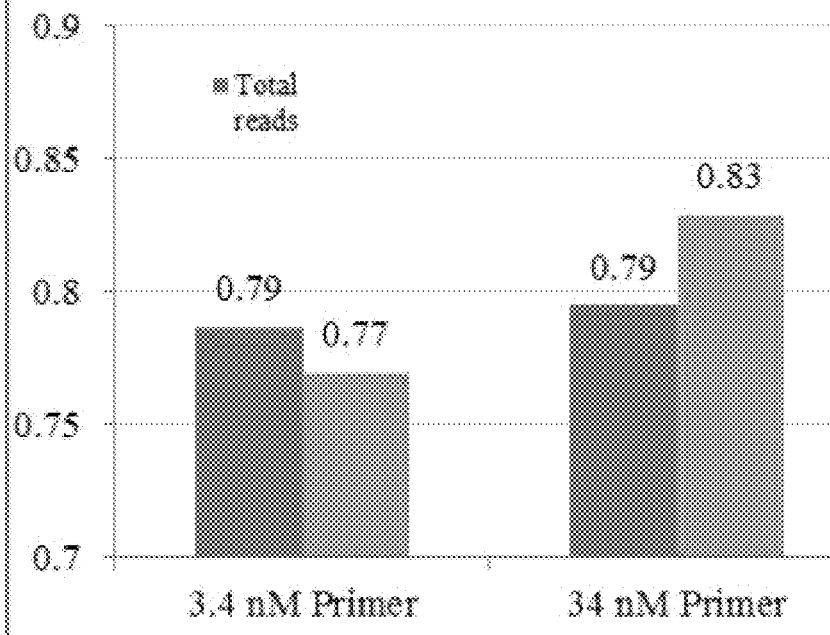

A LabChip GX trace of the final libraries was prepared. FIG. 10A-B show the high level sequencing results of the libraries calculated as described in Example 3; namely on target rate and genome equivalent recovery (GER) (FIG. 10A), as well as probe coverage uniformity (FIG. 10B). Libraries prepared with 3.4 and 34 nM primer in Primer 1 Hybridization and Extension Reaction performed similarly, although some differences were observed. The on-target rates are slightly higher for the 3.4 nM samples (48.5 as opposed to 33.1%), whereas the genome equivalent recovery (GER) and coverage uniformity were slightly higher for the 34 nM samples (4.6 compared to 3.5%, and 0.83 compared to 0.77 respectively).

The first step of library preparation was the Primer 1 Hybridization and Extension Reaction outlined in Table 25.

TABLE 25

| Component | uL into Reactions | Final Concentration |
|---|---|---|
| DNA | 10 ng | 0.2 ng/uL |
| KAPA2G Fast Multiplex PCR | 25 | 1× |
| 117 Target Specific Biotinylated Primers | 2 | 0.4 uM total, 3.4 nM each or 4 uM Total, 34 nM each |
| dATP | 1.9 | 3.8 mM |
| MgCl2 | 5 | 5 mM |
| Water | Up to 50 uL | n/a |

Samples were then incubated as outlined in Table 13.

Following hybridization and extension with biotinylated primers, samples were mixed at a 1:1 ratio with Dynabeads™ MyOne™ Streptavidin T1 beads. These beads were prepared prior to addition to DNA samples by washing four times with 1× Binding and Wash (B&W) buffer, and resuspending in 2×B&W buffer. The composition of the B&W buffer is described in Table 4 with the exception that Tris-Cl pH 7.8 was used instead of Tris-Cl at pH 7.5.

Samples were incubated with 50 uL MyOne™ beads, and bead washes and resuspension were performed as described in Example 1.

The resuspended beads were then taken into the Ligation Reaction as described in Example 3. In this instance, indexed TA adaptors were used.

Following ligation, samples were placed on a magnet at room temperature for 1 minute. The supernatant was removed, and samples were washed with the 1×B&W buffer and eluted in 10 mM Tris-Cl, as described in Example 3.

These samples were then taken into the Primer 2 Hybridization Reaction outlined in Table 26. During this reaction, target specific primers with outnested portions, equivalent to the sequencing adaptor, were hybridized upstream of the primers added in Primer 1 Hybridization and Extension.

TABLE 26

| Component | uL into Reactions | Final Concentration |
|---|---|---|
| DNA + Beads | 20 | |
| KAPA2G Buffer A | 10 | 1× |
| 117 Outnested Target Specific Primers | 2 | 400 nM total, 3.4 nM each |
| Water | Up to 50 uL | n/a |

Primer 2 Hybridization Reactions were incubated at 50° C. for 90 minutes.

Samples were then washed as described for the Ligation reactions.

Samples were resuspended in 20 uL 10 mM Tris-Cl, pH 8.0.

The resuspended beads were then taken into the Extension 2 Reaction as described in Example 3, and outlined in Table 17. This reaction enabled the extension of Primer 2 and resulted in the release of target DNA molecules into solution.

Extension 2 Reaction samples were incubated at 50° C. for 2 minutes and were then placed directly onto a magnet on ice for 1-3 minutes.

The supernatant (47 uL) was then removed without disturbing the beads, and added to an equal volume (47 uL) of SPRI® beads. A 1× clean-up was performed and samples were eluted in 20 uL 10 mM Tris-Cl, pH 8.0.

The final step of the library preparation was the Amplification Reaction outlined in Example 3, with the exception that a 62° C. annealing temperature was used. The amplification reaction and cycling parameters are outlined in Tables 18 and 19.

A 1×SPRI® clean up of the PCR product was then performed and the library was eluted in 25 uL 10 mM Tris-Cl, pH 8.0.

Example 5:117-Target Panel with Tagmented DNA

Figure 11A:
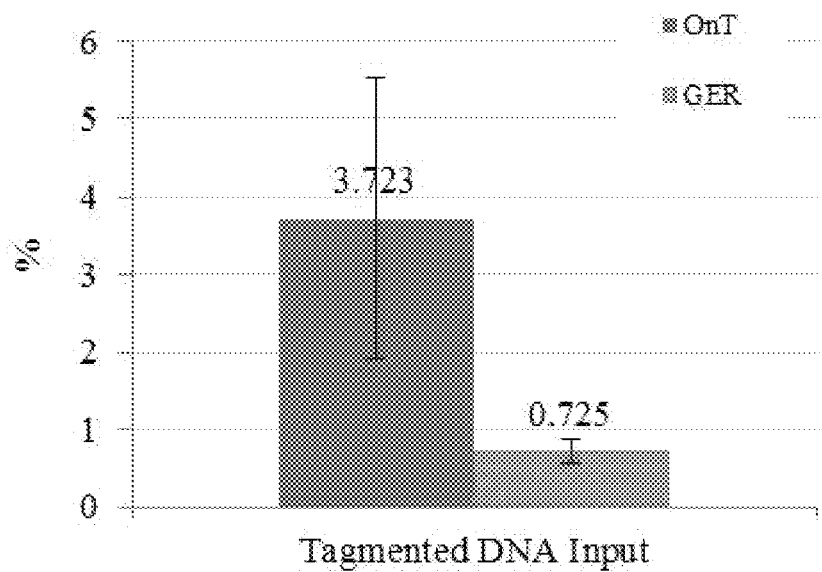
FIGS. 11A-B depict sequencing results from Example 5: on target rate and genome equivalent recovery (GER) (FIG. 11A), and probe coverage uniformity (FIG. 11B).
Figure 11B:
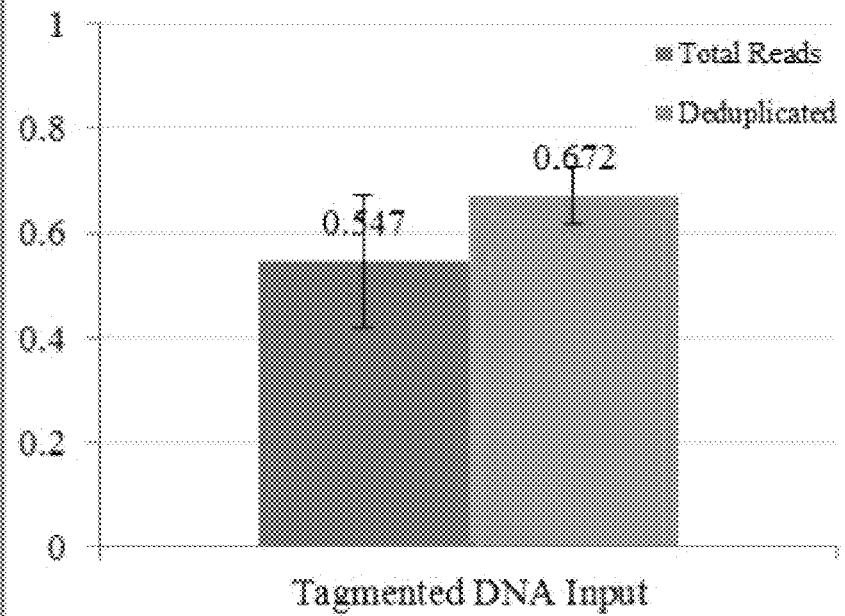

Six replicate libraries were prepared from 10 ng tagmented Coriell (NA12878) DNA and a mix of 117 target specific primers at 3.4 nM each in the Primer 1 Hybridization and Extension Reaction. These libraries were sequenced on the Illumina Nextseq (Mid Output 300×). A LabChip GX trace of a subset of the final libraries was prepared. FIG. 11A-B show the high level sequencing results of the libraries calculated as described in Example 1; namely on target rate and genome equivalent recovery (GER) (FIG. 11A), as well as probe coverage uniformity (FIG. 11B). Libraries prepared with tagmented DNA did not perform as well as those reported in Examples 3 and 4. The on-target rates were low, with a mean of 3.7%, and the genome equivalent recovery (GER) was less than 1%. The coverage uniformity was also slightly lower than observed in Examples 3 and 4, at ~60%.

To prepare these libraries, DNA was tagmented by incubating DNA with transposomes pre-loaded with partial adaptor sequences (R1 arms), as outlined in Table 27.

TABLE 27

| Component | uL into Reactions | Final Concentration |
|---|---|---|
| DNA | | 0.2 ng/uL |
| Reaction buffer | 10 | 1× |
| MnCl$_2$ | 2 | 2 mM |
| Transposase (0.18 mg/ml) | 4 | 7.2 ng/uL |
| Water | Up to 20 uL | n/a |

The tagmentation reaction was carried out by incubating samples at 55° C. for 5 minutes.

After incubation, samples were incubated at room temperature for 5 minutes with 20 μL of GHCl stop solution.

The samples then underwent a 1×SPRI® clean up and were eluted in 10 uL 10 mM Tris-Cl, pH 8.0.

The eluate was incubated at 95° C. for 5 minutes to denature DNA fragments, thereby ensuring that fragments carried the partial adaptor sequences only on the 5' end.

This DNA was used as the input into the Primer 1 Hybridization and Extension Reaction described in Example 4.

All subsequent library preparation steps were as described in Example 4, with the exception of the Ligation Reaction which was excluded, and the final PCR reaction which made use of different primers.

The ligation reaction was unnecessary since the fragments already had partial adaptor sequences added during tagmentation.

The components of the final PCR reaction are outlined in Table 28.

TABLE 28

| Component | uL into Reactions | Final Concentration |
|---|---|---|
| DNA | 20 | |
| KAPA HiFi HotStart ReadyMix | 25 | 1× |
| Indexed i5 Adaptor Primer | 1.25 | 250 nM |
| Indexed i7 Adaptor Primer | 1.25 | 250 nM |
| Water | Up to 50 uL | n/a |

Post-amplification clean-up were as described in Examples 3-4.

While the invention has been described in detail with reference to specific examples, it will be apparent to one skilled in the art that various modifications can be made within the scope of this invention. Thus the scope of the invention should not be limited by the examples described herein, but by the claims presented below.

What is claimed is:

1. A method for sequencing one or more target polynucleotides in a sample, wherein the sample comprises the one or more target polynucleotides and one or more non-target polynucleotides, the method comprising:
   (a) providing a single reaction mixture comprising the sample and a plurality of structurally different first target-specific primers, wherein the one or more target polynucleotides and the one or more non-target polynucleotides in the single reaction mixture are single stranded;
   (b) hybridizing one of the plurality of the structurally different first target-specific primers to each one of the one or more target polynucleotides in the single reaction mixture, wherein each structurally different first target-specific primer of the plurality of structurally different first target-specific primers hybridizes to a location at least 6 nucleotides from a 3' end of each of the one or more target polynucleotides, and where each of the plurality of structurally different first target-specific primers comprises an affinity ligand;
   (c) extending each of the hybridized one of the plurality of structurally different first target-specific primers with a DNA polymerase to form one or more first double-stranded products, wherein each first double-stranded product of the one or more first double-stranded products comprises the extended one of the plurality of structurally different first target-specific primers hybridized to the one of the one or more target polynucleotides, wherein each of the first double-stranded products includes a 3' single-stranded overhang region having at least 6 consecutive nucleotides, wherein the 3' single-stranded overhang region is based on the hybridization of the one of the plurality of the structurally different first target-specific primers to the location at least 6 nucleotides from the end of each of the one or more target polynucleotides;
   (d) removing from the single reaction mixture the structurally different first target-specific primers which are unhybridized to any of the one or more target polynucleotides and the one or more non-target polynucleotides, wherein the removing comprises capturing the affinity ligands on a substrate;
   (e) hybridizing one of a plurality of structurally different second target-specific primers to each of the single-stranded 3' overhang regions of each of the one or more first double-stranded products, wherein each of the plurality of structurally different second target-specific primers comprise (i) a sequence at the 3' end that hybridizes to the single-stranded overhang region of each of the one or more first double-stranded products, and (ii) a sequence at the 5' end that does not hybridize to the single-stranded overhang region of each of the one or more first double-stranded products, wherein the sequence at the 5' end includes a barcode;
   (f) extending the plurality of hybridized second target-specific primers with a DNA polymerase, wherein the DNA polymerase comprises strand displacement activity, 5'-3' double-stranded DNA exonuclease activity, or a combination thereof, thereby displacing or degrading the extended one of the plurality of the structurally different first target-specific primer of each of the first double-stranded products and forming one or more second double-stranded products, wherein each of the one or more second double-stranded products comprises the extended one of the plurality of second structurally different target-specific primers hybridized to the one of the one or more target polynucleotides, wherein each extended second structurally different target-specific primer comprises: (i) a complement of at least a portion of the one of the one or more target polynucleotides; and, (ii) a single-stranded 5' overhang region comprising the barcode;
   (g) attaching a first and a second universal adapter to the one or more second double-stranded products; and
   (h) sequencing the one or more adapter attached second double-stranded products.

2. The method of claim 1, wherein:
   the single-stranded target polynucleotide of a) comprises RNA,
   the extending of c) comprises extending the first target-specific primer with an RNA-dependent DNA polymerase to form a first double-stranded product, wherein the first double-stranded product comprises a cDNA: RNA hybrid.

3. The method of claim 1, wherein attaching of the first and second universal adapters comprises ligation.

4. The method of claim 3, wherein ligation comprises ligating adapters to at least one end of a single-strand of the second double-stranded product by splint ligation.

5. The method of claim 1, prior to step h), further comprising steps: g-1) extending the 3'-end of the target polynucleotides to copy the barcode in the extended second target-specific primers, and g-2) removing the second primer extension products from the second double-stranded products.

6. The method of claim 5, wherein removing of the extended second target-specific primer from the second double-stranded product is performed using an endonuclease selected from Tth Endonuclease IV, Endonuclease IV, Endonuclease V, and Endonuclease VIII and Uracil-N-DNA glycosylase.

7. A method for sequencing one or more target polynucleotides in a sample, wherein the sample comprises the one or more target polynucleotides and one or more non-target polynucleotides, the method comprising:
  (a) providing a single reaction mixture comprising the sample and a plurality of structurally different first target-specific primers, wherein the one or more target polynucleotides and the one or more non-target polynucleotides in the single reaction mixture are single stranded;
  (b) hybridizing one of the plurality of the structurally different first target-specific primers to each one of the one or more target polynucleotides in the single reaction mixture, wherein each structurally different first target-specific primer of the plurality of structurally different first target-specific primers hybridizes at least 6 nucleotides from a 3' end of each of the one or more target polynucleotides and where each of the plurality of structurally different first target-specific primers comprises an affinity ligand;
  (c) extending each of the hybridized one of the plurality of structurally different first target-specific primers with a DNA polymerase to form one or more first double-stranded products, wherein each first double-stranded product of the one or more first double-stranded products comprises the extended one of the plurality of structurally different first target-specific primers hybridized to the one of the one or more target polynucleotides, wherein each of the first double-stranded products includes a 3' single-stranded overhang region having at least 6 consecutive nucleotides;
  (d) removing from the single reaction mixture the structurally different first target-specific primers which are unhybridized to any of the one or more target polynucleotides and the one or more non-target polynucleotides, wherein the removing comprises capturing the affinity ligands on a substrate;
  (e) hybridizing one of a plurality of structurally different second target-specific primers to each of the single-stranded 3' overhang regions of each of the one or more first double-stranded products, wherein each of the plurality of structurally different second target-specific primers comprise (i) a sequence at the 3' end that hybridizes to the single-stranded overhang region of each of the one or more first double-stranded products, and (ii) a barcode;
  (f) extending the plurality of hybridized second target-specific primers with a DNA polymerase, wherein the DNA polymerase comprises strand displacement activity, 5'-3' double-stranded DNA exonuclease activity, or a combination thereof, thereby displacing or degrading the extended one of the plurality of the structurally different first target-specific primer of each of the first double-stranded products and forming one or more second double-stranded products, wherein each of the one or more second double-stranded products comprises the extended one of the plurality of second structurally different target-specific primers hybridized to the one of the one or more target polynucleotides;
  (g) attaching a first and a second universal adapter to the one or more second double-stranded products; and
  (h) sequencing the one or more adapter attached second double-stranded products.

8. A method for enriching a sample for one or more target polynucleotides, wherein the sample comprises the one or more target polynucleotides and one or more non-target polynucleotides, the method comprising:
  (a) providing a single reaction mixture comprising the sample and a plurality of structurally different first target-specific primers, wherein the one or more target polynucleotides and the one or more non-target polynucleotides in the single reaction mixture are single stranded;
  (b) hybridizing one of the plurality of the structurally different first target-specific primers to each one of the one or more target polynucleotides in the single reaction mixture, wherein each structurally different first target-specific primer of the plurality of structurally different first target-specific primers hybridizes at least 6 nucleotides from a 3' end of each of the one or more target polynucleotides and where each of the plurality of structurally different first target-specific primers comprises an affinity ligand;
  (c) extending each of the hybridized one of the plurality of structurally different first target-specific primers with a DNA polymerase to form one or more first double-stranded products, wherein each first double-stranded product of the one or more first double-stranded products comprises the extended one of the plurality of structurally different first target-specific primers hybridized to the one of the one or more target polynucleotides, wherein each of the first double-stranded products includes a 3' single-stranded overhang region having at least 6 consecutive nucleotides;
  (d) removing from the single reaction mixture the structurally different first target-specific primers which are unhybridized to any of the one or more target polynucleotides and the one or more non-target polynucleotides, wherein the removing comprises capturing the affinity ligands on a substrate;
  (e) hybridizing one of a plurality of structurally different second target-specific primers to each of the single-stranded 3' overhang regions of each of the one or more first double-stranded products, wherein each of the plurality of structurally different second target-specific primers comprise (i) a sequence at the 3' end that hybridizes to the single-stranded overhang region of each of the one or more first double-stranded products, and (ii) a barcode; and
  (f) extending the plurality of hybridized second target-specific primers with a DNA polymerase, wherein the DNA polymerase comprises strand displacement activity, 5'-3' double-stranded DNA exonuclease activity, or a combination thereof, thereby displacing or degrading the extended one of the plurality of the structurally different first target-specific primer of each of the first double-stranded products and forming one or more second double-stranded products, wherein each of the one or more second double-stranded products comprises the extended one of the plurality of second structurally different target-specific primers hybridized to the one of the one or more target polynucleotides.

* * * * *